US012753449B2

(12) United States Patent
Beisel et al.

(10) Patent No.: US 12,753,449 B2
(45) Date of Patent: Oct. 6, 2026

(54) RNA DETECTION AND TRANSCRIPTION-DEPENDENT EDITING WITH REPROGRAMMED TRACRRNAS

(71) Applicants: HELMHOLTZ-ZENTRUM FÜR INFEKTIONSFORSCHUNG GMBH, Braunschweig (DE); JULIUS-MAXIMILIANS-UNIVERSITÄT WÜRZBURG, Würzburg (DE)

(72) Inventors: Chase Beisel, Würzburg (DE); Chunlei Jiao, Würzburg (DE); Cynthia Mira Sharma, Würzburg (DE); Gaurav Dugur, Amsterdam (NL)

(73) Assignees: Helmholtz-Zentrum für Infektionsforschung GmbH, Braunschweig (DE); Julius-Maximilians-Universität Würzburg, Würzburg (DE)

(*) Notice: Subject to any disclaimer, the term of this patent is extended or adjusted under 35 U.S.C. 154(b) by 1074 days.

(21) Appl. No.: 17/801,243

(22) PCT Filed: Mar. 1, 2021

(86) PCT No.: PCT/EP2021/055060
§ 371 (c)(1),
(2) Date: Aug. 20, 2022

(87) PCT Pub. No.: WO2021/170877
PCT Pub. Date: Sep. 2, 2021

(65) Prior Publication Data

US 2023/0175078 A1 Jun. 8, 2023

(30) Foreign Application Priority Data

Feb. 28, 2020 (EP) .................................... 20160004

(51) Int. Cl.
*C12Q 1/68* (2018.01)
*C12N 15/11* (2006.01)
(Continued)

(52) U.S. Cl.
CPC ............ *C12Q 1/6897* (2013.01); *C12N 15/11* (2013.01); *C12N 2310/20* (2017.05); *C12Q 1/6823* (2013.01)

(58) Field of Classification Search
None
See application file for complete search history.

(56) References Cited

U.S. PATENT DOCUMENTS

2019/0032053 A1 1/2019 Ji et al.
2021/0363518 A1* 11/2021 Sontheimer .......... C12N 15/907

FOREIGN PATENT DOCUMENTS

KR 10-2020-0017479 A 2/2020
WO 2019/027728 A1 2/2019
(Continued)

OTHER PUBLICATIONS

Karvelis, Tautvydas et al. "crRNA and tracrRNA guide Cas9-mediated DNA interference in Streptococcus thermophilus." RNA Biology 10(5):841-851, Mar. 27, 2013.
(Continued)

*Primary Examiner* — Aaron A Priest
(74) *Attorney, Agent, or Firm* — SALIWANCHIK, LLOYD & EISENSCHENK

(57) ABSTRACT

The present invention relates to methods for detecting at least one sensed RNA in a cell, tissue, and/or sample using at least one non-naturally occurring tracrRNA specifically hybridizing with said sensed RNA and at least one tracrRNA-dependent CRISPR nuclease enzyme binding to
(Continued)

Figure 1:
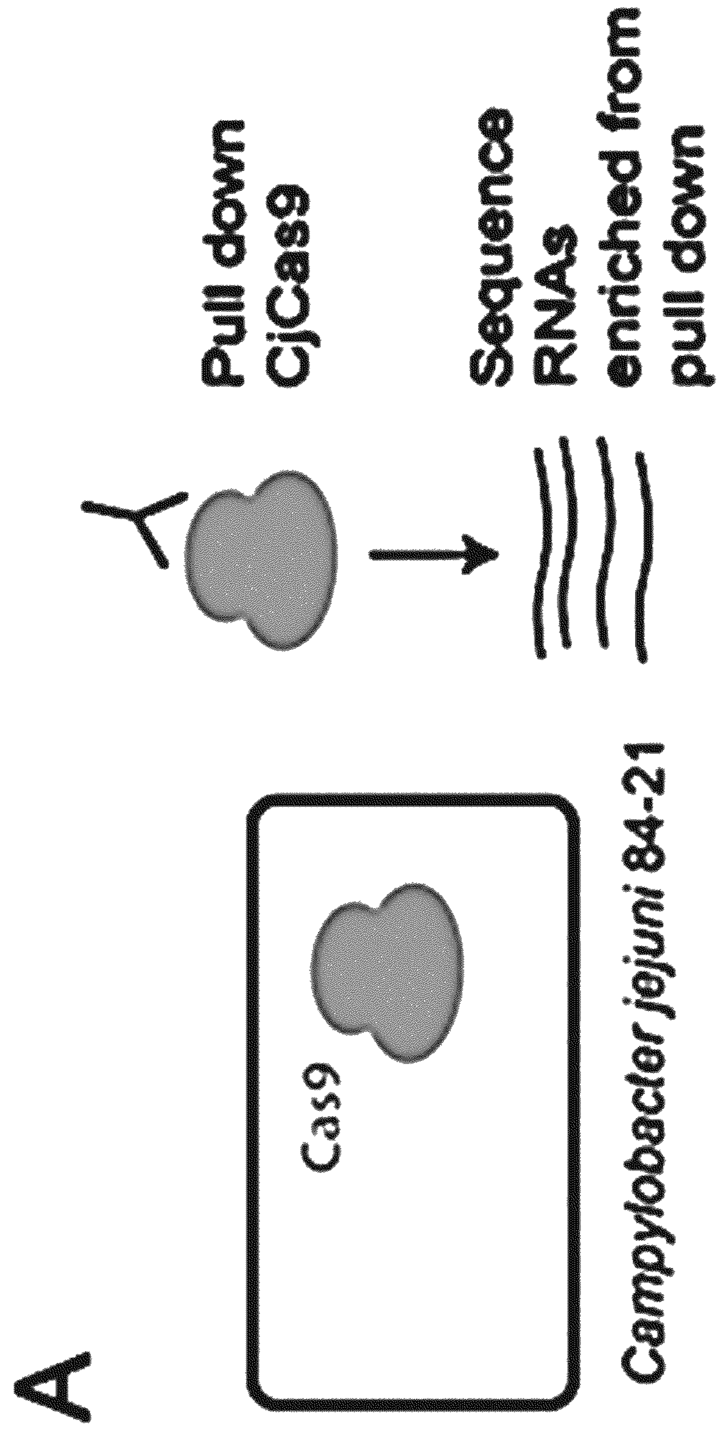
Figure 1:
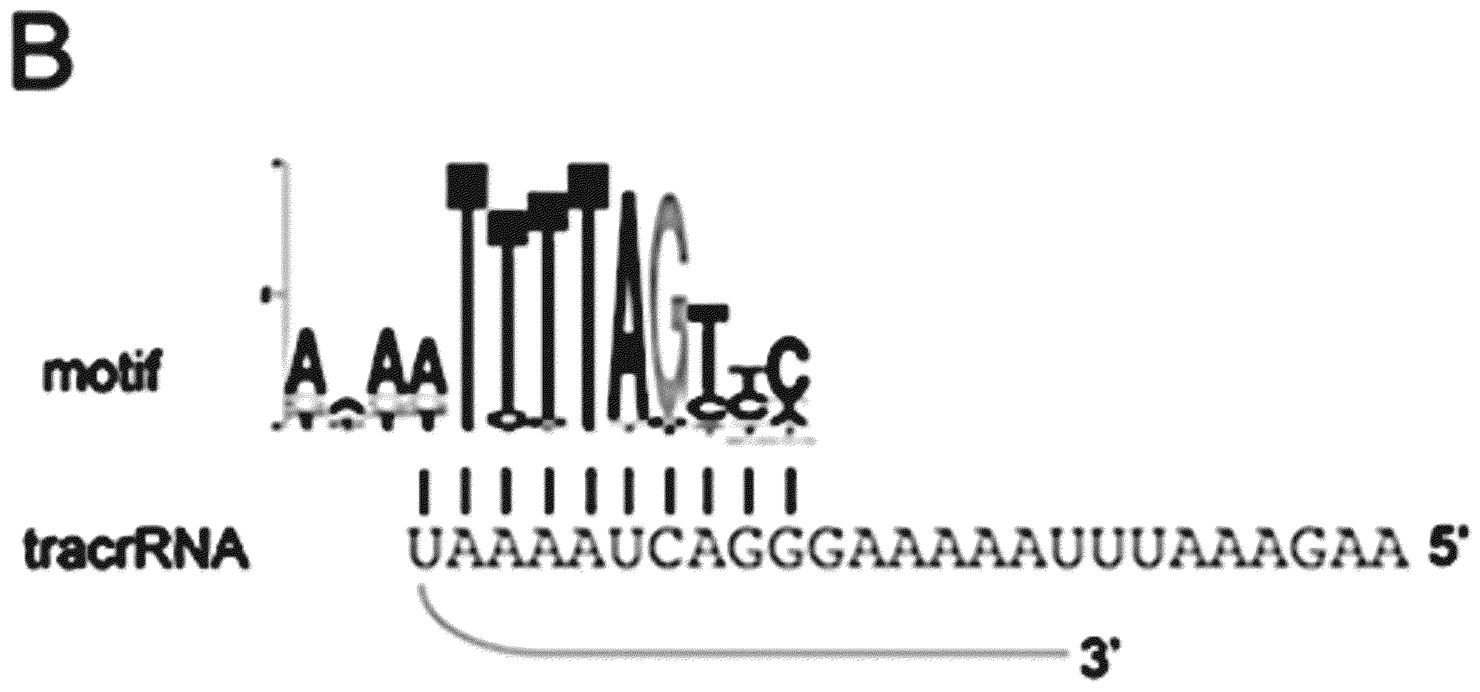
Figure 1:
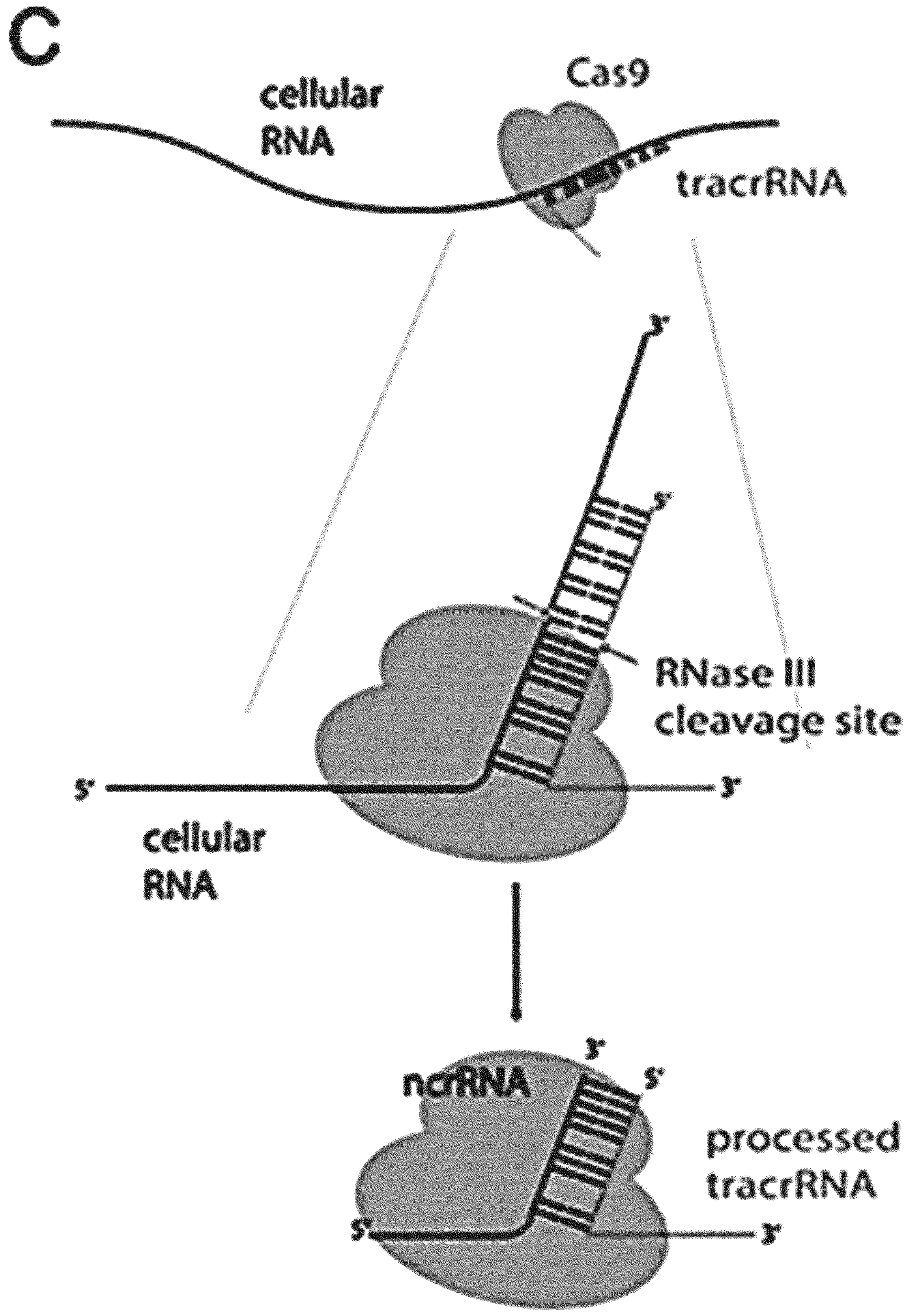

at least one target nucleic acid, as well as respective systems and diagnostic and therapeutic uses thereof.

19 Claims, 48 Drawing Sheets

Specification includes a Sequence Listing.

(51) Int. Cl.
*C12Q 1/6897* (2018.01)
*C12Q 1/6823* (2018.01)

(56) References Cited

FOREIGN PATENT DOCUMENTS

| | | | |
|---|---|---|---|
| WO | 2019/126037 | A1 | 6/2019 |
| WO | 2019/183000 | A1 | 9/2019 |

OTHER PUBLICATIONS

Schmidt, Florian et al. "Transcriptional recording by CRISPR spacer acquisition from RNA." Nature 562 (7727):380-385, Oct. 3, 2018.

Su, Kuan-Chung et al. "CRISPR/Cas9-based gene targeting using synthetic guide RNAs enables robust cell biological analyses." Molecular Biology of the Cell 29(20):2370-2377, Oct. 1, 2018.

Tan, Jenille and Scott E. Martin", Validation of Synthetic CRISPR Reagents as a Tool for Arrayed Functional Genomic Screening." PLOS One 11(12):e0168968, Dec. 28, 2016.

* cited by examiner

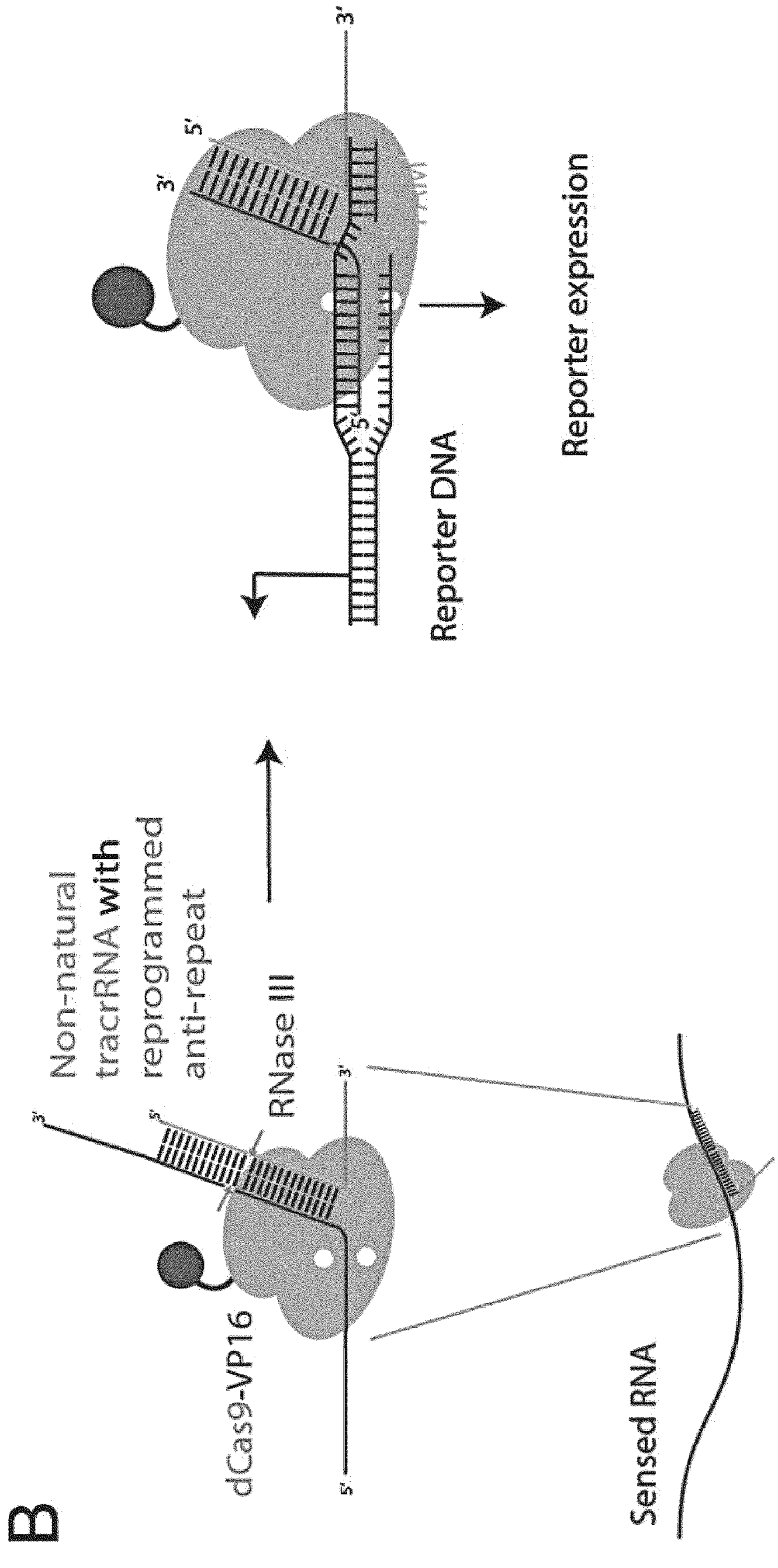
B
dCas9-VP16
Non-natural tracrRNA with reprogrammed anti-repeat
RNase III
Sensed RNA
Reporter DNA
Reporter expression
5'
3'

A

B

B

Guide AGA$_3$A$_4$U$_5$U$_6$U$_7$A$_8$UGUGAAUUUUAUUG

Target AGA$_3$A$_4$T$_5$T$_6$T$_7$A$_8$TGTGAATTTTATTGtgAGAAA

PAM

SEQUENCE LISTING

```
<160> NUMBER OF SEQ ID NOS: 128

<210> SEQ ID NO 1
<211> LENGTH: 58
<212> TYPE: DNA
<213> ORGANISM: Homo sapiens

<400> SEQUENCE: 1

aatgatacgg cgaccaccga gatctacact ctttccctac acgacgctct tccgatct       58


<210> SEQ ID NO 2
<211> LENGTH: 63
<212> TYPE: DNA
<213> ORGANISM: Homo sapiens
<220> FEATURE:
<221> NAME/KEY: misc_feature
<222> LOCATION: (25)..(30)
<223> OTHER INFORMATION: n is a, c, g, or t

<400> SEQUENCE: 2

caagcagaag acggcatacg agatnnnnnn gtgactggag ttcagacgtg tgctcttccg     60

atc                                                                   63


<210> SEQ ID NO 3
<211> LENGTH: 51
<212> TYPE: DNA
<213> ORGANISM: Homo sapiens

<400> SEQUENCE: 3

ccgagagcat cgatcctagc atggatgcat ttgacagcta gctcagtcct a              51


<210> SEQ ID NO 4
<211> LENGTH: 52
<212> TYPE: DNA
<213> ORGANISM: Homo sapiens

<400> SEQUENCE: 4

gatcctacag tatcccagtg tcgaggtatt atccggatat agttcctcct tt             52


<210> SEQ ID NO 5
<211> LENGTH: 224
<212> TYPE: DNA
<213> ORGANISM: Homo sapiens

<400> SEQUENCE: 5

ttgacagcta gctcagtcct aggtataatg ctagctataa attagaaagt gaaaataaag     60

ttttagtccc tttttaaatt tctttatggt aaaatctgct aacaaagccc gaaaggaagc    120
```

tgagttggct gctgccaccg ctgagcaata actagcataa ccccttgggg cctctaaacg 180
ggtcttgagg ggtttttttgc tgaaaggagg aactatatcc ggat 224

<210> SEQ ID NO 6
<211> LENGTH: 274
<212> TYPE: DNA
<213> ORGANISM: Homo sapiens

<400> SEQUENCE: 6
ttgacagcta gctcagtcct aggtataatg ctagccaagt tcttctgctg caattgtagc 60
taaacttgaa caaaataata ttccctataa attagaaagt gaaaataaag ttttagtccc 120
tttttaaatt tctttatggt aaaatctgct aacaaagccc gaaaggaagc tgagttggct 180
gctgccaccg ctgagcaata actagcataa ccccttgggg cctctaaacg ggtcttgagg 240 ggtttttttgc tgaaaggagg aactatatcc ggat 274

<210> SEQ ID NO 7
<211> LENGTH: 374
<212> TYPE: DNA
<213> ORGANISM: Homo sapiens

<400> SEQUENCE: 7
ttgacagcta gctcagtcct aggtataatg ctagcattat agttgtggtt gggtttttgg 60 ttttttagc tttatttcgt ggaagtggta gtaatgcaaa taatggatat gcagttttag 120
ttgaaaatgt aagcccaagt tcttctgctg caattgtagc taaacttgaa caaaataata 180
ttccctataa attagaaagt gaaaataaag ttttagtccc tttttaaatt tctttatggt 240
aaaatctgct aacaaagccc gaaaggaagc tgagttggct gctgccaccg ctgagcaata 300
actagcataa ccccttgggg cctctaaacg ggtcttgagg ggtttttttgc tgaaaggagg 360 aactatatcc ggat 374

<210> SEQ ID NO 8
<211> LENGTH: 40
<212> TYPE: DNA
<213> ORGANISM: Homo sapiens

<400> SEQUENCE: 8
cactgggata ctgtaggatc ttgacagcta gctcagtcct 40

<210> SEQ ID NO 9
<211> LENGTH: 48
<212> TYPE: DNA
<213> ORGANISM: Homo sapiens

<400> SEQUENCE: 9
ggatcgatcg attctttcaa gcttatccgg atatagttcc tcctttca 48

<210> SEQ ID NO 10
<211> LENGTH: 274
<212> TYPE: DNA
<213> ORGANISM: Homo sapiens

<400> SEQUENCE: 10
ttgacagcta gctcagtcct aggtataatg ctagctataa attagaaagt gaaaataaag 60
ttttagtccc tttttaaatt tctttatggt aaaatatcgt caaagaatgt ttattgcaag 120
cgaaggtctt ataaaagata gtcgcctgct aacaaagccc gaaaggaagc tgagttggct 180
gctgccaccg ctgagcaata actagcataa ccccttgggg cctctaaacg ggtcttgagg 240
ggttttttgc tgaaaggagg aactatatcc ggat 274

<210> SEQ ID NO 11
<211> LENGTH: 374
<212> TYPE: DNA
<213> ORGANISM: Homo sapiens

<400> SEQUENCE: 11
ttgacagcta gctcagtcct aggtataatg ctagctataa attagaaagt gaaaataaag 60
ttttagtccc tttttaaatt tctttatggt aaaatatcgt caaagaatgt ttattgcaag 120
cgaaggtctt ataaaagata gtcgcgtggg ttttgaagct tttgatactc aagcttttgg 180
agctacaaat gaagagcaaa aggtaaaata ccaaagagcc atagaaggcg aacttgcaag 240
aactactgct aacaaagccc gaaaggaagc tgagttggct gctgccaccg ctgagcaata 300
actagcataa ccccttgggg cctctaaacg ggtcttgagg ggttttttgc tgaaaggagg 360
aactatatcc ggat 374

<210> SEQ ID NO 12
<211> LENGTH: 568
<212> TYPE: DNA
<213> ORGANISM: Homo sapiens

<400> SEQUENCE: 12
cactgggata ctgtaggatc ttgacagcta gctcagtcct aggtataatg ctagctataa 60
attagaaagt gaaaataaag ttttagtccc tttttaaatt tctttatggt aaaatatcgt 120
caaagaatgt ttattgcaag cgaaggtctt ataaaagata gtcgcgtggg ttttgaagct 180
tttgatactc aagcttttgg agctacaaat gaagagcaaa aggtaaaata ccaaagagcc 240
atagaaggcg aacttgcaag aactattgag actttagaac ctattcgtag cgctgttgta 300
cacatagcat ttcctaaaga tagtgttttt accgaaaggc aaattccgcc tacagcttca 360
gttgttgtta atgttcgcga aggcttaaag cttactagaa aacaaattga tggtactgct 420
aacaaagccc gaaaggaagc tgagttggct gctgccaccg ctgagcaata actagcataa 480
ccccttgggg cctctaaacg ggtcttgagg ggttttttgc tgaaaggagg aactatatcc 540
ggataagctt gaaagaatcg atcgatcc 568

<210> SEQ ID NO 13
<211> LENGTH: 35
<212> TYPE: DNA
<213> ORGANISM: Homo sapiens

<400> SEQUENCE: 13
ttgacagcta gctcagtcct aggtataatg ctagc 35

<210> SEQ ID NO 14
<211> LENGTH: 30
<212> TYPE: DNA
<213> ORGANISM: Homo sapiens

<400> SEQUENCE: 14
caaagcccgc cgaaaggcgg gcttttctgt 30

<210> SEQ ID NO 15
<211> LENGTH: 32
<212> TYPE: DNA
<213> ORGANISM: Homo sapiens

<400> SEQUENCE: 15
tataaattag aaagtgaaaa taaaagaaac ac 32

<210> SEQ ID NO 16
<211> LENGTH: 98
<212> TYPE: RNA
<213> ORGANISM: Homo sapiens

<400> SEQUENCE: 16
gugccggugu cguugucggc augggguuua gucccugaaa agggacuaaa auaaagaguu 60
ugcgggacuc ugcgggguua caauccccua aaaccgcu 98

<210> SEQ ID NO 17
<211> LENGTH: 99
<212> TYPE: RNA
<213> ORGANISM: Homo sapiens

<400> SEQUENCE: 17
uauaaauuag aaagugaaaa uaaaguuuua gucccugaaa agggacuaaa auaaagaguu 60
ugcgggacuc ugcgggguua caauccccua aaaccgcuu 99

<210> SEQ ID NO 18
<211> LENGTH: 99
<212> TYPE: RNA
<213> ORGANISM: Homo sapiens

<400> SEQUENCE: 18
uauaaauuag aaagugaaaa uaaaguuuua gucuaggaaa cuagacuaaa auaaagaguu 60
ugcgggacuc ugcgggguua caauccccua aaaccgcuu 99

<210> SEQ ID NO 19
<211> LENGTH: 99
<212> TYPE: RNA
<213> ORGANISM: Homo sapiens

<400> SEQUENCE: 19
uauaaauuag aaagugaaaa uaaaguuuua aguccugaaa aggacuuaaa auaaagaguu 60
ugcgggacuc ugcgggguua caauccccua aaaccgcuu 99

<210> SEQ ID NO 20
<211> LENGTH: 99
<212> TYPE: RNA
<213> ORGANISM: Homo sapiens

<400> SEQUENCE: 20
uauaaauuag aaagugaaaa uaaaguuccg gucccugaaa agggaccgga auaaagaguu 60
ugcgggacuc ugcgggguua caauccccua aaaccgcuu 99

<210> SEQ ID NO 21
<211> LENGTH: 99
<212> TYPE: RNA
<213> ORGANISM: Homo sapiens

<400> SEQUENCE: 21
uauaaauuag aaagugaaaa uaaagcguua gucccugaaa agggacuaac guaaagaguu 60
ugcgggacuc ugcgggguua caauccccua aaaccgcuu 99

<210> SEQ ID NO 22
<211> LENGTH: 98

<212> TYPE: RNA
<213> ORGANISM: Homo sapiens

<400> SEQUENCE: 22
uauaaauuag aaagugaaaa uaaaguuuua guccugaaaa gggacuaaaa uaaagaguuu 60
gcgggacucu gcggggguuac aaucccccuaa aaccgcuu 98

<210> SEQ ID NO 23
<211> LENGTH: 98
<212> TYPE: RNA
<213> ORGANISM: Homo sapiens

<400> SEQUENCE: 23
uauaaauuag aaagugaaaa uaaaguuuua ucccugaaaa gggacuaaaa uaaagaguuu 60
gcgggacucu gcgggguuac aauccccuaa aaccgcuu 98

<210> SEQ ID NO 24
<211> LENGTH: 98
<212> TYPE: RNA
<213> ORGANISM: Homo sapiens

<400> SEQUENCE: 24
uauaaauuag aaagugaaaa uaaaguuuag ucccugaaaa gggacuaaaa uaaagaguuu 60
gcgggacucu gcgggguuac aauccccuaa aaccgcuu 98

<210> SEQ ID NO 25
<211> LENGTH: 97
<212> TYPE: RNA
<213> ORGANISM: Homo sapiens

<400> SEQUENCE: 25
uauaaauuag aaagugaaaa uaaaguuuua gucugaaaag ggacuaaaau aaagaguuug 60
cgggacucug cgggguuaca auccccuaaa accgcuu 97

<210> SEQ ID NO 26
<211> LENGTH: 97
<212> TYPE: RNA
<213> ORGANISM: Homo sapiens

<400> SEQUENCE: 26
uauaaauuag aaagugaaaa uaaaguuuuu cccugaaaag ggacuaaaau aaagaguuug 60
cgggacucug cgggguuaca auccccuaaa accgcuu 97

<210> SEQ ID NO 27
<211> LENGTH: 97
<212> TYPE: RNA
<213> ORGANISM: Homo sapiens

<400> SEQUENCE: 27
uauaaauuag aaagugaaaa uaaaguuagu cccugaaaag ggacuaaaau aaagaguuug 60
cgggacucug cgggguuaca auccccuaaa accgcuu 97

<210> SEQ ID NO 28
<211> LENGTH: 100
<212> TYPE: RNA
<213> ORGANISM: Homo sapiens

<400> SEQUENCE: 28
uauaaauuag aaagugaaaa uaaaguuuua guccacugaa aagggacuaa aauaaagagu 60
uugcgggacu cugcggggguu acaaucccccu aaaaccgcuu 100

<210> SEQ ID NO 29
<211> LENGTH: 100
<212> TYPE: RNA
<213> ORGANISM: Homo sapiens

<400> SEQUENCE: 29
uauaaauuag aaagugaaaa uaaaguuuua gaucccugaa aagggacuaa aauaaagagu 60
uugcgggacu cugcggggguu acaaucccccu aaaaccgcuu 100

<210> SEQ ID NO 30
<211> LENGTH: 100
<212> TYPE: RNA
<213> ORGANISM: Homo sapiens

<400> SEQUENCE: 30
uauaaauuag aaagugaaaa uaaaguuauu agucccugaa aagggacuaa aauaaagagu 60
uugcgggacu cugcggggguu acaaucccccu aaaaccgcuu 100

<210> SEQ ID NO 31
<211> LENGTH: 101
<212> TYPE: RNA
<213> ORGANISM: Homo sapiens

<400> SEQUENCE: 31
uauaaauuag aaagugaaaa uaaaguuuua guccaacuga aaagggacua aaauaaagag 60
uuugcgggac ucugcggggu uacaaucccc uaaaaccgcu u 101

<210> SEQ ID NO 32
<211> LENGTH: 101
<212> TYPE: RNA
<213> ORGANISM: Homo sapiens

<400> SEQUENCE: 32
uauaaauuag aaagugaaaa uaaaguuuua gaaucccuga aaagggacua aaauaaagag 60
uuugcgggac ucugcggggu uacaaucccc uaaaaccgcu u 101

<210> SEQ ID NO 33
<211> LENGTH: 101
<212> TYPE: RNA
<213> ORGANISM: Homo sapiens

<400> SEQUENCE: 33
uauaaauuag aaagugaaaa uaaaguuaau uagucccuga aaagggacua aaauaaagag 60
uuugcgggac ucugcggggu uacaaucccc uaaaaccgcu u 101

<210> SEQ ID NO 34
<211> LENGTH: 99
<212> TYPE: RNA
<213> ORGANISM: Homo sapiens

<400> SEQUENCE: 34
uauaaauuag aaagugaaaa uaaaguuuua gucacugaaa agggacuaaa auaaagaguu 60
ugcgggacuc ugcgggguua caaucccccua aaaccgcuu 99

<210> SEQ ID NO 35
<211> LENGTH: 99
<212> TYPE: RNA
<213> ORGANISM: Homo sapiens

<400> SEQUENCE: 35
uauaaauuag aaagugaaaa uaaaguuuuu gucccugaaa agggacuaaa auaaagaguu 60
ugcgggacuc ugcgggguua caaucccua aaaccgcuu 99

<210> SEQ ID NO 36
<211> LENGTH: 99
<212> TYPE: RNA
<213> ORGANISM: Homo sapiens

<400> SEQUENCE: 36
uauaaauuag aaagugaaaa uaaagauuua gucccugaaa agggacuaaa auaaagaguu 60
ugcgggacuc ugcgggguua caaucccua aaaccgcuu 99

<210> SEQ ID NO 37
<211> LENGTH: 99
<212> TYPE: RNA
<213> ORGANISM: Homo sapiens

<400> SEQUENCE: 37
uauaaauuag aaagugaaaa uaaaguuuua guaacugaaa agggacuaaa auaaagaguu 60
ugcgggacuc ugcgggguua caaucccua aaaccgcuu 99

<210> SEQ ID NO 38
<211> LENGTH: 99
<212> TYPE: RNA
<213> ORGANISM: Homo sapiens

<400> SEQUENCE: 38
uauaaauuag aaagugaaaa uaaaguuuuu cucccugaaa agggacuaaa auaaagaguu 60
ugcgggacuc ugcgggguua caaucccua aaaccgcuu 99

<210> SEQ ID NO 39
<211> LENGTH: 99
<212> TYPE: RNA
<213> ORGANISM: Homo sapiens

<400> SEQUENCE: 39
uauaaauuag aaagugaaaa uaaagaauua gucccugaaa agggacuaaa auaaagaguu 60
ugcgggacuc ugcgggguua caaucccua aaaccgcuu 99

<210> SEQ ID NO 40
<211> LENGTH: 99
<212> TYPE: RNA
<213> ORGANISM: Homo sapiens

<400> SEQUENCE: 40
uauaaauuag aaagugaaaa uaaaguuuua gucucugaaa agggacuaaa auaaagaguu 60
ugcgggacuc ugcgggguua caaucccua aaaccgcuu 99

<210> SEQ ID NO 41
<211> LENGTH: 99
<212> TYPE: RNA
<213> ORGANISM: Homo sapiens

<400> SEQUENCE: 41
uauaaauuag aaagugaaaa uaaaguuuua guuccugaaa agggacuaaa auaaagaguu 60
ugcgggacuc ugcgggguua caaucccua aaaccgcuu 99

<210> SEQ ID NO 42
<211> LENGTH: 99
<212> TYPE: RNA
<213> ORGANISM: Homo sapiens

<400> SEQUENCE: 42
uauaaauuag aaagugaaaa uaaaguuuua guuucugaaa agggacuaaa auaaagaguu 60
ugcgggacuc ugcgggguua caaucccua aaaccgcuu 99

<210> SEQ ID NO 43
<211> LENGTH: 55
<212> TYPE: DNA
<213> ORGANISM: Homo sapiens

<400> SEQUENCE: 43
tgagctaaca ccgtgcgtgt tgacaatttt acctctggcg gtgataatgg ttgca 55

<210> SEQ ID NO 44
<211> LENGTH: 129
<212> TYPE: DNA
<213> ORGANISM: Homo sapiens

<400> SEQUENCE: 44
ctgctaacaa agcccgaaag gaagctgagt tggctgctgc caccgctgag caataactag 60
cataacccct tggggcctct aaacgggtct tgaggggttt tttgctgaaa ggaggaacta 120
tatccggat 129

<210> SEQ ID NO 45
<211> LENGTH: 72
<212> TYPE: RNA
<213> ORGANISM: Homo sapiens

<400> SEQUENCE: 45
aagaaauuua aaaagggacu aaaauaaaga guuugcggga cucugcgggg uuacaauccc 60
cuaaaaccgc uu 72

<210> SEQ ID NO 46
<211> LENGTH: 60
<212> TYPE: RNA
<213> ORGANISM: Homo sapiens

<400> SEQUENCE: 46
gugccggugu cguugucggc augggguuua gucccuuuuu aaauuucuuu augguaaaau 60

<210> SEQ ID NO 47
<211> LENGTH: 360
<212> TYPE: RNA
<213> ORGANISM: Homo sapiens

<400> SEQUENCE: 47
uauaaauuag aaagugaaaa uaaaguuuua gucccuuuuu aaauuucuuu augguaaaau 60
aucgucaaag aauguuuauu gcaagcgaag gucuuauaaa agauagucgc guggguuuug 120
aagcuuuuga uacucaagcu uuuggagcua caaaugaaga gcaaaaggua aaauaccaaa 180
gagccauaga aggcgaacuu gcaagaacua uugagacuuu agaaccuauu cguagcgcug 240
uuguacacau agcauuuccu aaagauagug uuuuuaccga aaggcaaauu ccgccuacag 300
cuucaguugu uguuaauguu cgcgaaggcu uaaagcuuac uagaaaacaa auugauggua 360

<210> SEQ ID NO 48
<211> LENGTH: 395
<212> TYPE: RNA
<213> ORGANISM: Homo sapiens

<400> SEQUENCE: 48
uugacagcua gcucaguccu agguauaaug cuagcuauaa auuagaaagu gaaaauaaag 60
uuuuaguccc uuuuuaauuu ucuuuauggu aaaauaucgu caaagaaugu uuauugcaag 120
cgaaggucuu auaaaagaua gucgcguggg uuuugaagcu uuugauacuc aagcuuuugg 180
agcuacaaau gaagagcaaa agguaaaaua ccaaagagcc auagaaggcg aacuugcaag 240
aacuauugag acuuuagaac cuauucguag cgcuguugua cacauagcau uuccuaaaga 300
uaguguuuuu accgaaaggc aaauuccgcc uacagcuuca guuguuguua auguucgcga 360
aggcuuaaag cuuacuagaa aacaaauuga uggua 395

<210> SEQ ID NO 49
<211> LENGTH: 360
<212> TYPE: RNA
<213> ORGANISM: Homo sapiens

<400> SEQUENCE: 49
uauaaauuag aaagugaaaa uaaaguuuua gucccuuugu agcuuuuuuu augguaaaau 60
aucgucaaag aauguuuauu gcaagcgaag gucuuauaaa agauagucgc gugggu uuug 120 aagcuuuuga uacucaagcu uuuggagcua caaaugaaga gcaaaaggua aaauaccaaa 180
gagccauaga aggcgaacuu gcaagaacua uugagacuuu agaaccuauu cguagcgcug 240
uuguacacau agcauuuccu aaagauagug uuuuuaccga aaggcaaauu ccgccuacag 300
cuucaguugu uguuaauguu cgcgaaggcu uaaagcuuac uagaaaacaa auugauggua 360

<210> SEQ ID NO 50
<211> LENGTH: 360
<212> TYPE: RNA
<213> ORGANISM: Homo sapiens

<400> SEQUENCE: 50
uauaaauuag aaagugaaaa uaaaguuuua gucccuuugc cgccuuuucu augguaaaau 60
aucgucaaag aauguuuauu gcaagcgaag gucuuauaaa agauagucgc guggguuuug 120
aagcuuuuga uacucaagcu uuuggagcua caaaugaaga gcaaaaggua aaauaccaaa 180
gagccauaga aggcgaacuu gcaagaacua uugagacuuu agaaccuauu cguagcgcug 240
uuguacacau agcauuuccu aaagauagug uuuuuaccga aaggcaaauu ccgccuacag 300
cuucaguugu uguuaauguu cgcgaaggcu uaaagcuuac uagaaaacaa auugauggua 360

<210> SEQ ID NO 51
<211> LENGTH: 358
<212> TYPE: RNA
<213> ORGANISM: Homo sapiens

<400> SEQUENCE: 51
uauaaauuag aaagugaaaa uaaaguuuua gucccuuuaa auuucuuuau gguaaaauau 60
cgucaaagaa uguuuauugc aagcgaaggu cuuauaaaag auagucgcgu ggguuuugaa 120
gcuuuugaua cucaagcuuu uggagcuaca aaugaagagc aaaagguaaa auaccaaaga 180
gccauagaag gcgaacuugc aagaacuauu gagacuuuag aaccuauucg uagcgcuguu 240
guacacauag cauuuccuaa agauaguguu uuuaccgaaa ggcaaauucc gccuacagcu 300
ucaguuguug uuaauguucg cgaaggcuua aagcuuacua gaaaacaaau ugauggua 358

<210> SEQ ID NO 52
<211> LENGTH: 362
<212> TYPE: RNA
<213> ORGANISM: Homo sapiens

<400> SEQUENCE: 52
uauaaauuag aaagugaaaa uaaaguuuua gucccuuccu uuaaauuucu uuaugguaaa 60
auaucgucaa agaauguuua uugcaagcga aggucuuaua aaagauaguc gcgugggguuu 120 ugaagcuuuu gauacucaag cuuuuggagc uacaaaugaa gagcaaaagg uaaaauacca 180
aagagccaua gaaggcgaac uugcaagaac uauugagacu uuagaaccua uucguagcgc 240
uguuguacac auagcauuuc cuaaagauag uguuuuuacc gaaaggcaaa uuccgccuac 300
agcuucaguu guuguuaaug uucgcgaagg cuuaaagcuu acuagaaaac aaauugaugg 360
ua 362

<210> SEQ ID NO 53
<211> LENGTH: 358
<212> TYPE: RNA
<213> ORGANISM: Homo sapiens

<400> SEQUENCE: 53
uauaaauuag aaagugaaaa uaaaguuuua gucuuuuuaa auuucuuuau gguaaaauau 60
cgucaaagaa uguuuauugc aagcgaaggu cuuauaaaag auagucgcgu ggguuuugaa 120
gcuuuugaua cucaagcuuu uggagcuaca aaugaagagc aaaagguaaa auaccaaaga 180
gccauagaag gcgaacuugc aagaacuauu gagacuuuag aaccuauucg uagcgcuguu 240
guacacauag cauuuccuaa agauaguguu uuuaccgaaa ggcaaauucc gccuacagcu 300
ucaguuguug uuaauguucg cgaaggcuua aagcuuacua gaaaacaaau ugauggua 358

<210> SEQ ID NO 54
<211> LENGTH: 362
<212> TYPE: RNA
<213> ORGANISM: Homo sapiens

<400> SEQUENCE: 54
uauaaauuag aaagugaaaa uaaaguuuua gucccaauuu uuaaauuucu uuaugguaaa 60
auaucgucaa agaauguuua uugcaagcga aggucuuaua aaagauaguc gcgugggguuu 120 ugaagcuuuu gauacucaag cuuuuggagc uacaaaugaa gagcaaaagg uaaaauacca 180
aagagccaua gaaggcgaac uugcaagaac uauugagacu uuagaaccua uucguagcgc 240
uguuguacac auagcauuuc cuaaagauag uguuuuuacc gaaaggcaaa uuccgccuac 300
agcuucaguu guuguuaaug uucgcgaagg cuuaaagcuu acuagaaaac aaauugaugg 360
ua 362

<210> SEQ ID NO 55
<211> LENGTH: 60
<212> TYPE: RNA
<213> ORGANISM: Homo sapiens

<400> SEQUENCE: 55
uauaaauuag aaagugaaaa uaaaguuuua gucccuuuuu aaauuucuuu augguaaaau 60

<210> SEQ ID NO 56
<211> LENGTH: 110

<212> TYPE: RNA
<213> ORGANISM: Homo sapiens

<400> SEQUENCE: 56
caaguucuuc ugcugcaauu guagcuaaac uugaacaaaa uaauauuccc uauaaauuag 60
aaagugaaaa uaaaguuuua gucccuuuuu aaauuucuuu augguaaaau 110

<210> SEQ ID NO 57
<211> LENGTH: 210
<212> TYPE: RNA
<213> ORGANISM: Homo sapiens

<400> SEQUENCE: 57
auuauaguug ugguuggguu uuugguuuuu uuagcuuuau uucguggaag ugguaguaau 60
gcaaauaaug gauaugcagu uuuaguugaa aauguaagcc caaguucuuc ugcugcaauu 120
guagcuaaac uugaacaaaa uaauauuccc uauaaauuag aaagugaaaa uaaaguuuua 180
gucccuuuuu aaauuucuuu augguaaaau 210

<210> SEQ ID NO 58
<211> LENGTH: 1060
<212> TYPE: RNA
<213> ORGANISM: Homo sapiens

<400> SEQUENCE: 58
auggauuuag aaaauauccu agaaaauaau caaagcauag guuuauacca cccaaagaac 60
gaacacgaug ccugugguau cgcugcaguu gcuaauauac gcgguauugc uucuuauaag 120
guuauuugug augcuuuaga aauuuugaug aaucuugaac accgaggugg ugcaggagcu 180
gaagaaaauu caggugaugg ggcggggauu uuaauccaaa uuccacauga uuuuuuuaaa 240
acucaagaau uggguuuuga acuuccuaaa aagggugauu augcuguagc acagauguuu 300
uuaucaccca auacugaugc aaaagaagaa gcaaaagaaa uauuuuuaca agguuuaaag 360
gauaaaaaac uugaauuuuu agguuuuaga gaagugccuu uuaauccuag cgauauaggu 420
gcaagugcuu uaaaagcuau gccuuauuuu uuacaagccu uugugaaaaa accaaguaaa 480
auaagugcag gacuugaguu ugaaagagug cuuuauagua cgcgucgacu uauagaaaaa 540
agagcuauua augugccaaa auuuuauuuu ucaaguuuuu cuucacgcac cauaguuuau 600
aaaggaaugc uucuuucaac ucaauugagc gauuuuuauc uugauuuuaa agaugucaau 660
augaaaucag ccaucgcuuu ggugcauucu cgcuuuucga cuaauaccuu cccaaguugg 720
gaaagagccc auccaaaccg uuauauggug cauaauggag agauuaauac cauacgcgga 780
aauguugaua gcauaagagc uagagaaggc uugaugcaaa gugaguauuu ugaaaauuua 840
gaugaaauuu auuauaguug ugguuggguu uuugguuuuu uuagcuuuau uucguggaag 900
ugguaguaau gcaaauaaug gauaugcagu uuuaguugaa aauguaagcc caaguucuuc 960
ugcugcaauu guagcuaaac uugaacaaaa uaauauuccc uauaaauuag aaagugaaaa 1020
uaaaguuuua gucccuuuuu aaauuucuuu augguaaaau 1060

<210> SEQ ID NO 59
<211> LENGTH: 210
<212> TYPE: RNA
<213> ORGANISM: Homo sapiens

<400> SEQUENCE: 59
uauaaauuag aaagugaaaa uaaaguuuua gucccuuuuu aaauuucuuu augguaaaau 60

```
aucgucaaag aauguuuauu gcaagcgaag gucuuauaaa agauagucgc gugggguuuug    120

aagcuuuuga uacucaagcu uuuggagcua caaaugaaga gcaaaaggua aaauaccaaa    180

gagccauaga aggcgaacuu gcaagaacua                                      210


<210> SEQ ID NO 60
<211> LENGTH: 360
<212> TYPE: RNA
<213> ORGANISM: Homo sapiens

<400> SEQUENCE: 60

uauaaaauuag aaagugaaaa uaaaguuuua gucccuuuuu aaauuucuuu augguaaaau     60

aucgucaaag aauguuuauu gcaagcgaag gucuuauaaa agauagucgc gugggguuuug    120

aagcuuuuga uacucaagcu uuuggagcua caaaugaaga gcaaaaggua aaauaccaaa    180

gagccauaga aggcgaacuu gcaagaacua uugagacuuu agaaccuauu cguagcgcug    240

uuguacacau agcauuuccu aaagauagug uuuuuaccga aaggcaaauu ccgccuacag    300

cuucaguugu uguuaaaguu cgcgaaggcu uaaagcuuac uagaaaacaa auugauggua    360


<210> SEQ ID NO 61
<211> LENGTH: 1189
<212> TYPE: RNA
<213> ORGANISM: Homo sapiens

<400> SEQUENCE: 61

aauuuccuuc caagcuccau cuauaucaaa uucaagcucu guuccaucgc uaagauagac     60

uucauaggaa uuuuugucuu uuugcacgau cccuauaggc gcuuugaaau uauguuguaa    120

aaauucuuua gaaacauuug guaaauuauc agcagaaauu auuauaucag cauuuaaaga    180

uaaacuuaaa auaguaauaa uauuuaaaaa uuuaauuuuc aauauuuuuc cuaaaauuauu    240

uuuuaguaaa auuguaaaga auuuauguga auuuuaugug aauuuuaaga caauauuaua    300

aaaaauaaag guuuuauauu uugcuuacaa uuuuuuuaau uuuuuuaaau auuuuauguu    360

auuuuuugau uucuuaugau uauuacaaua uccuugguuu gaauauuuua uuuuuuaaug    420

gagcuuauug gcagcuuuua aguucaaugu uuuuacaugg aaauuuaacu caucuuauau    480

uaaaauaugau aguuuuguuu caauuugggc guauguuaga aacuuauuug ggugcuuugu    540

guuuuauuuu uauuuauuuu auuggcggau uguugugcuc acuuuuaagu guuuuuuaug    600

uguauuuuga uuuuaaauau uuuggagaaa auauaaaugu cauaggcgcu aguggugcaa    660

uuuguguuuu aaugggcuuu uaugcuguua uugauaaaaa uagcacaaaa ggacuuauag    720

uggcaauuuu acuuaugagu uuugugccau ugcuuauggg gauaaauguu gcuugguaug    780

gucauauuuu cggguuuaug ugugguuaua uuuuagcuaa aauaaaagag guaaaaugaa    840

aaaaauuuau auuauaagac augcaaaagc aaguaagagu gaagacaucg augauuuuga    900

aagaaagcuu acuaagagug gaaaggaaga uuuaaaaaaa cuuuuuaaaa aucuugcuuc    960

gcaugaaauu cauccugauu uggugcuauc aaguccugcu guuagaaccg cuaaaacagc   1020

gaaaaaaaua gccaaauuuu auaauuuuga uaaaaauaga auuuguuuug augaaagauu   1080

guaucuuugc aauguugaaa auuugcuaaa aauucugcaa gauauugaug augaguuuaa   1140

ugaaguauuu uuagugggguc auaaauccuag uuuaauggag cuuggagag              1189


<210> SEQ ID NO 62
<211> LENGTH: 72
<212> TYPE: RNA
<213> ORGANISM: Homo sapiens
```

<400> SEQUENCE: 62
ccaaauguuu cuaaagaauu uuuauaaaga guuugcggga cucugcgggg uuacaauccc 60
cuaaaaccgc uu 72

<210> SEQ ID NO 63
<211> LENGTH: 32
<212> TYPE: DNA
<213> ORGANISM: Homo sapiens

<400> SEQUENCE: 63
ctataggcgc tttgaaatta tgttagaaac ac 32

<210> SEQ ID NO 64
<211> LENGTH: 72
<212> TYPE: RNA
<213> ORGANISM: Homo sapiens

<400> SEQUENCE: 64
aaacuaucau auuuaauaua agaugaaaga guuugcggga cucugcgggg uuacaauccc 60
cuaaaaccgc uu 72

<210> SEQ ID NO 65
<211> LENGTH: 32
<212> TYPE: DNA
<213> ORGANISM: Homo sapiens

<400> SEQUENCE: 65
atgtttttac atggaaattt aactagaaac ac 32

<210> SEQ ID NO 66
<211> LENGTH: 72
<212> TYPE: RNA
<213> ORGANISM: Homo sapiens

<400> SEQUENCE: 66
caaaacucau aaguaaaauu gccauaaaga guuugcggga cucugcgggg uuacaauccc 60
cuaaaaccgc uu 72

<210> SEQ ID NO 67
<211> LENGTH: 32
<212> TYPE: DNA
<213> ORGANISM: Homo sapiens

<400> SEQUENCE: 67
aaaaatagca caaaaggact tataagaaac ac 32

<210> SEQ ID NO 68
<211> LENGTH: 72
<212> TYPE: RNA
<213> ORGANISM: Homo sapiens

<400> SEQUENCE: 68
aaaaguuuuu uuaaaucuuc cuuuuaaaga guuugcggga cucugcgggg uuacaauccc 60
cuaaaaccgc uu 72

<210> SEQ ID NO 69
<211> LENGTH: 32
<212> TYPE: DNA
<213> ORGANISM: Homo sapiens

<400> SEQUENCE: 69
ttgaaagaaa gcttactaag agtgagaaac ac 32

<210> SEQ ID NO 70
<211> LENGTH: 72
<212> TYPE: RNA
<213> ORGANISM: Homo sapiens

<400> SEQUENCE: 70
gcagaauuuu uagcaaauuu ucaauaaaga guuugcggga cucugcgggg uuacaauccc 60
cuaaaaccgc uu 72

<210> SEQ ID NO 71
<211> LENGTH: 32
<212> TYPE: DNA
<213> ORGANISM: Homo sapiens

<400> SEQUENCE: 71
gatgaaagat tgtatctttg caatagaaac ac 32

<210> SEQ ID NO 72
<211> LENGTH: 91
<212> TYPE: RNA
<213> ORGANISM: Homo sapiens

<400> SEQUENCE: 72
uuuacaacau aauuucaaag cgccuauaaa gugggauuaa ggcuaguccg uuaucaacuu 60
gaaaaagugg caccgagucg gugcuuuuuu u 91

<210> SEQ ID NO 73
<211> LENGTH: 23
<212> TYPE: DNA
<213> ORGANISM: Homo sapiens

<400> SEQUENCE: 73
gaatttttgt ctttttgcac cgg 23

<210> SEQ ID NO 74
<211> LENGTH: 91
<212> TYPE: RNA
<213> ORGANISM: Homo sapiens

<400> SEQUENCE: 74
aauaagcucc auuaaaaaau aaaauauuaa gucaaacuaa ggcuaguccg uuaucaacuu 60
gaaaaagugg caccgagucg gugcuuuuuu u 91

<210> SEQ ID NO 75
<211> LENGTH: 23
<212> TYPE: RNA
<213> ORGANISM: Homo sapiens

<400> SEQUENCE: 75
augauuauua caauauccuu cgg 23

<210> SEQ ID NO 76
<211> LENGTH: 91
<212> TYPE: RNA
<213> ORGANISM: Homo sapiens

<400> SEQUENCE: 76
ucaaaauaca cauaaaaaac acuuaaaaaa gugugaguaa ggcuaguccg uuaucaacuu 60
gaaaaagugg caccgagucg gugcuuuuuu u 91

<210> SEQ ID NO 77
<211> LENGTH: 23
<212> TYPE: DNA
<213> ORGANISM: Homo sapiens

<400> SEQUENCE: 77
ttttattggc ggattgttgt cgg 23

<210> SEQ ID NO 78
<211> LENGTH: 91
<212> TYPE: RNA
<213> ORGANISM: Homo sapiens

<400> SEQUENCE: 78
caugucuuau aauauaaauu uuuuucauaa guuuuacuaa ggcuaguccg uuaucaacuu 60
gaaaaagugg caccgagucg gugcuuuuuu u 91

<210> SEQ ID NO 79
<211> LENGTH: 23
<212> TYPE: DNA
<213> ORGANISM: Homo sapiens

<400> SEQUENCE: 79
attttagcta aaataaaaga cgg 23

<210> SEQ ID NO 80
<211> LENGTH: 91
<212> TYPE: RNA
<213> ORGANISM: Homo sapiens

<400> SEQUENCE: 80
aaauucuauu uuuaucaaaa uuauaaaaaa guuuugguaa ggcuaguccg uuaucaacuu 60
gaaaaagugg caccgagucg gugcuuuuuu u 91

<210> SEQ ID NO 81
<211> LENGTH: 23
<212> TYPE: DNA
<213> ORGANISM: Homo sapiens

<400> SEQUENCE: 81
ctaaaacagc gaaaaaaata cgg 23

<210> SEQ ID NO 82
<211> LENGTH: 88
<212> TYPE: RNA
<213> ORGANISM: Homo sapiens

<400> SEQUENCE: 82
aaccuuuauu uuuuauaaua uugucuagca aaauucauaa ggcuucaugc cgaaaucaac 60
acccugucau uuuauggcag gguguuuu 88

<210> SEQ ID NO 83
<211> LENGTH: 27
<212> TYPE: DNA
<213> ORGANISM: Homo sapiens

<400> SEQUENCE: 83
agaatttatg tgaattttat tgagaaa 27

<210> SEQ ID NO 84
<211> LENGTH: 88
<212> TYPE: RNA
<213> ORGANISM: Homo sapiens

<400> SEQUENCE: 84
aacuaucaua uuuaauauaa gaugagagcu aaauuucuaa ggcuucaugc cgaaaucaac 60
acccugucau uuuauggcag gguguuuu 88

<210> SEQ ID NO 85
<211> LENGTH: 27
<212> TYPE: DNA
<213> ORGANISM: Homo sapiens

<400> SEQUENCE: 85
taagttcaat gtttttacat tgagaaa 27

<210> SEQ ID NO 86
<211> LENGTH: 88
<212> TYPE: RNA
<213> ORGANISM: Homo sapiens

<400> SEQUENCE: 86
guaagcuuuc uuucaaaauc aucgauagcu cuucacuuaa ggcuucaugc cgaaaucaac 60
acccugucau uuuauggcag gguguuuu 88

<210> SEQ ID NO 87
<211> LENGTH: 27
<212> TYPE: DNA
<213> ORGANISM: Homo sapiens

<400> SEQUENCE: 87
agacatgcaa aagcaagtaa tgagaaa 27

<210> SEQ ID NO 88
<211> LENGTH: 88
<212> TYPE: RNA
<213> ORGANISM: Homo sapiens

<400> SEQUENCE: 88
gaagcaagau uuuuaaaaag uuuuuuagca aaucuucuaa ggcuucaugc cgaaaucaac 60
acccugucau uuuauggcag gguguuuu 88

<210> SEQ ID NO 89
<211> LENGTH: 27
<212> TYPE: DNA
<213> ORGANISM: Homo sapiens

<400> SEQUENCE: 89
aagcttacta agagtggaaa tgagaaa 27

<210> SEQ ID NO 90
<211> LENGTH: 88
<212> TYPE: RNA
<213> ORGANISM: Homo sapiens

<400> SEQUENCE: 90
uuuaucaaaa uuauaaaauu uggcuaagcu uuuuucguaa ggcuucaugc cgaaaucaac 60
acccugucau uuuauggcag gguguuuu 88

<210> SEQ ID NO 91
<211> LENGTH: 27
<212> TYPE: DNA
<213> ORGANISM: Homo sapiens

<400> SEQUENCE: 91
ctgttagaac cgctaaaaca tgagaaa 27

<210> SEQ ID NO 92
<211> LENGTH: 72
<212> TYPE: RNA
<213> ORGANISM: Homo sapiens

<400> SEQUENCE: 92
aaacuaucau auuuaaugug ugaugaaaga guuugcggga cucugcgggg uuacaauccc 60
cuaaaaccgc uu 72

<210> SEQ ID NO 93
<211> LENGTH: 1189
<212> TYPE: RNA
<213> ORGANISM: Homo sapiens

<400> SEQUENCE: 93
aauuuccuuc caagcuccau cuauaucaaa uucaagcucu guuccaucgc uaagauagac 60
uucauaggaa uuuuugucuu uuugcacgau cccuauaggc gcuuugaaau uauguuguaa 120
aaauucuuua gaaacauuug guaaauuauc agcagaaauu auuauaucag cauuuaaaga 180
uaaacuuaaa auaguaauaa uauuuaaaaa uuuaauuuuc aauauuuuuc cuaaauuauu 240
uuuuaguaaa auuguaaaga auuuauguga auuuuaugug aauuuuaaga caauauuaua 300
aaaaauaaag guuuuauauu uugcuuacaa uuuuuuuaau uuuuuuaaau auuuuauguu 360
auuuuuugau uucuuaugau uauuacaaua uccuugguuu gaauauuuua uuuuuuaaug 420
gagcuuauug gcagcuuuua aguucaaugu uuuuacaugg aaauuuaacu caucacacau 480
uaaauaugau aguuuuguuu caauuugggc guauguuaga aacuuauuug ggugcuuugu 540
guuuuauuuu uauuuauuuu auuggcggau uguugugcuc acuuuuaagu guuuuuuaug 600
uguauuuuga uuuuaaauau uuuggagaaa auauaaaugu cauaggcgcu aguggugcaa 660
uuuguguuuu aaugggcuuu uaugcuguua uugauaaaaa uagcacaaaa ggacuuauag 720
uggcaauuuu acuuaugagu uuugugccau ugcuuauggg gauaaauguu gcuugguaug 780
gucauauuuu cggguuuaug ugugguuaua uuuuagcuaa aauaaaagag guaaaaugaa 840
aaaaauuuau auuauaagac augcaaaagc aaguaagagu gaagacaucg augauuuuga 900
aagaaagcuu acuaagagug gaaaggaaga uuuaaaaaaa cuuuuuaaaa aucuugcuuc 960
gcaugaaauu cauccugauu uggugcuauc aaguccugcu guuagaaccg cuaaaacagc 1020
gaaaaaaaua gccaaauuuu auaauuuuga uaaaaauaga auuuguuuug augaaagauu 1080
guaucuuugc aauguugaaa auuugcuaaa aauucugcaa gauauugaug augaguuuaa 1140
ugaaguauuu uuaguggguc auaaauccuag uuuaauggag cuuggagag 1189

<210> SEQ ID NO 94
<211> LENGTH: 72
<212> TYPE: RNA
<213> ORGANISM: Homo sapiens

<400> SEQUENCE: 94
aaaaguuuuu uuaaaucgug uuuuuaaaga guuugcggga cucugcgggg uuacaauccc 60
cuaaaaccgc uu 72

<210> SEQ ID NO 95
<211> LENGTH: 1189
<212> TYPE: RNA
<213> ORGANISM: Homo sapiens

<400> SEQUENCE: 95
aauuuccuuc caagcuccau cuauaucaaa uucaagcucu guuccaucgc uaagauagac 60
uucauaggaa uuuuugucuu uuugcacgau cccuauaggc gcuuugaaau uauguuguaa 120
aaauucuuua gaaacauuug guaaauuauc agcagaaauu auuauaucag cauuuaaaga 180
uaaacuuaaa auaguaauaa uauuuaaaaa uuuaauuuuc aauauuuuuc cuaaauuauu 240
uuuuaguaaa auuguaaaga auuuauguga auuuuaugug aauuuuaaga caauauuaua 300
aaaaauaaag guuuuauauu uugcuuacaa uuuuuuuaau uuuuuuaaau auuuuauguu 360
auuuuuugau uucuuaugau uauuacaaua uccuugguuu gaauauuuua uuuuuuaaug 420
gagcuuauug gcagcuuuua aguucaaugu uuuuacaugg aaauuuaacu caucuuauau 480
uaaauaugau aguuuuguuu caauuugggc guauguuaga aacuuauuug ggugcuuugu 540
guuuuauuuu uauuuauuuu auuggcggau uguugugcuc acuuuuaagu guuuuuuaug 600
uguauuuuga uuuuaaauau uuuggagaaa auauaaaugu cauaggcgcu aguggugcaa 660
uuuguguuuu aaugggcuuu uaugcuguua uugauaaaaa uagcacaaaa ggacuuauag 720
uggcaauuuu acuuaugagu uuugugccau ugcuuauggg gauaaauguu gcuugguaug 780
gucauauuuu cggguuuaug ugugguuaua uuuuagcuaa aauaaaagag guaaaaugaa 840
aaaaauuuau auuauaagac augcaaaagc aaguaagagu gaagacaucg augauuuuga 900
aagaaagcuu acuaagagug gaaaacacga uuuaaaaaaa cuuuuuaaaa aucuugcuuc 960
gcaugaaauu cauccugauu uggugcuauc aaguccugcu guuagaaccg cuaaaacagc 1020
gaaaaaaaua gccaaauuuu auaauuuuga uaaaaauaga auuuguuuug augaaagauu 1080
guaucuuugc aauguugaaa auuugcuaaa aauucugcaa gauauugaug augaguuuaa 1140
ugaaguauuu uuagugggguc auaauccuag uuuaauggag cuuggagag 1189

<210> SEQ ID NO 96
<211> LENGTH: 678
<212> TYPE: DNA
<213> ORGANISM: Homo sapiens

<400> SEQUENCE: 96
atggagcttt tcactggcgt tgttcccatc ctggtcgagc tggacggcga cgtaaacggc 60
cacaagttca gcgtgtccgg cgagggcgag ggcgatgcca cctacggcaa gctgaccctg 120
aagttcatct gcaccaccgg caagctgccc gtgccctggc ccaccctcgt gaccaccctg 180
acctacggcg tgcagtgctt cagccgctac cccgaccaca tgaagcagca cgacttcttc 240
aagtccgcca tgcccgaagg ctacgtccag gagcgcacca tcttcttcaa ggacgacggc 300
aactacaaga cccgcgccga ggtgaagttc gagggcgaca ccctggtgaa ccgcatcgag 360
ctgaagggca tcgacttcaa ggaggacggc aacatcctgg ggcacaagct ggagtacaac 420
tacaacagcc acaacgtcta tatcatggcc gacaagcaga agaacggcat caaggtgaac 480
ttcaagatcc gccacaacat cgaggacggc agcgtgcagc tcgccgacca ctaccagcag 540
aacaccccca tcggcgacgg ccccgtgctg ctgcccgaca accactacct gagcacccag 600
tccgccctga gcaaagaccc caacgagaag cgcgatcaca tggtcctgct ggagttcgtg 660
accgccgccg ggatctaa 678

<210> SEQ ID NO 97
<211> LENGTH: 25
<212> TYPE: RNA
<213> ORGANISM: Homo sapiens

<400> SEQUENCE: 97
uaaaaucagg gaaaaauuua aagaa 25

<210> SEQ ID NO 98
<211> LENGTH: 12
<212> TYPE: RNA
<213> ORGANISM: Homo sapiens

<400> SEQUENCE: 98
guuuuagucc cu 12

<210> SEQ ID NO 99
<211> LENGTH: 12
<212> TYPE: RNA
<213> ORGANISM: Homo sapiens

<400> SEQUENCE: 99
agggacuaaa au 12

<210> SEQ ID NO 100
<211> LENGTH: 12
<212> TYPE: RNA
<213> ORGANISM: Homo sapiens

<400> SEQUENCE: 100
gcgccgaguu ag 12

<210> SEQ ID NO 101
<211> LENGTH: 12
<212> TYPE: RNA
<213> ORGANISM: Homo sapiens

<400> SEQUENCE: 101
cuaacucggc gc 12

<210> SEQ ID NO 102
<211> LENGTH: 27
<212> TYPE: DNA
<213> ORGANISM: Homo sapiens

<400> SEQUENCE: 102
taagttcaat gtttttacat tgagaaa 27

<210> SEQ ID NO 103
<211> LENGTH: 22
<212> TYPE: RNA
<213> ORGANISM: Homo sapiens

<400> SEQUENCE: 103
agaauuuaug ugaauuuuau ug 22

<210> SEQ ID NO 104
<211> LENGTH: 29
<212> TYPE: DNA
<213> ORGANISM: Homo sapiens

<400> SEQUENCE: 104
agaatttatg tgaattttat tgtgagaaa 29

<210> SEQ ID NO 105
<211> LENGTH: 27
<212> TYPE: DNA
<213> ORGANISM: Homo sapiens

<400> SEQUENCE: 105
cgtccaggag cgcaccatct tgagaaa 27

<210> SEQ ID NO 106
<211> LENGTH: 27
<212> TYPE: DNA
<213> ORGANISM: Homo sapiens

<400> SEQUENCE: 106
ctaccagcag aacaccccca tgagaaa 27

<210> SEQ ID NO 107
<211> LENGTH: 36
<212> TYPE: RNA
<213> ORGANISM: Homo sapiens

<400> SEQUENCE: 107
ucuucaagga cgacggcaac uacaagaccc gcgccg 36

<210> SEQ ID NO 108
<211> LENGTH: 36
<212> TYPE: RNA
<213> ORGANISM: Homo sapiens

<400> SEQUENCE: 108
ucggcgacgg ccccgugcug cugcccgaca accacu 36

<210> SEQ ID NO 109
<211> LENGTH: 27
<212> TYPE: DNA
<213> ORGANISM: Homo sapiens

<400> SEQUENCE: 109
ttatcgaacc gaaaccgcaa tgagaaa 27

<210> SEQ ID NO 110
<211> LENGTH: 27
<212> TYPE: DNA
<213> ORGANISM: Homo sapiens

<400> SEQUENCE: 110
ggcggtcgtg aaggttacga tgagaaa 27

<210> SEQ ID NO 111
<211> LENGTH: 122
<212> TYPE: RNA
<213> ORGANISM: Homo sapiens

<400> SEQUENCE: 111
ggcgcguuua uuccauuacu uuggagccag ucccagcgac uaugucguau ggacgaagcg 60
cuuauuuauc ggagagaaac cgauaaguaa aacgcaucaa aguccugcag cagaaaauca 120
aa 122

<210> SEQ ID NO 112
<211> LENGTH: 121
<212> TYPE: RNA
<213> ORGANISM: Homo sapiens

<400> SEQUENCE: 112
ggcgcguuua uuccauuacu uuggagccag ucccagcgac uaugucguau ggacgaagcg 60
cuuacuuauc ggagagaaac cgauaaguaa gcgcaucaaa guccugcagc agaaaaucaa 120
a 121

<210> SEQ ID NO 113
<211> LENGTH: 121
<212> TYPE: RNA
<213> ORGANISM: Homo sapiens

<400> SEQUENCE: 113
ggcgcguuua uuccauuacu uuggagccag ucccagcgac uaugucguau ggacgaauau 60
gcuacuuauc ggagagaaac cgauaaguag cauaaucaaa guccugcagc agaaaaucaa 120
a 121

<210> SEQ ID NO 114
<211> LENGTH: 121
<212> TYPE: RNA
<213> ORGANISM: Homo sapiens

<400> SEQUENCE: 114
ggcgcguuua uuccauuacu uuggagccag ucccagcgac uaugucguau ggacgaagcg 60
cuguucgauc ggagagaaac cgaucgaaca gcgcaucaaa guccugcagc agaaaaucaa 120
a 121

<210> SEQ ID NO 115
<211> LENGTH: 121
<212> TYPE: RNA
<213> ORGANISM: Homo sapiens

<400> SEQUENCE: 115
ggcgcguuua uuccauuacu uuggagccag ucccagcgac uaugucguau ggacgaagcg 60
cuuacuuucg gaagagaaau ccgaaaguaa gcgcaucaaa guccugcagc agaaaaucaa 120
a 121

<210> SEQ ID NO 116
<211> LENGTH: 121
<212> TYPE: RNA
<213> ORGANISM: Homo sapiens

<400> SEQUENCE: 116
ggcgcguuua uuccauuacu uuggagccag ucccagcgac uaugucguau ggacgaauau 60
gcguucgucg gaagagaaau ccgacgaacg cauaaucaaa guccugcagc agaaaaucaa 120
a 121

<210> SEQ ID NO 117
<211> LENGTH: 121
<212> TYPE: RNA
<213> ORGANISM: Homo sapiens

<400> SEQUENCE: 117
ggcgcuuuua uuccauuauu uuugagccag ucccagcgac uaugucguau ggacgaagcg 60
cuuacuuauc ggagagaaac cgauaaguaa gcgcacaaaa auccugcagc agaaaaucaa 120
a 121

<210> SEQ ID NO 118
<211> LENGTH: 121
<212> TYPE: RNA
<213> ORGANISM: Homo sapiens

<400> SEQUENCE: 118
ggcgcauuua uuccauuaau uuagagccag ucccagcgac uaugucguau ggacgaagcg 60
cuuacuuauc ggagagaaac cgauaaguaa gcgcaguaaa uuccugcagc agaaaaucaa 120
a 121

<210> SEQ ID NO 119
<211> LENGTH: 121
<212> TYPE: RNA
<213> ORGANISM: Homo sapiens

<400> SEQUENCE: 119
ggcgcuuuca uuccauuauc uuugagccag ucccagcgac uaugucguau ggacgaagcg 60
cuuacuuauc ggagagaaac cgauaaguaa gcgcacaaag auccugcagc agaaaaucaa 120
a 121

<210> SEQ ID NO 120
<211> LENGTH: 59
<212> TYPE: RNA
<213> ORGANISM: Homo sapiens

<400> SEQUENCE: 120
guccaagaaa aaagaaauga uacgaggcau uagcacgaaa uuauuauauc agcauuuaa 59

<210> SEQ ID NO 121
<211> LENGTH: 104
<212> TYPE: RNA
<213> ORGANISM: Homo sapiens

<400> SEQUENCE: 121
guucugucuu uuggucagga caaccgucua gcuauaagug cugcagggug ugagaaacuc 60
cuauugcugg acgaugucuc uuuuauuucu uuuuucuugg aucu 104

<210> SEQ ID NO 122
<211> LENGTH: 58
<212> TYPE: RNA
<213> ORGANISM: Homo sapiens

<400> SEQUENCE: 122
guccaagaaa aaagaaauga aagaggcauu agcacgaaau uauuauauca gcauuuaa 58

<210> SEQ ID NO 123
<211> LENGTH: 19
<212> TYPE: RNA
<213> ORGANISM: Homo sapiens

<400> SEQUENCE: 123
uccaagaaaa aagaaauga 19

<210> SEQ ID NO 124
<211> LENGTH: 19
<212> TYPE: RNA
<213> ORGANISM: Homo sapiens

```
<400> SEQUENCE: 124

uuauuucuuu uuucuugga                                                 19


<210> SEQ ID NO 125
<211> LENGTH: 19
<212> TYPE: RNA
<213> ORGANISM: Homo sapiens

<400> SEQUENCE: 125

cuguacuauc gauuucagu                                                 19


<210> SEQ ID NO 126
<211> LENGTH: 19
<212> TYPE: RNA
<213> ORGANISM: Homo sapiens

<400> SEQUENCE: 126

acugaaaucg auaguacag                                                 19


<210> SEQ ID NO 127
<211> LENGTH: 18
<212> TYPE: RNA
<213> ORGANISM: Homo sapiens

<400> SEQUENCE: 127

acguuaaugc uuaagcua                                                  18


<210> SEQ ID NO 128
<211> LENGTH: 19
<212> TYPE: RNA
<213> ORGANISM: Homo sapiens

<400> SEQUENCE: 128

uagcuuaagc auuaacguc                                                 19
```

RNA DETECTION AND TRANSCRIPTION-DEPENDENT EDITING WITH REPROGRAMMED TRACRRNAS

CROSS REFERENCE TO RELATED APPLICATIONS

This application is a National Stage Application of International Application Number PCT/EP2021/055060, filed Mar. 1, 2021; which claims priority to European Patent Application No. 20160004.6, filed Feb. 28, 2020.

The Sequence Listing for this application is labeled "SeqList-19Aug22-ST25.txt", which was created on Aug. 19, 2022 and is 38 KB. The entire content is incorporated herein by reference in its entirety.

The present invention relates to methods for detecting at least one sensed RNA in a cell, tissue, and/or sample using at least one non-naturally occurring tracrRNA specifically hybridizing with said sensed RNA and at least one tracrRNA-dependent CRISPR nuclease enzyme binding to at least one target nucleic acid, as well as respective systems and diagnostic and therapeutic uses thereof.

BACKGROUND OF THE INVENTION

Almost all archaea and about half of bacteria possess clustered regularly interspaced short palindromic repeat (CRISPR)-CRISPR-associated genes (Cas) adaptive immune systems, which protect prokaryotes against viruses and other foreign invaders with nucleic-acid genomes. The CRISPR-Cas system is functionally divided into classes 1 and 2 according to the composition of the effector complexes. Class 2 consists of a single-effector nuclease, and routine practice of genome editing has been achieved by the exploitation of Class 2 CRISPR-Cas systems, which include the type II, V, and VI CRISPR-Cas systems. Types II and V can be used for targeting DNA or RNA, while type VI is employed for targeting RNA (see, for example, Koonin E V and Makarova K S Origins and evolution of CRISPR-Cas systems *Philos Trans R Soc Lond B Biol Sci.* 2019 May 13; 374(1772):20180087). Types II and V Cas effector nucleases commonly rely on protospacer-adjacent motifs (PAMs) as the first step in target DNA recognition, and the effector nucleases directly bind the PAM sequence through protein-DNA interactions and subsequently unzip the downstream DNA sequence. The effector proteins then interrogate the extent of base pairing between one strand of the DNA target and the guide portion of the CRISPR RNA (crRNA). Sufficient complementarity between the two drives target cleavage. PAM sequences are known to vary considerably not only between systems but also between otherwise similar nucleases, and it was shown that Cas proteins can be engineered to alter PAM recognition (Leenay and Beisel Deciphering, Communicating, and Engineering the CRISPR PAM. *J Mol Biol.* 2017 Jan. 20; 429(2):177-191). In addition to targeting DNA, some Type II and V single-effector nucleases such as the *C. jejuni* Cas9, the *N. meningitidis* Cas9, the *S. aureus* Cas9, and the Cas12f1 from an uncultured archaeon have also been shown to target ssDNA and/or RNA (RNA-dependent RNA targeting by CRISPR-Cas9. Elife. 2018; 7:e32724; DNase H Activity of *Neisseria meningitidis* Cas9. *Mol Cell.* 2015; 60(2):242-255; Programmed DNA destruction by miniature CRISPR-Cas14 enzymes). In these cases, no PAM was required. Some nucleases such as the *S. pyogenes* Cas9 (SpyCas9) were not able to immediately target ssDNA or RNA, although providing an oligonucleotide to generate a double-stranded PAM region allowed SpyCas9 to bind the single-stranded target and cleave it (Programmable RNA recognition and cleavage by CRISPR/Cas9. *Nature.* 2014; 516(7530):263-266).

Mature crRNAs are key elements in CRISPR-Cas defense against genome invaders. These short RNAs contain unique guide sequences that guide the Cas protein(s) to the cognate invading nucleic acids for their destruction. The CRISPR RNAs (crRNAs) are naturally encoded in CRISPR arrays comprising alternating conserved repeats and spacers. The array is often transcribed into a long pre-crRNA, and then this RNA is processed into the individual crRNAs composed of a portion of a repeat-spacer unit.

Different types of CRISPR-Cas systems have evolved distinct crRNA maturation mechanisms. A number of subtypes (II-A, II-B, II-C, V-B, V-C, etc.) have evolved a unique crRNA biogenesis pathway, in which a trans-activating CRISPR RNA (tracrRNA, encoded within the CRISPR-Cas locus) base pairs with each repeat sequence of the pre-crRNA to form a double-stranded RNA duplex (Evolutionary classification of CRISPR-Cas systems: a burst of class 2 and derived variants. *Nat Rev Microbiol.* 2020; 18(2):67-83). The crRNA-tracrRNA duplex is cleaved by the housekeeping endoribonuclease RNase III and is bound by the single-effector nuclease specific to the system. The nuclease then uses the crRNA within the RNA duplex to guide DNA and, in some cases, RNA targeting. To-date, multiple tracrRNA-dependent CRISPR nucleases have been reported, including Cas9, Cas12b1/C2c1, Cas12b2, Cas12e/CasX, Cas12f1/Cas14a, Cas12g, and Cas12k. The Cas12k nucleases are unique because they work in concert with a set of transposon genes for RNA-directed insertion of a DNA template (RNA-guided DNA insertion with CRISPR-associated transposases. Science. 2019; 365(6448):48-53). In each of these cases, the tracrRNA:crRNA duplex, when engineered as a single RNA chimera called a single-guide RNA (sgRNA), also directs sequence-specific dsDNA cleavage by Cas9 and other tracrRNA-dependent CRISPR nucleases (see Jinek, M. et al. A programmable dual-RNA-guided DNA endonuclease in adaptive bacterial immunity. *Science* 337, 816-821 (2012); Engineering of CRISPR-Cas12b for human genome editing. *Nat Commun.* 2019; 10(1):212).

The CRISPR-Cas9 system of *Francisella novicida* exhibits a PAM-dependent interaction of Cas9 with its endogenous DNA targets that is dependent on a non-canonical small CRISPR-associated RNA (scaRNA) and tracrRNA. Naturally, the scaRNA appears to direct Cas9 to genomic DNA targets with partial complementarity, resulting in transcriptional repression. scaRNA can be reprogrammed to repress other genes, and with engineered, extended complementarity to an exogenous target, can also direct DNA cleavage (Catalytically Active Cas9 Mediates Transcriptional Interference to Facilitate Bacterial Virulence *Mol Cell.* 2019 Aug. 8; 75(3):498-510.e5). Given that the scaRNA is encoded within the CRISPR-Cas system similar to crRNAs, the only previously known source of RNAs that could guide the CRISPR nucleases to its intended targets would only come from within the CRISPR-Cas system.

In a recent publication of the inventors (CRISPR RNA-Dependent Binding and Cleavage of Endogenous RNAs by the *Campylobacter jejuni* Cas9. *Mol Cell.* 2018; 69(5):893-905.e7), they sequenced RNAs that co-immunoprecipitated with the Cas9 nuclease of *Campylobacter jejuni* (CjeCas9), which had revealed a subset of RNAs that exhibited complementarity to the guide portion of the crRNAs encoded within the CRISPR locus of this bacterium. The inventors performed a similar co-immunoprecipitation experiment in a separate strain of *C. jejuni*. The resulting unpublished dataset included a set of RNAs that did not exhibit complementarity to the crRNA and instead shared complementarity to the anti-repeat portion of the tracrRNA (FIG. 1). The composition and size of these RNAs resembled that of crRNAs. These insights suggested that mature crRNAs (which guide Cas9 to their target) could be derived from messenger RNAs and other RNAs (e.g. ribosomal RNAs, transfer RNAs, small RNAs, antisense RNAs, small nucleolar RNAs, microRNAs, piwiRNAs, long non-coding RNAs, spliced introns, circular RNAs) besides those encoded by CRISPR arrays. In the context of the present invention, these RNAs are designated and/or referred to as non-canonical crRNAs (ncrRNAs).

Figure 2:
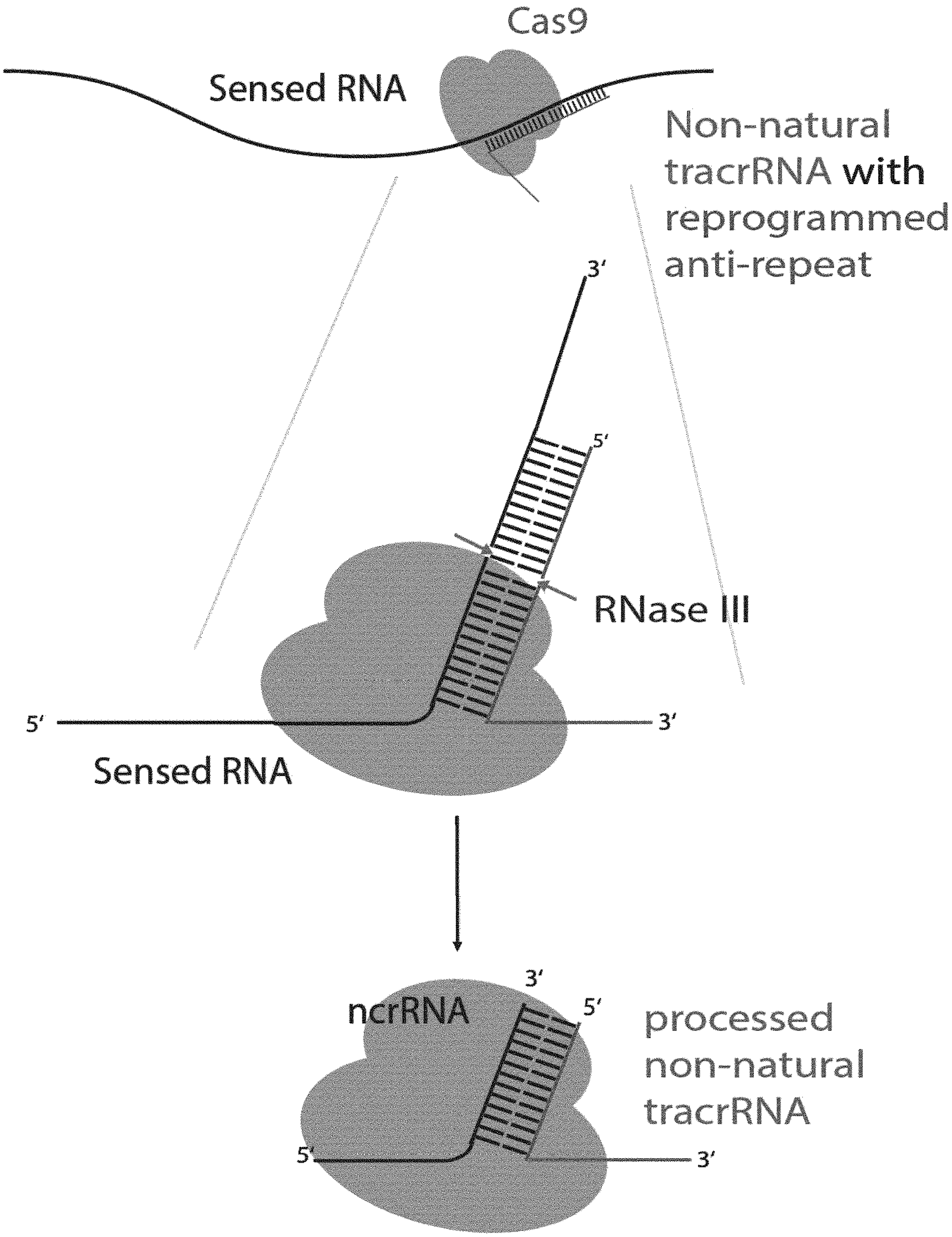

Base pairing between the CRISPR repeat and the tracrRNA anti-repeat form the RNA duplex bound by tracrRNA-dependent CRISPR nucleases. The exact secondary structure of duplex varies, with some duplexes exhibiting perfect complementarity while others contain characteristic bulges. Regardless of the exact secondary structure, maintaining this secondary structure as part of sgRNAs for the Cas9 from *Streptococcus pyogenes* allowed for modification of the sequence of this region of the sgRNAs (Guide RNA functional modules direct Cas9 activity and orthogonality. *Mol Cell.* 2014; 56(2):333-339). The inventors therefore hypothesized that the sequence of the anti-repeat portion of the tracrRNA could be changed to be complementary to other RNAs, allowing this portion of each RNA to become a mature crRNA (FIG. 2).

The concept of altering the anti-repeat region of the tracrRNA remains to be been explored, particularly for converting any RNA into an ncrRNA. The region downstream of the anti-repeat region has been modified in the context of sgRNAs and shown to be accommodate some changes without disrupting the function of the sgRNA (Guide RNA functional modules direct Cas9 activity and orthogonality. Mol Cell. 2014; 56(2):333-339). Furthermore, Scott, T. et al (Improved Cas9 activity by specific modifications of the tracrRNA. Sci Rep. 2019; 9(1):16104) showed that a region outside of the anti-repeat region could be changed to improve the overall editing activity exhibited by a Cas9 RNP, although the mechanism was unclear. However, these regions are involved in recognition by Cas9 and are not involved in pairing with a crRNA or any other RNA.

WO 2019/126037 relates to compositions and methods that utilize a nucleic acid sequence that has a genetically modified trans-activating crRNA (tracrRNA) sequence, where at least one uracil nucleotide of the tracrRNA sequence is replaced with a nucleotide other than uracil, and/or a nucleic acid sequence that has a guide RNA (gRNA) sequence wherein one or more cytosine nucleotides and/or one or more uracil nucleotides of said gRNA sequence are modified nucleotides. Disclosed is a composition further comprising an RNA-guided DNA endonuclease enzyme, such as Cas9 or Cpf1 or a Class II CRISPR endonuclease or a variant thereof, such as deactivated Cas9 (dCas9) or mutated Cas9 nickase (D10A).

US 2019/032053 relates to compositions comprising synthetic two-part aptamer-containing guide RNAs and methods of using said synthetic two-part aptamer-containing guide RNAs with CRISPR/Cas activator systems. Methods for targeted transcription activation, targeted transcription repression, targeted epigenome modification, targeted genome modification, or targeted genomic locus visualization in a eukaryotic cell are claimed.

WO 2019/183000 discloses chemically modified crRNAs and tracrRNAs, crRNAs and tracrRNAs with 5' and/or 3' conjugated moieties, and crRNAs and tracrRNAs with modifications in the repeat region of the crRNA or the anti-repeat region of the tracrRNA. Methods of using the crRNAs and tracrRNAs for genome editing with a CRISPR nuclease and kits for performing the same are also provided. crRNA and tracrRNA were chemically modified while retaining the efficacy of SpyCas9-based genome editing in cultured human cells.

Tautvydas Karvelis et al. (in: crRNA and tracrRNA guide Cas9-mediated DNA interference in *Streptococcus* thermophiles. RNA BIOLOGY, vol. 10, no. 5, 27 Mar. 2013, pages 841-851, DOI: 10.4161/rna24203), disclose that the Cas9-crRNA complex of the *Streptococcus thermophilus* DGCC7710 CRISPR3-Cas system functions as an RNA-guided endonuclease with crRNA-directed target sequence recognition and protein-mediated DNA cleavage. An additional RNA molecule, tracrRNA (trans-activating CRISPR RNA), co-purifies with the Cas9 protein isolated from the heterologous *E. coli* strain carrying the *S. thermophilus* DGCC7710 CRISPR3-Cas system. tracrRNA is required for Cas9-mediated DNA interference both in vitro and in vivo, and Cas9 specifically promotes duplex formation between the precursor crRNA (pre-crRNA) transcript and tracrRNA, in vitro. Furthermore, the housekeeping RNase III contributes to primary pre-crRNA-tracrRNA duplex cleavage for mature crRNA biogenesis. RNase III, however, is not required in the processing of a short pre-crRNA transcribed from a minimal CRISPR array containing a single spacer. An in vitro-assembled ternary Cas9-crRNA-tracrRNA complex cleaves DNA. The reference further specifies the molecular basis for crRNA-based re-programming of Cas9 to specifically cleave any target DNA sequence for precise genome surgery. The processes for crRNA maturation and effector complex assembly as disclosed are said to contribute to the further development of the Cas9 re-programmable system for genome editing applications.

Nevertheless, WO 2019/126037, US 2019/032053, WO 2019/183000, and Tautvydas Karvelis et al. all modify tracrRNAs as part of a standard crRNA:tracrRNA duplex used for DNA targeting. The references try to improve the existing duplex reflecting a truncated crRNA and tracrRNA, whereas the present invention uses modified non-naturally occurring tracrRNA to hybridize to naturally occurring RNAs that are not crRNAs.

The ability to generate an ncrRNA from any RNA links the presence of an RNA to an active tracrRNA-dependent CRISPR nuclease guided to specific targets by the ncrRNA. Therefore, reprogramming tracrRNAs holds the potential to sense specific RNA transcripts through sequence-specific targeting activity. This link is distinct from the two other CRISPR technologies used for nucleic acid detection that are based on Cas12a and Cas13. Specifically, Chen et al. (CRISPR-Cas12a target binding unleashes indiscriminate single-stranded DNase activity. Science. 2018; 360(6387): 436-439) disclose that RNA-guided DNA binding unleashes indiscriminate single-stranded DNA (ssDNA) cleavage activity by Cas12a that completely degrades ssDNA molecules. Combining Cas12a ssDNase activation with isothermal amplification created a method termed "DNA endonuclease-targeted CRISPR trans reporter" (DETECTR). Separately, Abudayyeh et al. (C2c2 is a single-component programmable RNA-guided RNA-targeting CRISPR effector. Science. 2016; 353(6299):aaf5573) demonstrated the RNA-guided RNase activity of the putative type VI CRISPR-effector LshC2c2 (now Cas13a). Gootenberg et al. (Nucleic acid detection with CRISPR-Cas13a/C2c2. Science. 2017 Apr. 28; 356(6336):438-442) further disclose that this "collateral effect" could be used to establish a CRISPR-based diagnostic (CRISPR-Dx), providing rapid DNA or RNA detection with attomolar sensitivity and single-base mismatch specificity. This Cas13a-based molecular detection platform, termed Specific High-Sensitivity Enzymatic Reporter UnLOCKing (SHERLOCK), has been used to detect specific strains of Zika and Dengue virus, distinguish pathogenic bacteria, genotype human DNA, and identify mutations in cell-free tumor DNA. While both technologies can output the presence of a detected nucleic acid, they both rely on non-specific nuclease activity as the output. In contrast, the present invention relies on a sequence-specific nuclease activity dictated by the sensed RNA.

It is an object of the present invention to apply the above advancements in CRISPR in the field of molecular diagnostics, in particular for detecting certain RNAs. Other objects and advantages will become apparent upon further studying the present specification with reference to the accompanying examples.

In a first aspect thereof, the object of the present invention is solved by providing a method for detecting at least one sensed RNA in a cell, tissue, and/or sample, said method comprising: a) contacting said sample with at least one non-naturally occurring tracrRNA comprising a portion that specifically hybridizes with a first portion of said sensed RNA, wherein a second portion of said sensed RNA specifically hybridizes with at least one target nucleic acid; wherein said at least one non-naturally occurring tracrRNA is hybridized or is able to be hybridized with said sensed RNA in the presence of at least one tracrRNA-dependent CRISPR nuclease enzyme, optionally further comprising the presence of a dsRNA-cleaving enzyme; b) detecting binding of said at least one tracrRNA-dependent CRISPR nuclease enzyme to said at least one target nucleic acid; c) wherein said binding detects said at least one sensed RNA in said cell, tissue and/or sample.

In a second aspect thereof, the object of the present invention is solved by providing a method_for detecting at least one sensed RNA in a cell and/or sample, said method comprising: a) contacting said sample with at least one non-naturally occurring tracrRNA comprising a portion that specifically hybridizes with a first portion of said sensed RNA, wherein a second portion of said sensed RNA specifically hybridizes with at least one target nucleic acid; wherein said at least one non-naturally occurring tracrRNA is hybridized or is able to be hybridized with said sensed RNA in the presence of at least one tracrRNA-dependent CRISPR nuclease enzyme, optionally further comprising the presence of a dsRNA-cleaving enzyme; b) detecting cleavage of said at least one target nucleic acid in said sample by said nuclease enzyme; c) wherein detecting said cleavage of at least one target nucleic acid detects said at least one sensed RNA in said cell, tissue and/or sample.

In a third aspect thereof, the object of the present invention is solved by providing a method for detecting at least one sensed RNA in a cell, tissue and/or sample, said method comprising: a) contacting said sample with at least one non-naturally occurring tracrRNA comprising a portion that specifically hybridizes with a first portion of said sensed RNA, wherein a second portion of said sensed RNA specifically hybridizes with at least one target nucleic acid; wherein said least one non-naturally occurring tracrRNA is hybridized or is able to be hybridized with said sensed RNA in the presence of at least one tracrRNA-dependent CRISPR nuclease enzyme, optionally further comprising the presence of a dsRNA-cleaving enzyme; and b) nicking or cleaving of said at least one target nucleic acid in said sample by said nuclease, c) detectably editing said at least one target nucleic acid comprising, for example, non-homologous end joining (NHEJ) repair, microhomology-mediated end joining (MMEJ), homologous-directed repair (HDR), prime editing, base editing, or RNA editing, and d) suitably detecting said editing of said at least one target nucleic acid comprising, for example, at least one method selected from detecting the presence and/or length of indels or gene edits, the activation/repression of a gene or other genetic element as encoded by said at least one target nucleic acid, and/or the detection of said prime or base editing; e) wherein detecting at least one edited target nucleic acid detects said at least one sensed RNA in said cell, tissue and/or sample.

In a preferred embodiment of the present invention, the above methods can be combined, e.g. the at least one sensed RNA in said cell, tissue and/or sample can be detected based on binding, cleavage and/or editing of said at least one nucleic acid DNA.

In a fourth aspect thereof, the object of the present invention is solved by providing a method for detecting a medical condition in a mammal, wherein said condition is related to the presence of, expression of and/or mutation(s) in at least one sensed RNA, comprising performing the method according to any of the aspects as above, and detecting said medical condition based on the presence of, expression of and/or mutation(s) in said at least one sensed RNA as detected.

In a fifth aspect thereof, the object of the present invention is solved by providing a detection system for a sensed RNA comprising a) a non-naturally occurring tracrRNA designed to bind to at least one portion of said sensed RNA, said sensed RNA further comprising a portion that specifically hybridizes with a first portion of a target nucleic acid, and b) at least one tracrRNA-dependent CRISPR nuclease enzyme.

In a sixth aspect thereof, the object of the present invention is solved by providing a non-naturally occurring tracrRNA nucleic acid molecule, comprising an anti-repeat region sequence that is designed to specifically hybridize to a preselected sensed RNA sequence through forming a complex that mimics the natural crRNA:tracrRNA duplex. The non-naturally occurring tracrRNA nucleic acid molecule may be part of a complex comprising the non-naturally occurring tracrRNA nucleic acid molecule according to the present invention, at least one tracrRNA-dependent CRISPR nuclease enzyme, and at least one sensed RNA, and may be further bound to a target DNA nucleic acid molecule comprising a sequence based or designed based on the at least one sensed RNA sequence.

In a seventh aspect thereof, the object of the present invention is solved by providing the use of the non-naturally occurring tracrRNA nucleic acid molecule or sensed RNA detection system according to the aspect as above for performing a method according to any of the aspects as above, in particular for detecting a sensed RNA, a viral sensed RNA, a sensed RNA transcribed from a disease marker, or for generating an expression profile for one or more sensed RNAs.

In the first aspect thereof, the object of the present invention is solved by providing a method for detecting at least one sensed RNA in a cell, tissue, and/or sample, said method comprising: a) contacting said sample with at least one non-naturally occurring tracrRNA comprising a portion that specifically hybridizes with a first portion of said sensed RNA, wherein a second portion of said sensed RNA specifically hybridizes with at least one target nucleic acid; wherein said at least one non-naturally occurring tracrRNA is hybridized or is able to be hybridized with said sensed RNA in the presence of at least one tracrRNA-dependent CRISPR nuclease enzyme, optionally further comprising the presence of an RNA-cleaving enzyme, such as RNase III; b) detecting binding of said at least one tracrRNA-dependent CRISPR nuclease enzyme to said at least one target nucleic acid; c) wherein said binding detects said at least one sensed RNA in said cell, tissue and/or sample.

In this first aspect of the present invention, the detection of said at least one sensed RNA in said cell, tissue and/or sample relies on the detection of binding of said at least one tracrRNA-dependent CRISPR nuclease enzyme to said at least one target nucleic acid. The Cas enzymes bind target nucleic acid independently of their ability to cleave target nucleic acid, and this flexibility is used in order to detect said at least one sensed RNA based on said binding activity.

Binding of said at least one tracrRNA-dependent CRISPR nuclease enzyme to said at least one target nucleic acid can be detected by any suitable detection method as known to the person of skill, and may include chromatin immunoprecipitation (ChIP) methods using an antibody against the nuclease and PCR primers for the DNA sequence of interest. The antibody is used to selectively precipitate the protein-DNA complex from the other genomic DNA fragments and protein-DNA complexes. The PCR primers allow specific amplification and detection of the target nucleic acid sequence. Quantitative PCR (qPCR) technique allows the amount of target nucleic acid sequence to be quantified. The ChIP assay is amenable to array-based formats (ChIP-on-chip) or direct sequencing of the DNA captured by the immunoprecipitated protein (ChIP-seq).

Other methods comprise DNA electrophoretic mobility shift assays (EMSA), or pull-down assays that are used to selectively extract a protein-DNA complex from a sample. Typically, the pull-down assay uses a DNA probe labeled with a high affinity tag, such as biotin, which allows the probe to be recovered or immobilized. A biotinylated DNA probe can be complexed with a protein from a cell lysate in a reaction similar to that used in the EMSA and then used to purify the complex using agarose or magnetic beads. The proteins are then eluted from the DNA and detected by western blot or identified by mass spectrometry. Alternatively, the protein may be labeled with an affinity tag, or the DNA-protein complex may be isolated using an antibody against the protein of interest (similar to a supershift assay). In this case, the unknown DNA sequence bound by the protein is detected by Southern blotting, PCR analysis, or sequencing analysis. A hybrid of the DNA pull-down assay and enzyme-linked immunosorbent assay (ELISA), the microplate capture assay, can be used that involves immobilized DNA probes to capture specific protein-DNA interactions and confirm protein identities and relative amounts with target-specific antibodies. Also, reporter assays can be used that provide a real-time in vivo readout of translational activity for a promoter of interest that may be blocked or induced by binding of the nuclease. Reporter genes are fusions of a target promoter DNA sequence and a reporter gene DNA sequence. The promoter DNA sequence is customized by the researcher and the reporter gene DNA sequence codes for a protein with detectable properties such as firefly luciferase, Renilla luciferase, alkaline phosphatase, or green fluorescent protein. These genes produce enzymes only when the promoter of interest is activated. The enzyme, in turn, fluoresces or catalyzes a substrate to produce either light, a color change, or other reaction that can be detected by spectroscopic instrumentation. The signal from the reporter gene is used as an indirect determinant for the transcription or translation of endogenous proteins driven from the same promoter.

In an embodiment of this aspect of the present invention, preferably the at least one tracrRNA-dependent CRISPR nuclease enzyme is inactivated, at least substantially, in its cleaving activity. For example, both the RuvC and HNH nuclease domains can be rendered inactive by point mutations (e.g. D10A and H840A in *S. pyogenes* Cas9 (SpCas9)), resulting in a nuclease dead Cas9 (dCas9) molecule that cannot cleave target nucleic acid. Nevertheless, the dCas9 molecule retains the ability to bind to target DNA based on the sgRNA targeting sequence. In the case of single-stranded targets, disruption of the HNH domain would be sufficient to prevent cleavage but not binding (CRISPR RNA-Dependent Binding and Cleavage of Endogenous RNAs by the *Campylobacter jejuni* Cas9. Mol Cell. 2018; 69(5):893-905.e7). Cleavage by the nuclease is also avoided if the target sequence contains mismatches, particularly in the PAM-distal region of the target (Cas9 gRNA engineering for genome editing, activation and repression. Nat Methods. 2015; 12(11):1051-1054). Similar to Cas9, the RuvC domain for Cas12 nucleases can be mutated to convert the nuclease into a programmable DNA binding protein (Identifying and Visualizing Functional PAM Diversity across CRISPR-Cas Systems. *Mol Cell.* 2016; 62(1):137-147), and introducing mismatches can prevent cleavage but preserve target binding (Multiplexed genome engineering by Cas12a and CRISPR arrays encoded on single transcripts. Nat Methods. 2019; 16(9):887-893). The method according to the present invention detects at least one sensed RNA in a cell, tissue, and/or sample. In the context of the present invention, a sensed RNA is any RNA of interest to be detected using the methods according to the present invention. Usually and preferably, the sensed RNA is a single-stranded RNA molecule, such as a messenger RNA, ribosomal RNAs, transfer RNAs, small RNAs, antisense RNAs, small nucleolar RNAs, microRNAs, piwiRNAs, long non-coding RNAs, spliced introns, and circular RNAs. The RNA can be of natural origin or artificially produced. The single stranded sensed RNA can be from a human cell, an animal cell, a plant cell, a cancerous cell, an infected cell, or a diseased cell, and/or can be derived from a virus, a parasite, a helminth, a fungus, a protozoan, a bacterium, or a pathogenic bacterium. The sensed RNA comprises a first portion that specifically hybridizes with a first portion of a non-naturally occurring tracrRNA as generated and used in the methods of the present invention, and a second portion that specifically hybridizes with at least one nucleic acid molecule.

The sensed RNA may comprise two or more of the first and second portions, and the non-naturally occurring tracrRNAs are designed accordingly. In the context of the present invention, a target nucleic acid can be any suitable target nucleic acid, but preferably comprises target DNA, or target RNA or target ssDNA, as some Cas9 and Cas12 nucleases can target these nucleic acids.

The sensed RNA may additionally comprise 5' and/or 3' ends extending from said first portion and extending outside of the complex as formed between the sensed RNA, the non-naturally occurring tracrRNA and the least one tracrRNA-dependent CRISPR nuclease enzyme (see FIG. 2), and may include portions recognized by a dsRNA-cleaving enzyme, and/or 5'-end that are cleaved or digested by other enzymes (see FIG. 2). 3'-ends are preferred as they can provide extensions to the hybridizing portions in the complex, which further stabilize the molecule(s).

The sensed RNA comprises at least one second portion thereof that specifically hybridizes with at least one portion of at least one target nucleic acid. In the context of the first aspect of the method according to the present invention, this binding of said at least one tracrRNA-dependent CRISPR nuclease enzyme in form of the complex between the sensed RNA, the non-naturally occurring tracrRNA and the at least one tracrRNA-dependent CRISPR nuclease enzyme (see FIG. 2) to said at least one target nucleic acid detects said at least one sensed RNA in said cell, tissue and/or sample. As described above, the detection of the complex can be direct (e.g. with antibodies) or indirect using suitable assays as described. The detection of the complex can also include a quantitative detection, i.e. the amount of complex as detected is used to determine the amount of sensed RNA in said cell, tissue and/or sample.

The sensed RNA may be labelled, either at the 3'- and/or 5'-end, and/or by including a marker inside the RNA molecule/strand. Respective methods are known to the person of skill. The sensed RNA may also be a combination of RNA with portions of DNA and/or PNA.

Certain portions of the nucleic acid molecules as used in the methods according to the present invention are found and/or designed to specifically hybridize with complementary portions in other molecules. As known to the person of skill, for this, the hybridization and washing conditions are critical. If the sequences are 100% complementary, then a high stringency hybridization may be carried out. Nevertheless, according to the invention, the portions that hybridize and/or specifically hybridize are complementary to at least 80%, preferably complementary to more than 90%, more preferably to more than 95%, and most preferably are 100% complementary. The stringency of hybridization is determined by the hybridization temperature and the salt concentration in the hybridization buffer, and high temperature and low salt is more stringent. A commonly used washing solution is SSC (Saline Sodium Citrate, a mixture of NaCitrate and NaCl). Hybridization may be carried out in solution or—more commonly—at least one component may be on a solid-phase support, e.g., nitrocellulose paper. Frequently used protocols employ a blocking reagent, such as casein from nonfat dried milk or bovine serum albumin, often in combination with denatured, fragmented salmon sperm DNA (or any other heterologous DNA of high complexity) and a detergent, such as SDS. Often a very high concentration of SDS is used as a blocking agent. Temperatures may be between 42 and 65° C. or higher, and buffers may be 3×SSC, 25 mM HEPES, pH 7.0, 0.25% SDS final.

The RNA-cleaving enzyme cleaves the hybridized region formed between the first portion of the sensed RNA and the anti-repeat portion of the non-natural tracrRNA, or it processes the other single-stranded end of the ncrRNA. This enzyme is preferably RNase III from *E. coli* but can be RNase III from other bacteria or archaea as well as other dsRNA-cleaving enzymes, such as Drosha, Dicer, DCL1, Rntp1, or Pac1p. The RNA-cleaving enzyme can also cleave ssRNA, such as RNase A.

Another aspect of the present invention then relates to a method for transcriptional recording, in particular in a multiplexed setting, in vitro or in vivo (see, for example, FIGS. 13 and 19 to 22). In in vivo transcriptional recording, using a method of the present invention as described herein, a (each) sensed RNA as present is converted into a readable signal or modification. In each example, the sensed RNA is converted into an ncrRNA through the non-natural tracrRNA, and the ncrRNA then directs the tracrRNA-dependent CRISPR nuclease to the target "reporter" DNA. This "reporter" DNA undergoes editing, resulting in a detectable marker, modification or "edit" that is maintained ("stored") in the DNA. Examples are indels, markers introduced through HDR, base editing, prime editing or RNA editing. As one read-out, the expression of a reporter gene may be modulated. A fusion between dCas9 and the transcriptional activation domain VP16 is shown in FIG. 13B, although many other modes of expression modulation are possible (e.g. fusing other regulatory domains to the nuclease, using a catalytically-dead nuclease or a catalytically-active nuclease paired with a partially mutated guide sequence, using scaffold sgRNAs that recruit the regulatory domains). In agreement with the robustness of the design for other methods as disclosed herein, it was also surprisingly found that the method for transcriptional recording is rather robust with respect to high G/C content and non-canonical sequences (see, for example, FIGS. 20 to 22, and also examples hereinbelow).

Previous examples of transcriptional recording sense environmental signals or non-specifically record the transcriptional profile of the cell. Environmental recording relies on inducible promoters that express CRISPR acquisition proteins or guide RNAs that drive editing. In contrast, transcriptional recording with non-natural tracrRNAs can record one or multiple specific transcripts in a cell. The recording does not require inducible promoters, and the non-natural tracrRNA dictates which transcript is recorded. Multiple non-natural tracrRNAs can also be combined with corresponding DNA targets for multiplexed recording.

Perli SD (in: Continuous genetic recording with self-targeting CRISPR-Cas in human cells. *Science.* 2016 Sep. 9; 353(6304):aag0511. doi: 10.1126/science.aag0511. Epub 2016 August 18. PMID: 27540006) disclose a self-contained analog memory device for longitudinal recording of molecular stimuli into DNA mutations in human cells. This device consists of a self-targeting guide RNA (stgRNA) that repeatedly directs *Streptococcus pyogenes* Cas9 nuclease activity toward the DNA that encodes the stgRNA, enabling localized, continuous DNA mutagenesis as a function of stgRNA expression. We demonstrate programmable and multiplexed memory storage in human cells triggered by exogenous inducers or inflammation, both in vitro and in vivo. This tool, Mammalian Synthetic Cellular Recorder Integrating Biological Events (mSCRIBE), provides a distinct strategy for investigating cell biology in vivo and enables continuous evolution of targeted DNA sequences.

Farzadfard F, et al. (in: Single-Nucleotide-Resolution Computing and Memory in Living Cells. Mol Cell. 2019 Aug. 22; 75(4):769-780.e4. doi: 10.1016/j.molcel.2019.07.011. PMID: 31442423; PMCID: PMC7001763) disclose DOMINO, a robust and scalable platform for encoding logic and memory in bacterial and eukaryotic cells. Using an efficient single-nucleotide-resolution Read-Write head for DNA manipulation, DOMINO converts the living cells' DNA into an addressable, readable, and writable medium for computation and storage. DOMINO operators enable analog and digital molecular recording for long-term monitoring of signaling dynamics and cellular events. Furthermore, multiple operators can be layered and interconnected to encode order-independent, sequential, and temporal logic, allowing recording and control over the combination, order, and timing of molecular events in cells. They envision that DOMINO will lay the foundation for building robust and sophisticated computation-and-memory gene circuits for numerous biotechnological and biomedical applications.

Tang W, and Liu D R. (in: Rewritable multi-event analog recording in bacterial and mammalian cells. Science. 2018 Apr. 13; 360(6385):eaap8992. doi: 10. 1 126/science.aap8992. Epub 2018 Feb. 15. PMID: 29449507; PMCID: PMC5898985) disclose that Cas9 nucleases and base editors can be used to record amplitude, duration, and order of stimuli as stable changes in both genomic and extrachromosomal DNA content (see the Perspective by Ho and Bennett). The recording of multiple stimuli—including exposure to antibiotics, nutrients, viruses, and light, as well as Wnt signaling—was achieved in living bacterial and human cells. Recorded memories could be erased and re-recorded over multiple cycles.

Finally, Schmidt, F. et al. (in: Transcriptional recording by CRISPR spacer acquisition from RNA. *Nature* 562, 380-385 (2018). https://doi.org/10.1038/s41586-018-0569-1) use CRISPR spacer acquisition to capture and convert intracellular RNAs into DNA, enabling DNA-based storage of transcriptional information. In *Escherichia coli*, we show that defined stimuli, such as an RNA virus or arbitrary sequences, as well as complex stimuli, such as oxidative stress, result in quantifiable transcriptional records that are stored within a population of cells. They demonstrate that the transcriptional records enabled classifying and describing complex cellular behaviors and identifying the precise genes that orchestrate differential cellular responses. In the future, CRISPR spacer acquisition-mediated recording of RNA followed by deep sequencing (Record-seq) could be used to reconstruct transcriptional histories that describe complex cell behaviors or pathological states.

Preferred is a method for transcriptional recording, in particular in a multiplexed setting, in vitro or in vivo of at least one target DNA in a cell, tissue and/or sample, said method comprising: a) contacting said sample, cell or tissue with at least one non-naturally occurring tracrRNA comprising a portion that specifically hybridizes with a first portion of a sensed RNA, wherein a second portion of said sensed RNA specifically hybridizes with said at least one target DNA; wherein said least one non-naturally occurring tracrRNA is hybridized or is able to be hybridized with said sensed RNA in the presence of at least one tracrRNA-dependent CRISPR nuclease enzyme, optionally further comprising the presence of a dsRNA-cleaving enzyme, such as RNase III; and b) nicking or cleaving of said at least one target nucleic acid in said sample by said nuclease, c) detectably editing said at least one target DNA comprising, for example, non-homologous end joining (NHEJ) repair, microhomology-mediated end joining (MMEJ), homologous-directed repair (HDR), a detectable marker, a detectable modification, base editing, prime editing or RNA editing, and d) optionally, suitably detecting said editing of said at least one target DNA comprising, for example, at least one method selected from detecting the presence and/or length of indels or gene edits, the activation/repression of a gene or other genetic element as encoded by said at least one target nucleic acid, and/or the detection of said prime or base editing; e) wherein detecting said editing of said at least one target DNA records transcription of said at least one sensed RNA in said cell, tissue and/or sample. Preferred embodiments and components are similar to the other methods as described herein.

Preferred uses of the transcriptional recording according to the present invention relate to the analysis of microbiomes and/or microbial sentinels (i.e. commensal bacteria that serve as reporters for non-invasive measurements, see, for example, Stewart J R, et al. The coastal environment and human health: microbial indicators, pathogens, sentinels and reservoirs. Environ Health. 2008 Nov. 7; 7 Suppl 2(Suppl 2):S3. doi: 10.1186/1476-069X-7-S2-S3. PMID: 19025674; PMCID: PMC2586716), and the tracking of viral or bacterial spread in vivo, such as whole organisms, or based on samples, for example taken from the environment (e.g. spread of viruses or resistant bacteria detected in waste water samples, etc.).

During work in the context of the present invention using the 84-21 strain of *Campylobacter jejuni* (Cje), the inventors assessed RNAs that co-immunoprecipitated with the Cje-Cas9. While one set shared complementarity to the crRNA2 in that strain, another set shared complementarity to the anti-repeat portion of the trans-acting CRISPR RNA (tracrRNA), responsible for crRNA maturation. This binding paralleled how tracrRNAs process crRNAs from the repeat to form the mature crRNA. These insights provided the first indication that mature crRNAs (which guide Cas9 to their target) could be derived from mRNAs and other RNAs besides those encoded by CRISPR arrays, although it was thought that crRNAs can only be derived from within CRISPR arrays and CRISPR-Cas systems.

It was surprisingly found in the context of the present invention, that the tracrRNA-dependent CRISPR nuclease enzyme system can be designed in certain ways in order to provide a highly versatile and specific diagnostic tool. An essential element of this tool is the design of non-naturally occurring tracrRNAs. The specific modification and thus "reprogramming" of the tracrRNAs allow for the generation of purpose-specific ncrRNAs. Interestingly, the tracrRNA-dependent CRISPR nuclease enzyme system was found to be still functional, despite the expectation that reprogramming the tracrRNA would potentially disrupt Cas9 recognition and activity.

In the context of the present invention, RNAs as identified with the motif complementary to the tracrRNA anti-repeat had the approximate size of a processed crRNA (36-37 nts). In one specific example (derived from the fliF gene), the ncrRNA matched to an architecture of a crRNA (~24 nt guide+-12 nt processed repeat). Preferred is a method according to the present invention, wherein said portion of said at least one non-naturally occurring tracrRNA that specifically hybridizes with said first portion of said sensed RNA hybridizes with 10 or more nucleotides, preferably with 11 and more nucleotides, and more preferred with about 12 nucleotides or more. Preferred ranges are between 9 and 15 nucleotides, more preferred 10 to 14 nucleotides, and most preferred 12 nucleotides. As mentioned above, extensions to the hybridizing portions in the complex (5' extension of tracrRNA, 5'-extensions to ncrRNA) are possible and preferred, and provide the advantage of a more stable formation the complex.

The non-naturally occurring tracrRNA as used in the present invention comprises a sequence that specifically hybridizes with a first portion of said sensed RNA, forming a stem-like secondary structure basically mimicking the original repeat:anti-repeat stem formed between a crRNA and a tracrRNA. Preferred is a method according to the present invention, wherein said portion of said at least one non-naturally occurring tracrRNA that specifically hybridizes with said first portion of said sensed RNA hybridizes with 10 or more nucleotides, preferably with 11 and more nucleotides, and more preferred with about 12 nucleotides or more.

Figure 14:
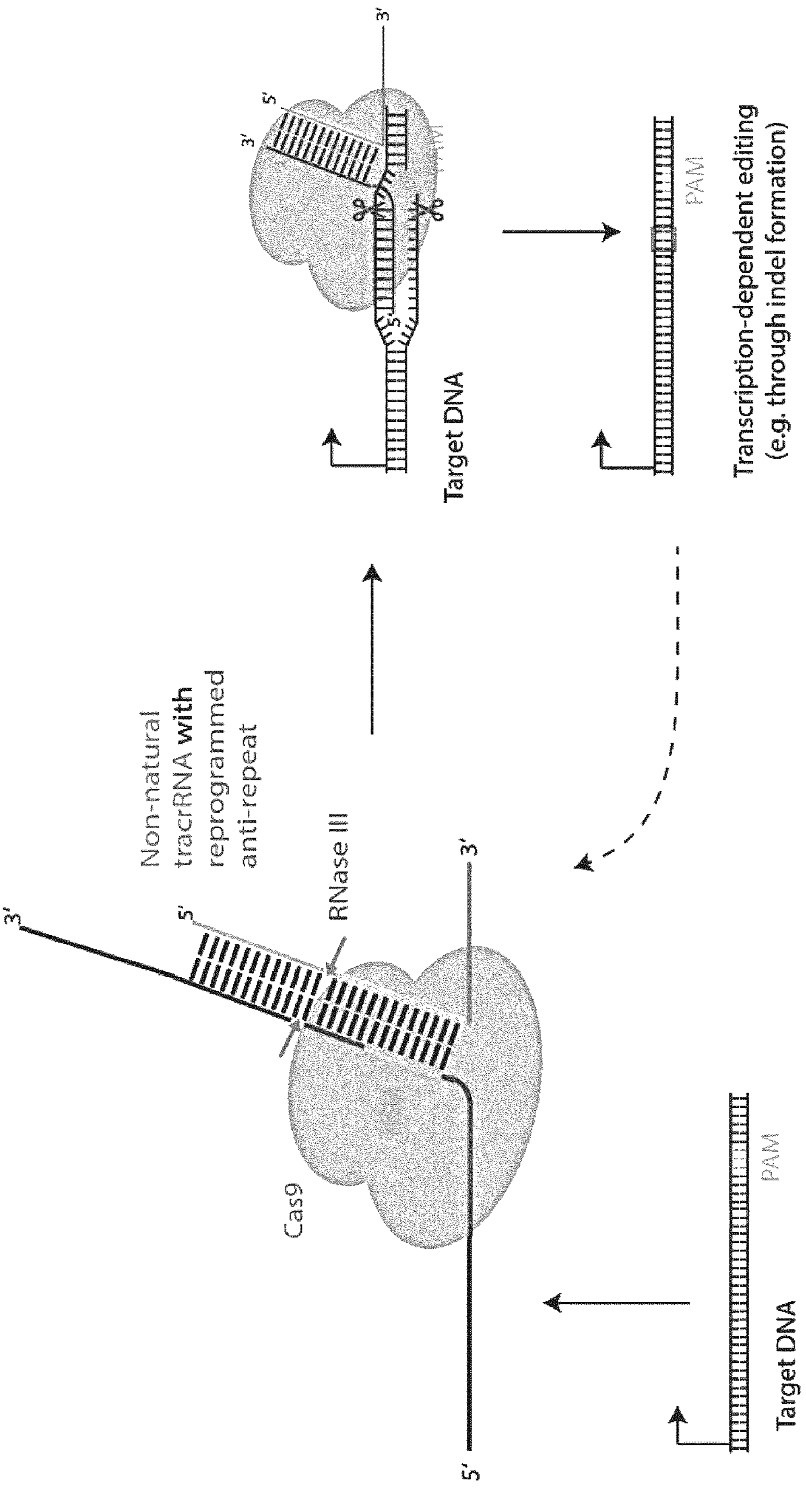

Preferred is a method according to the present invention, wherein said first portion of said sensed RNA comprises a PAM (see FIG. 14). As an example, for Cas12 nucleases, the PAM is present within the repeat portion upstream of the guide portion of the resulting ncrRNA, whereas for Cas9, the PAM is present in the repeat portion downstream of the guide portion of the ncrRNA. By selecting targets with the appropriate PAM, the generated crRNA could target its own DNA site, i.e. allowing the ncrRNA to target the DNA that gave rise to the ncrRNA. This allows editing only when the gene is transcribed. This strategy can be used to greatly limit editing, e.g. only in specific tissues, depending on the expression profile of the gene.

In a preferred embodiment of the methods according to the present invention, the nuclease can be modified in order to recognize a broader panel of PAM sites, e.g. by replacing the key region in the PAM interaction (PI) domain of Cas9 with the corresponding region in a panel of related Cas9 orthologs (see for example, Ma et al., Engineer chimeric Cas9 to expand PAM recognition based on evolutionary information. Nat Commun. 2019 Feb. 4; 10(1):560. doi: 10.1038/s41467-019-08395-8). This broadens the possible genomic targets in cells.

As mentioned above, the non-naturally occurring tracrRNA as used in the present invention comprises a sequence that specifically hybridizes with a first portion of said sensed RNA, forming a stem-like secondary structure basically mimicking the original repeat:anti-repeat stem. In a preferred embodiment of the methods according to the present invention, this stem-like secondary structure can be extended (i.e. 3' to the mRNA and 5' to the non-naturally occurring tracrRNA, creating a dsRNA, and thus an RNase III recognition site or domain. This structure can be used in certain assays, e.g. when attaching detectable groups to the stem extension that could be cleaved off by the RNase activity. The inventors evaluated mismatches in the repeat-anti-repeat stem recognized and cleaved by RNase III. ncrRNA variants were expressed with a tracrRNA. Mutations were made in the ncrRNA to preserve the tracrRNA. Overall, even large mutations could be tolerated. Without wanting to be bound by theory, this suggests that RNase III might be dispensable for Cas9 activity.

It was furthermore analyzed by the inventors, how far ncrRNAs can deviate from traditional crRNAs, indicating the "robustness" of the system with respect to the stem-like secondary structure basically mimicking the original repeat: anti-repeat stem in the natural duplex (see above). A particular focus was put on the base stem bound by Cas9. Bulges were created by mutating the repeat, thereby preserving the tracrRNA. The results show that bulges can be tolerated to quite some degree, especially when the bulge is smaller, away from the base of the stem, or on the repeat side. A very similar result was found when accommodating some mismatches in the stem. See FIGS. 5-9 for the supporting data.

The inventors further analyzed how far ncrRNAs can deviate from traditional crRNAs, indicating the "robustness" of the system with respect to the stem-like secondary structure basically mimicking the original repeat:anti-repeat stem in the natural duplex (see above). A second particular focus was put on the base stem bound by Cas12. Bulges were created by mutating the repeat, thereby preserving the tracrRNA. The results show that bulges can be tolerated to quite some degree, especially when the bulge is smaller, away from the base of the stem, or on the repeat side. A very similar result was found when accommodating some mismatches in the stem. See FIGS. 23-25 for the supporting data.

Therefore, as shown with the two examples Cas 9 and Cas12, ncrRNAs can deviate from traditional crRNAs, indicating the "robustness" of the system with respect to the stem-like secondary structure basically mimicking the original repeat:anti-repeat stem in the natural duplex (see above).

Figure 4A:
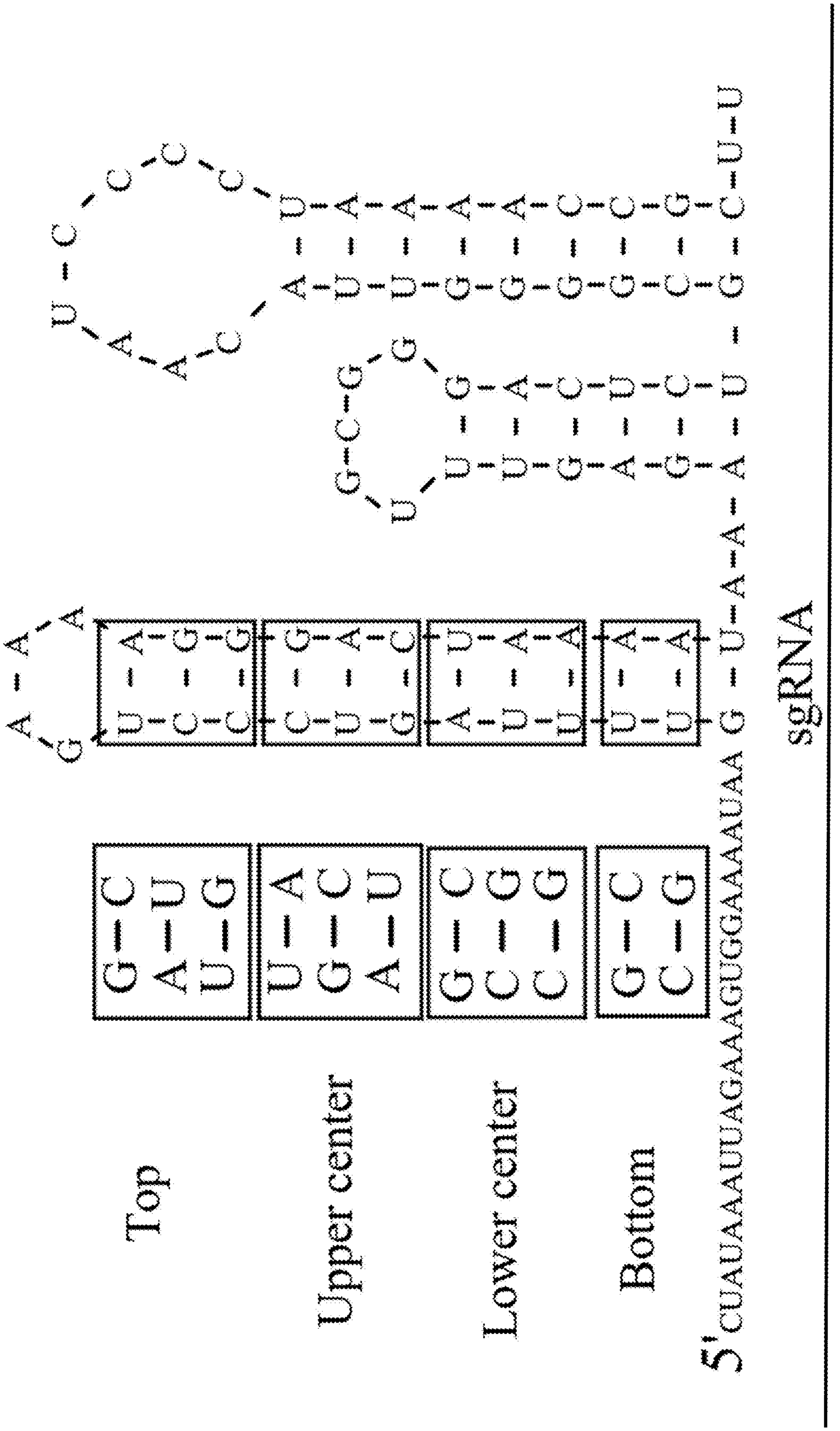
Figure 6A:
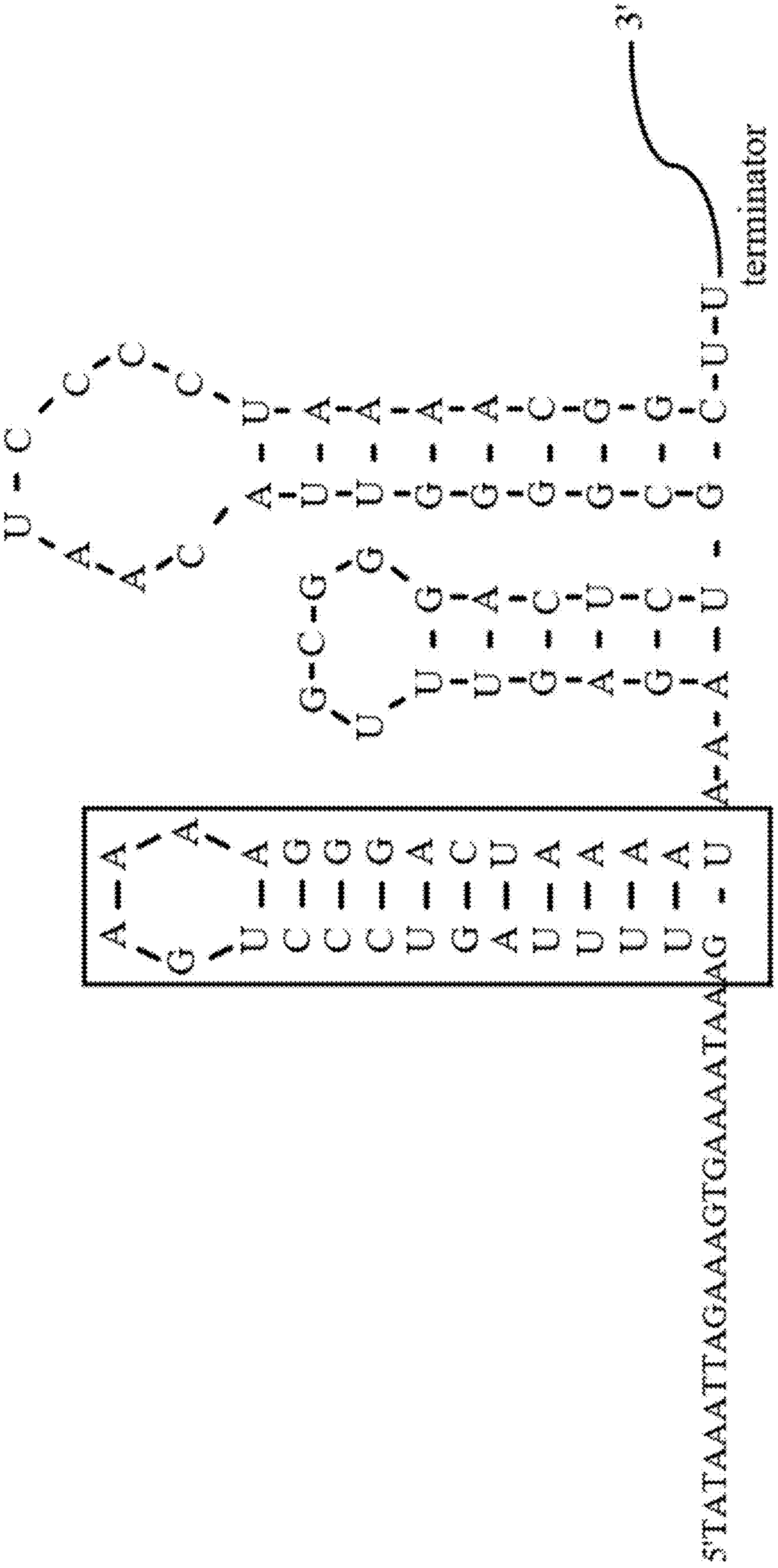
Figure 6B:
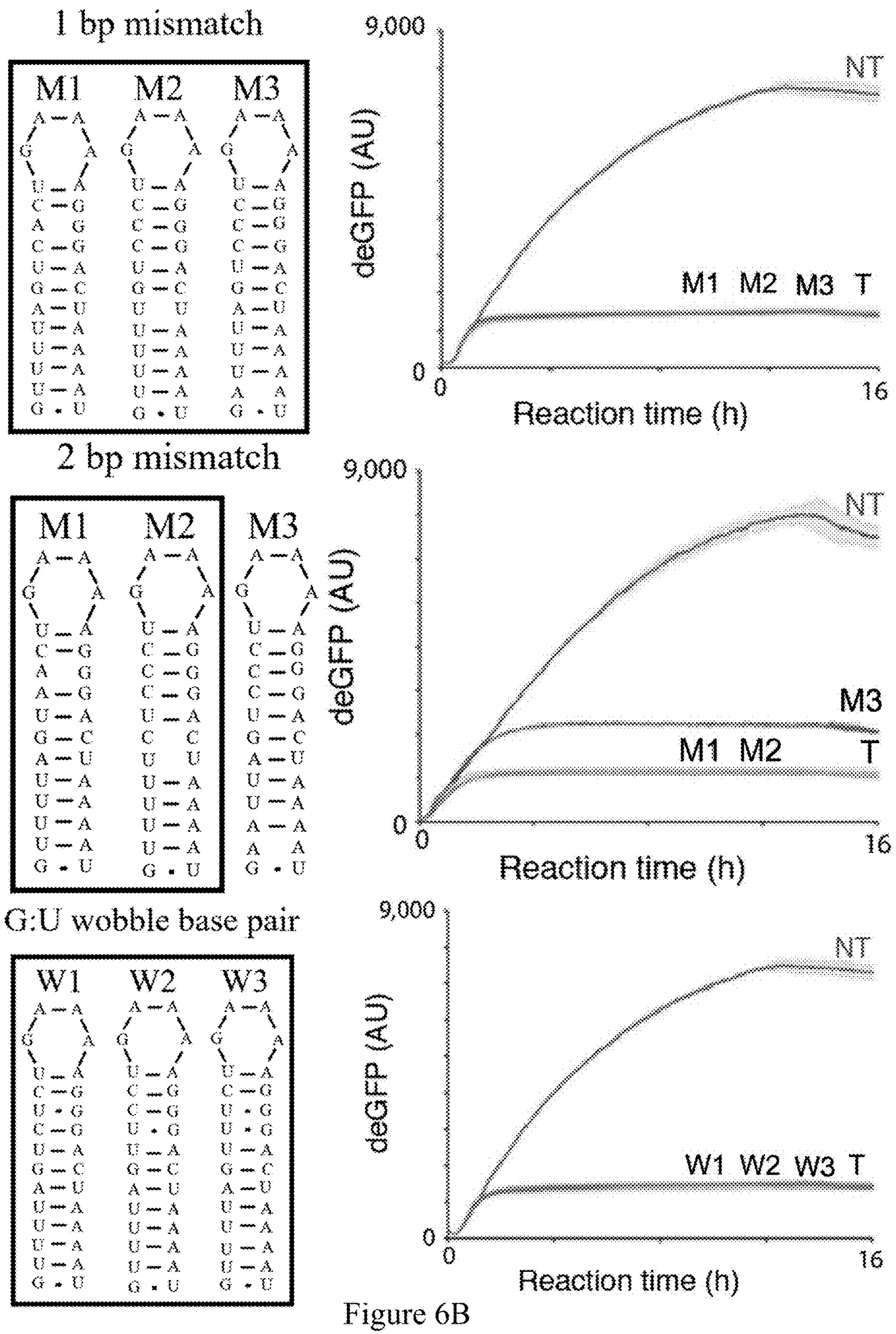
Figure 7A:
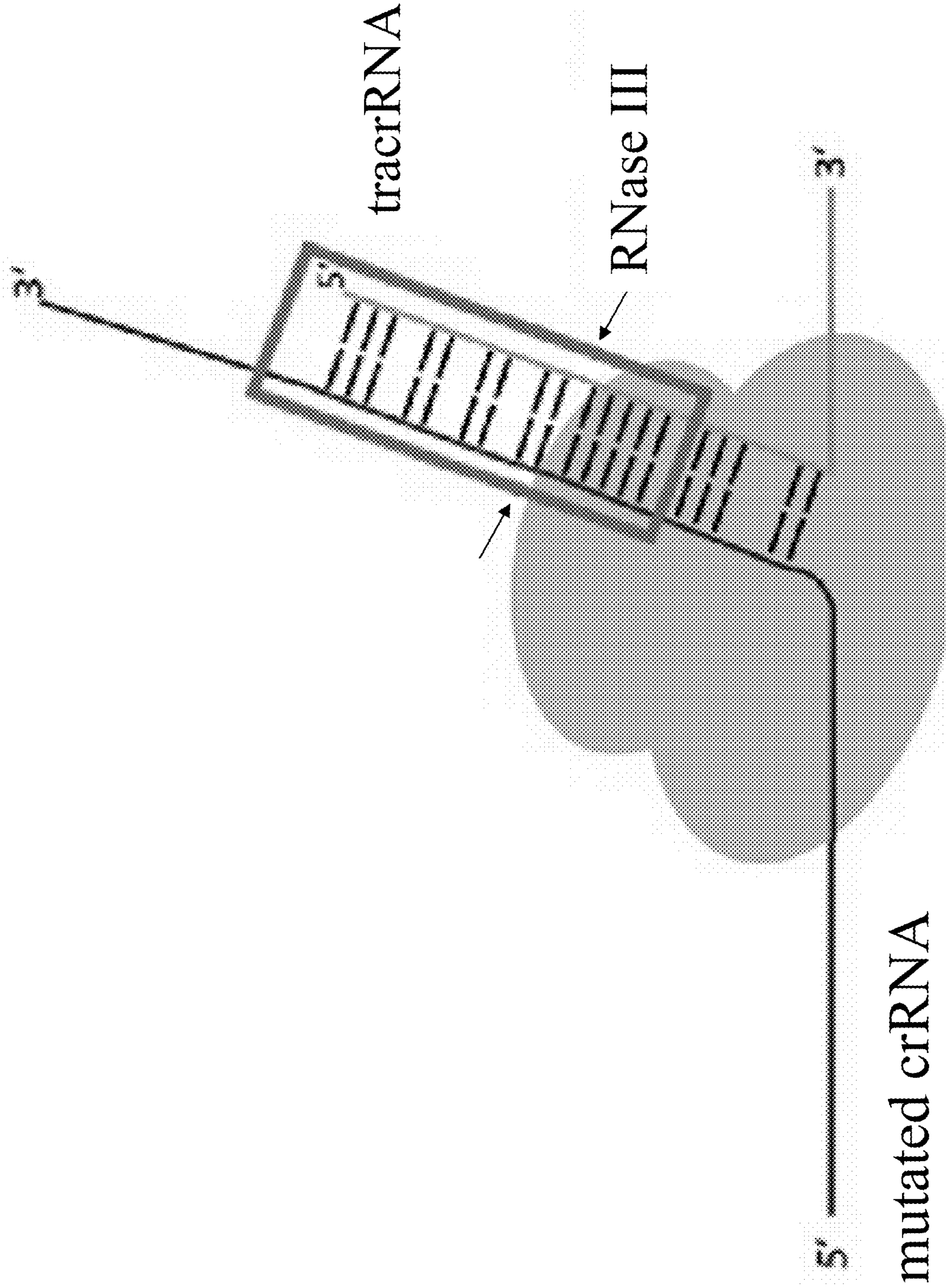
Figure 7B:
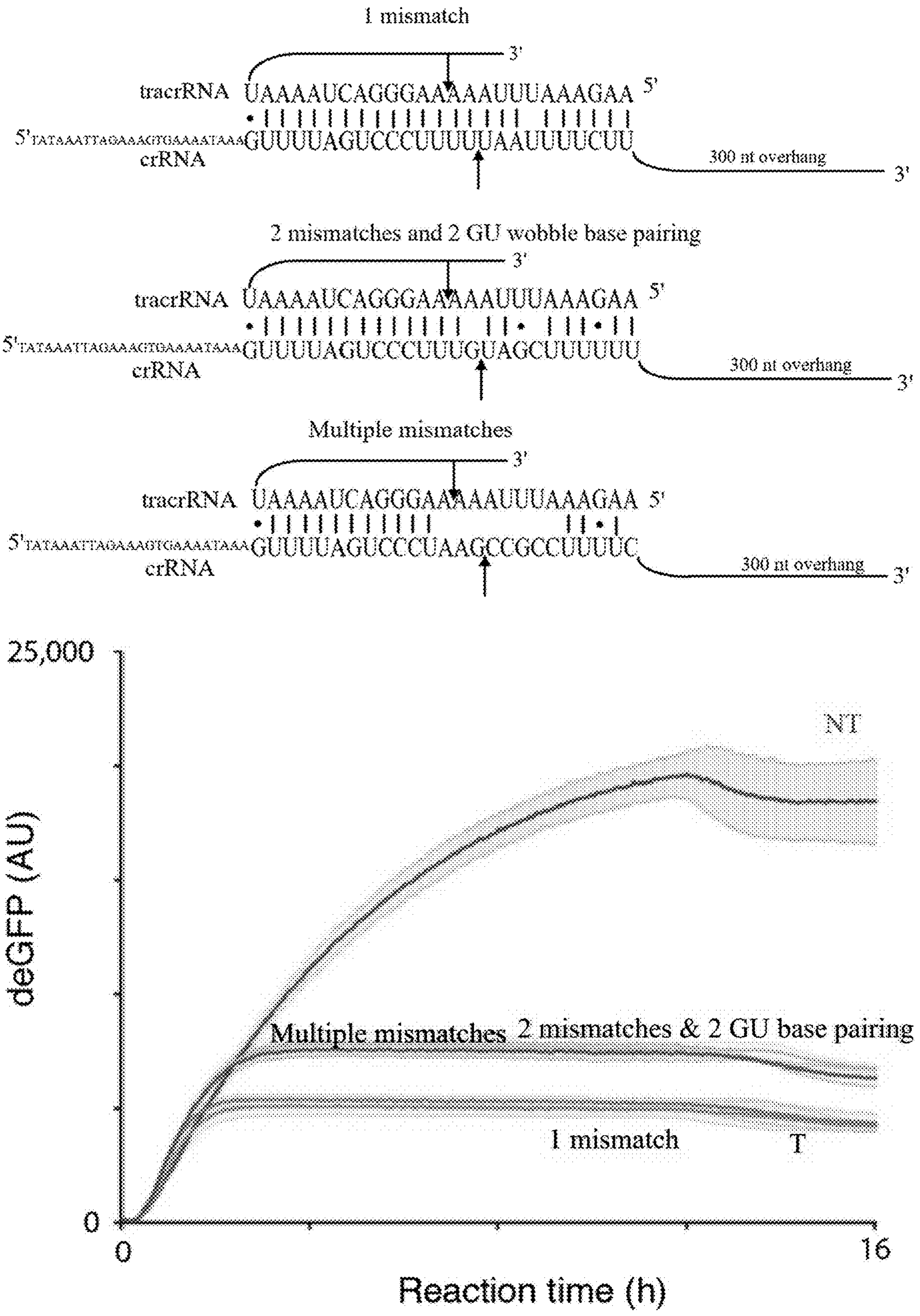
Figure 7C:
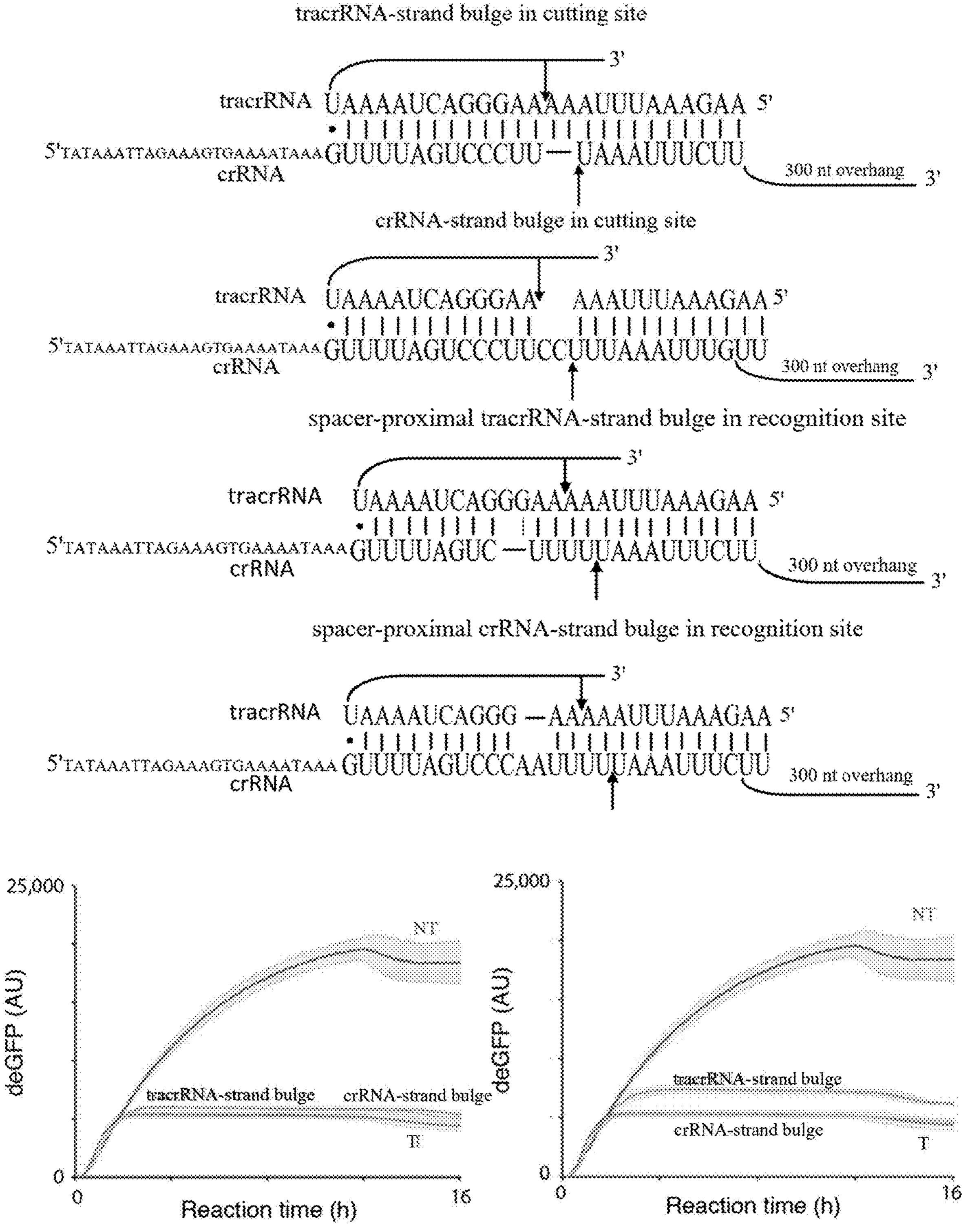
Figure 8A:
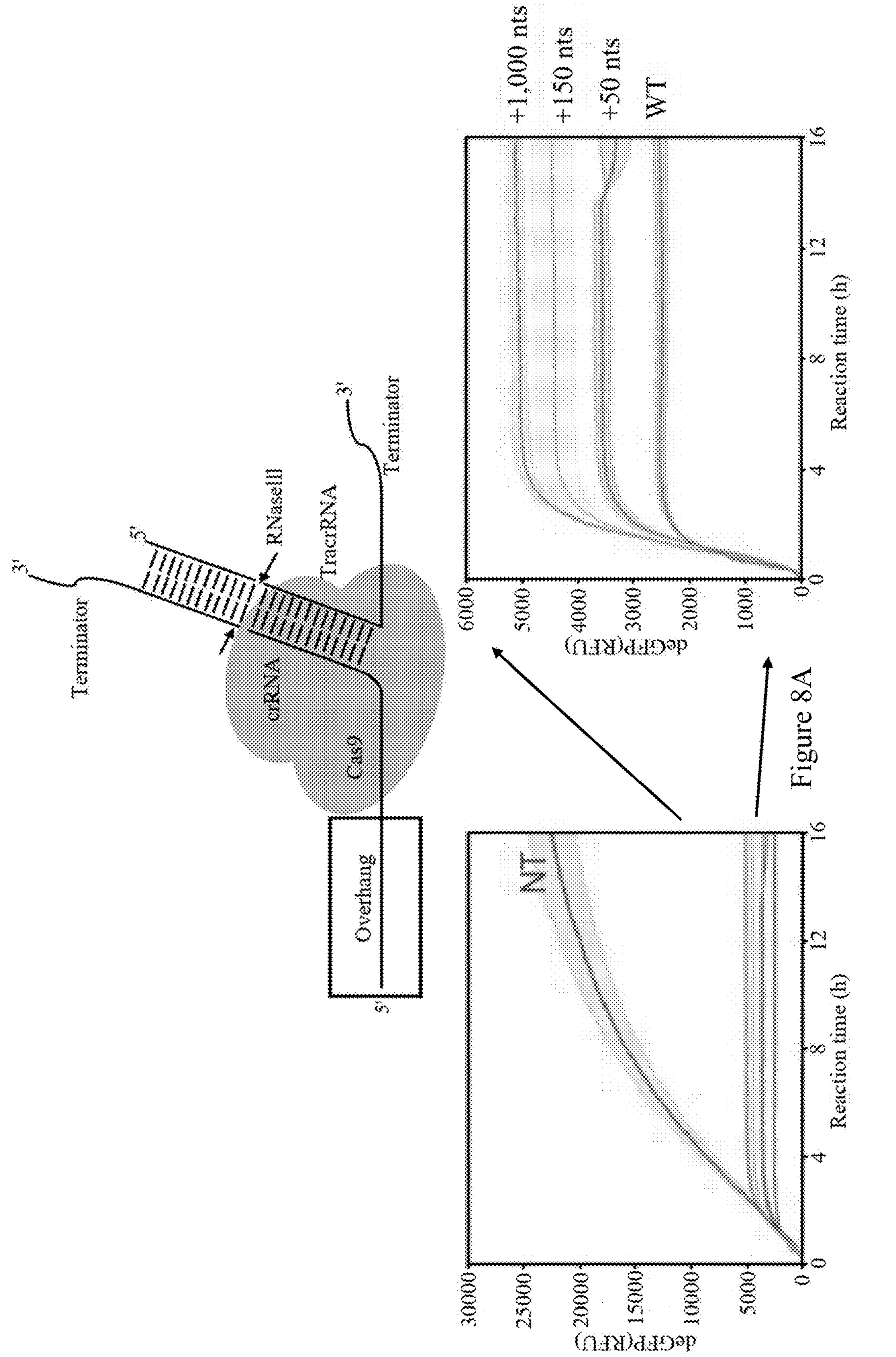
Figure 8B:
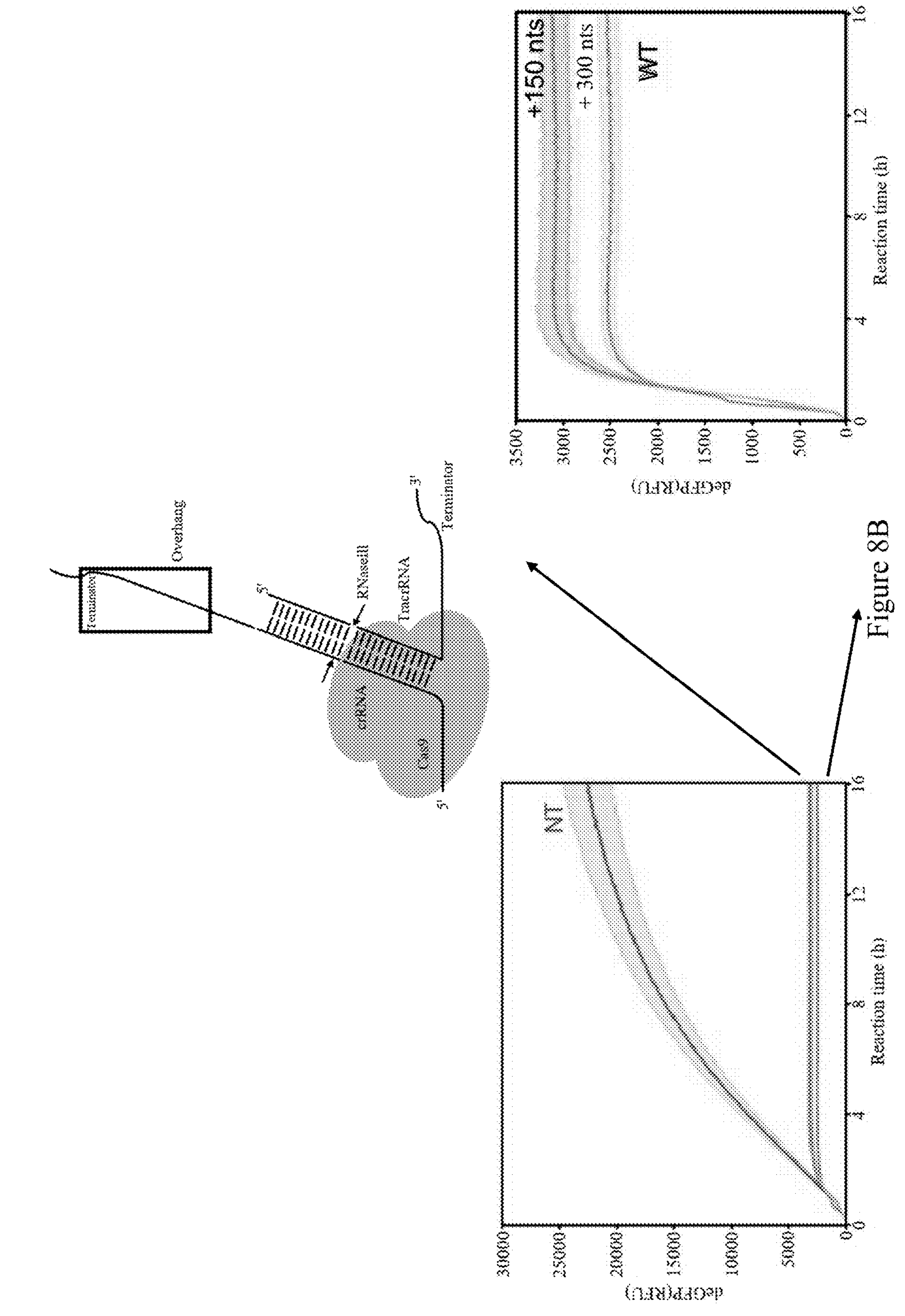

Furthermore, the effect of reprogramming tracrRNA to convert different RNAs into crRNAs was tested. Changes to the repeat:anti-repeat duplex using sgRNAs and CjeCas9 in TXTL were evaluated, and it was found that all changes could be accommodated, with little impact on target cleavage (see FIG. 4). In particular, the duplex between the repeat and anti-repeat can accommodate different sequences with little impact on targeting activity by CjeCas9 (FIG. 4). It was found that mutations resulted in limited impact on the time to target cleavage. Also the duplex between the repeat and anti-repeat can accommodate some bulges on either side as part of DNA targeting by CjeCas9 (FIG. 5), and the duplex between the repeat and anti-repeat can accommodate mismatches as part of DNA targeting by CjeCas9 as well (FIG. 6). Most of the duplexes maintained targeting activity despite the presence of the bulges. The region of the repeat: anti-repeat duplex involved in RNase III processing can accommodate mismatches and bulges as part of DNA targeting by CjeCas9 as well (FIG. 7). FIG. 8 shows that extensions to the 5' end or the 3' end of the crRNA have limited impact on targeting activity by CjeCas9. Similar rules apply to Cas12 and other enzymes as disclosed herein (see FIGS. 22 to 25).

Figure 9:
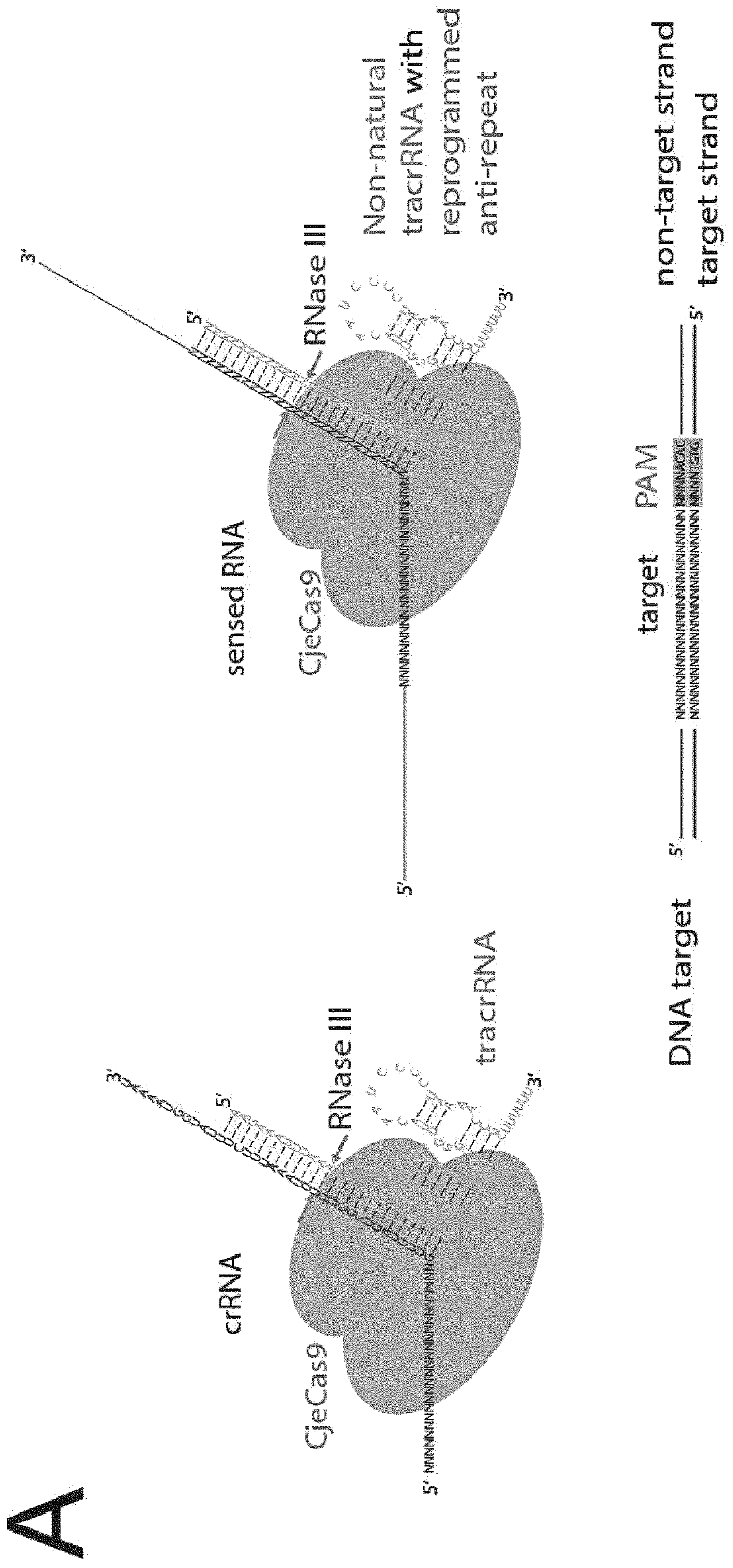
Figure 9:
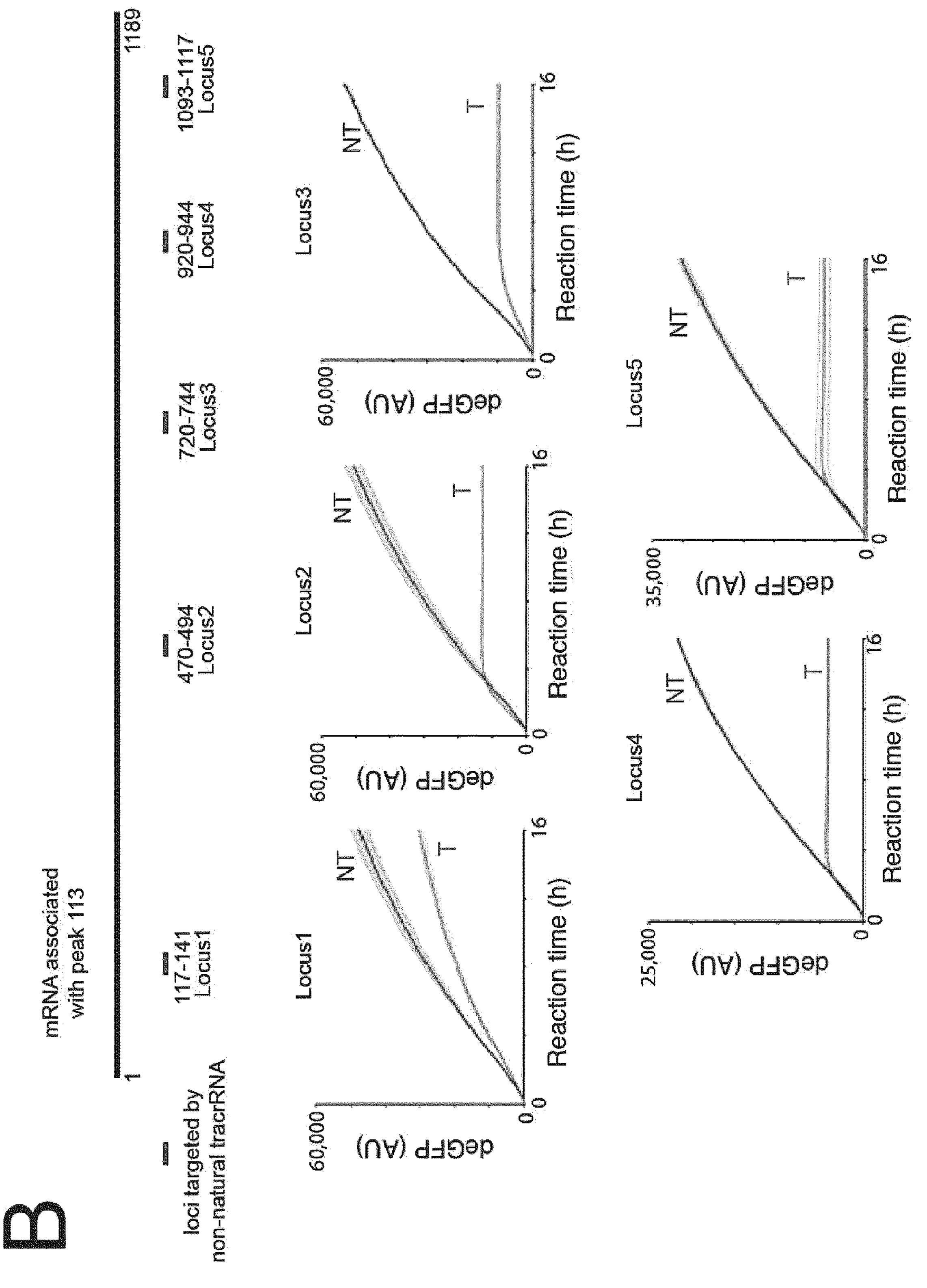
Figure 10A:
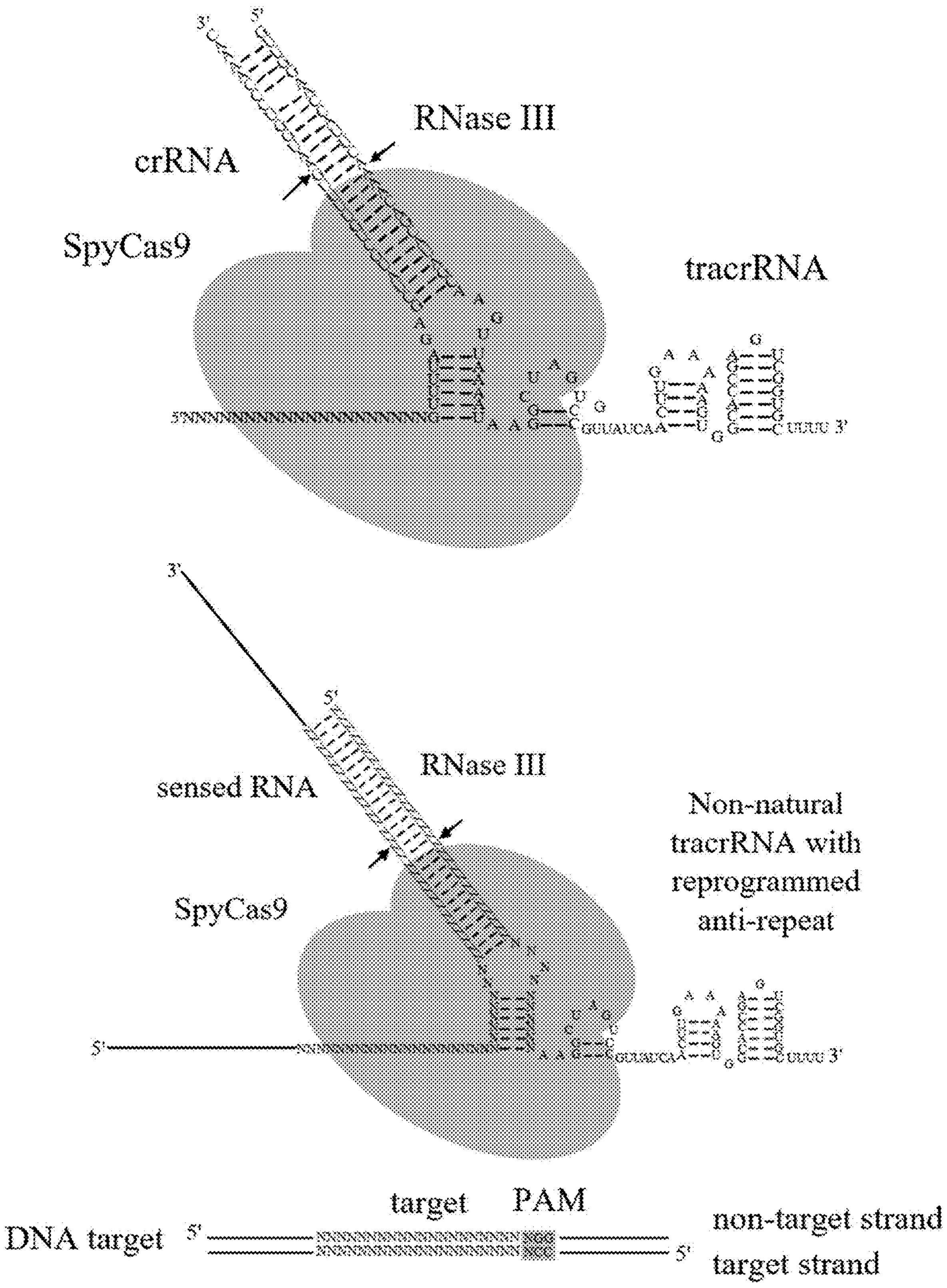
Figure 10B:
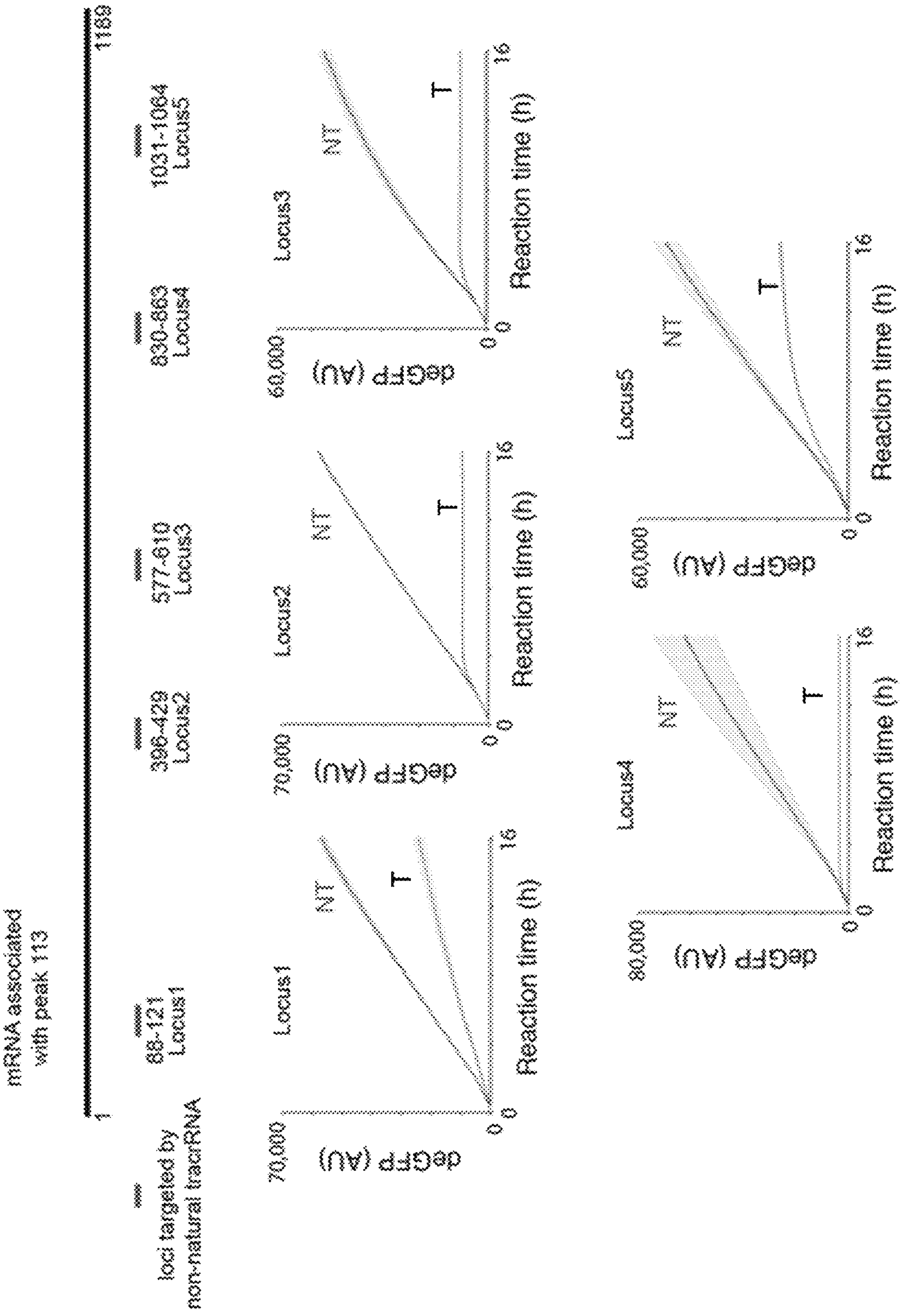
Figure 11A:
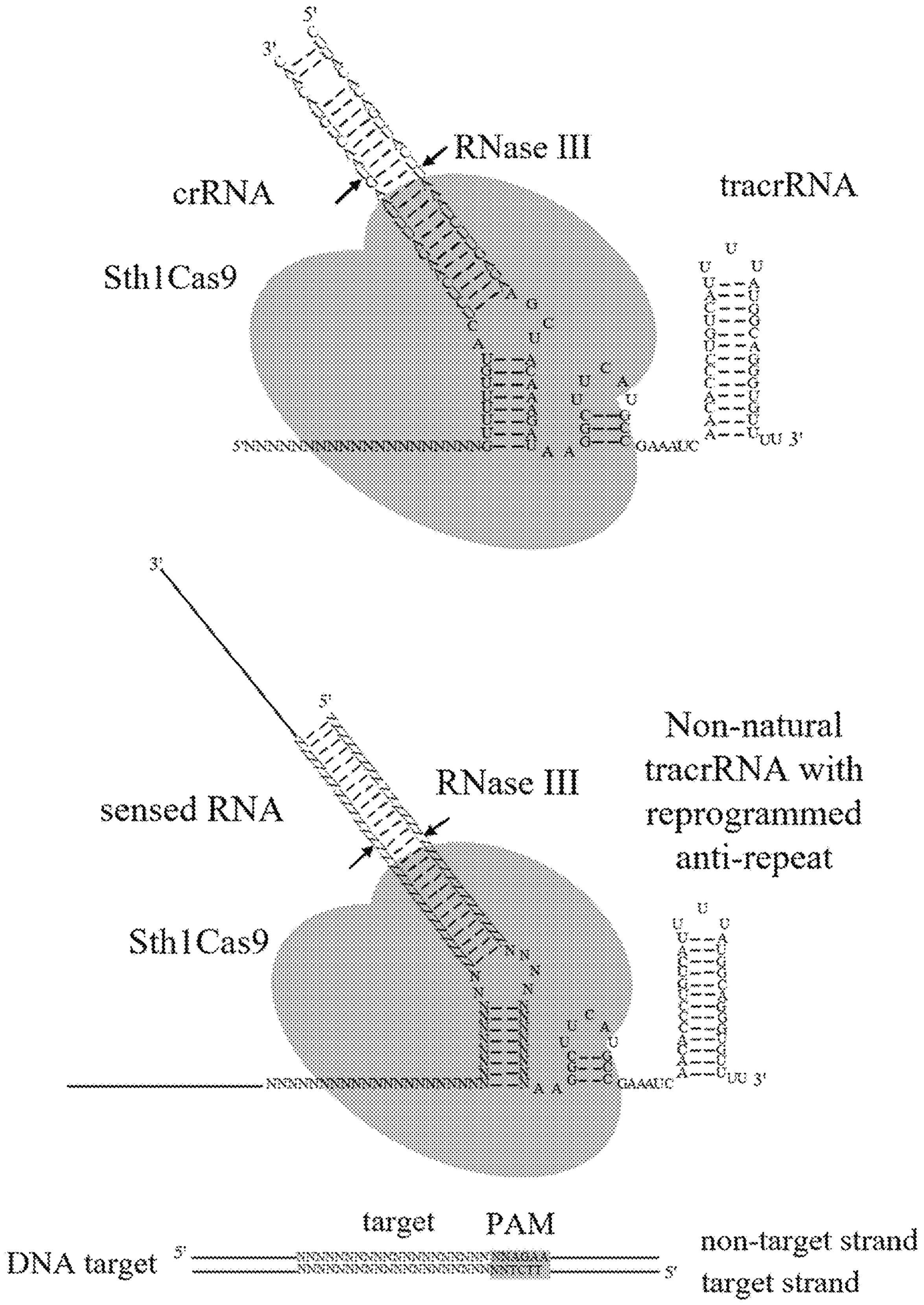
Figure 11B:
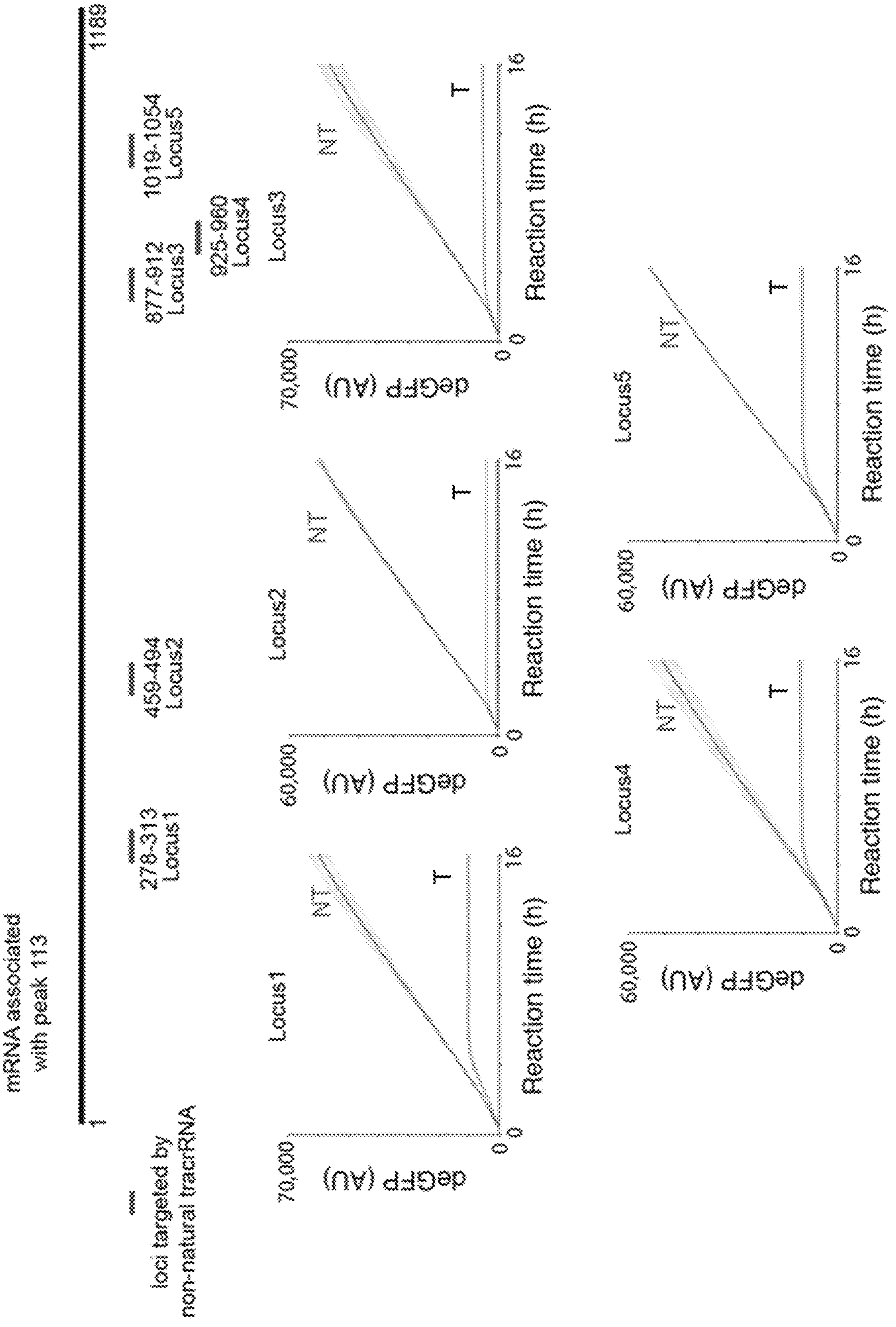

It was furthermore shown that non-natural tracrRNAs converting a sensed RNA into an active crRNA function well with CjeCas9 (FIG. 9), SpyCas9 (FIG. 10), and SthlCas9 (FIG. 11). According to the present invention, non-natural tracrRNAs can be designed to direct formation of active ncrRNAs used by CjeCas9 from a sensed RNA (FIG. 9). After design, the TXTL results demonstrate the DNA targeting directed by a sensed RNA and a non-natural tracrRNA. Each non-natural tracrRNA is designed to hybridize to a specific region of the tested RNA. Overall, all five tested non-natural tracrRNAs resulted in strong cleavage activity. In another aspect, non-natural tracrRNAs can be designed to direct formation of active ncrRNAs used by SpyCas9 from a sensed RNA (FIG. 10). Again, all five tested non-natural tracrRNAs resulted in strong cleavage activity. Therefore, other Cas9's (SpyCas9, SthlCas9) distinct from the CjeCas9 can be used with reprogrammed tracrRNAs to convert sensed RNAs into active crRNAs. Again, similar rules apply to Cas12 and other enzymes as disclosed herein.

The second portion of the sensed RNA specifically hybridizes with at least one target nucleic acid, defining the nucleic acid target of the Cas protein, creating the crRNA-like ncrRNA. The at least one non-naturally occurring tracrRNA is hybridized or is able to be hybridized with said sensed RNA in the presence of at least one tracrRNA-dependent CRISPR nuclease enzyme.

The non-naturally occurring tracrRNA can be produced in accordance with standard methods, e.g. synthetically produced, generated by in vitro transcription, and/or cloned into a plasmid. The tracrRNA can be derived from naturally occurring sequences that are then modified in order to generate sequences in the molecule as desired. The tracrRNA can further comprise additional modifications, such as labels or modified nucleotides, e.g. inosines, or the like.

In the second aspect thereof, the object of the present invention is solved by providing a method for detecting at least one sensed RNA in a cell and/or sample, said method comprising: a) contacting said sample with at least one non-naturally occurring tracrRNA comprising a portion that specifically hybridizes with a first portion of said sensed RNA, wherein a second portion of said sensed RNA specifically hybridizes with at least one target nucleic acid; wherein said at least one non-naturally occurring tracrRNA is hybridized or is able to be hybridized with said sensed RNA in the presence of at least one tracrRNA-dependent CRISPR nuclease enzyme, optionally further comprising the presence of an ssRNA and/or dsRNA cleaving enzyme, such as RNase III enzyme; b) detecting cleavage of said at least one target nucleic acid in said sample by said nuclease enzyme; c) wherein detecting said cleavage of at least one target nucleic acid detects said at least one sensed RNA in said cell, tissue and/or sample.

While the basic principles of this second aspect regarding the components as used are as above, in the aspect of the present invention, the detection of said at least one sensed RNA in said cell, tissue and/or sample relies on the detection of a cleaving of said at least one target nucleic acid in said sample by said nuclease enzyme, and detecting said cleaving of said at least one target nucleic acid detects said at least one sensed RNA in said cell, tissue and/or sample.

The detection of the binding and/or cleavage product based on the target nucleic acid can be direct (e.g. detecting a size change of the cleaved nucleic acid) or indirect using suitable fluorophores with or without quenchers. Cleaving the nucleic acid may release a fluorophore that can be detected, passing the cleaved nucleic acid through a nanopore sequencer detects changes, a fluorescently labeled nuclease could be localized, and/or the cleaving affects electrical currents that can be detected. The detection of the cleaved product can also include a quantitative detection, i.e. the amount of fragment(s) as detected is used to determine the amount of sensed RNA in said cell, tissue and/or sample.

Detection of binding can be indirect based on modulating the expression of a reporter gene. An at least one catalytically-dead nuclease can directly repress transcription by binding the promoter or coding region of the reporter gene. Alternatively, the nuclease can recruit regulatory domains responsible for the local modulation of gene expression, such as domains that upregulate expression (e.g. VP16, VPR) or downregulate expression (e.g. KRAB). The domains can be operably linked to the at least one catalytically-dead nuclease. The domains can be recruited through interactions with binding domains fused to the at least one catalytically-dead nuclease and/or the tracrRNA.

In the third aspect thereof, the object of the present invention is solved by providing a method for detecting at least one sensed RNA in a cell, tissue and/or sample, said method comprising: a) contacting said sample with at least one non-naturally occurring tracrRNA comprising a portion that specifically hybridizes with a first portion of said sensed RNA, wherein a second portion of said sensed RNA specifically hybridizes with at least one target nucleic acid; wherein said least one non-naturally occurring tracrRNA is hybridized or is able to be hybridized with said sensed RNA in the presence of at least one tracrRNA-dependent CRISPR nuclease enzyme, optionally further comprising the presence of an ssRNA and/or dsRNA cleaving enzyme, such as RNase III enzyme; and b) nicking or cleaving of said at least one target nucleic acid in said cell, tissue and/or sample by said nuclease, c) detectably editing said at least one target nucleic acid comprising, for example, non-homologous end joining (NHEJ) repair, microhomology-mediated end joining (MMEJ), homologous-directed repair (HDR), prime editing, base editing or RNA editing, and d) suitably detecting said editing of said at least one target nucleic acid comprising, for example, at least one method selected from detecting the presence and/or length of indels or gene edits, the activation/repression of a gene or other genetic element as encoded by said at least one target nucleic acid, and/or the detection of said prime or base editing; e) wherein detecting at least one target nucleic acid detects said at least one sensed RNA in said cell, tissue and/or sample.

While the basic principles of this third aspect regarding the components as used are as above, in this aspect of the present invention, the detection of said at least one sensed RNA in said cell, tissue and/or sample relies on the detection of a cleaving of said at least one target nucleic acid in said sample by said nuclease enzyme, detectably editing said cleaved at least one target nucleic acid, and furthermore suitably detecting said editing of said at least one target nucleic acid, wherein detecting said editing of said at least one target nucleic acid detects said at least one sensed RNA in said cell, tissue and/or sample. Therefore, this aspect relies on detecting changes to the target nucleic acid that are controlled or caused ("driven") by the sensed RNA.

Said detectably editing said cleaved at least one target nucleic acid can preferably comprise, non-homologous end joining (NHEJ) repair, microhomology-mediated end joining (MMEJ), homologous-directed repair (HDR), and/or base editing. For example, cells or single cell zygotes commonly repair Cas9 cleaved DNA using the error-prone non-homologous end joining (NHEJ) repair pathway, which randomly inserts or deletes DNA bases to repair double-strand breaks. The most common indels from NHEJ repair range from 1 to 15, preferably 1 to 9 nucleotides. There are multiple repair pathways known to the person of skill that can be engaged depending on the cell type and conditions.

Detecting said editing of said at least one target nucleic acid can comprise, for example, at least one method selected from detecting the presence and/or length of indels or gene edits, the activation/repression of a gene or other genetic element as encoded by said at least one target nucleic acid, and/or the detection of base editing, e.g. through sequencing, restriction digest and or detection of length changes of the target nucleic acid. As above, detection of the cleavage product based on the target nucleic acid can be direct (e.g. detecting a size change of the cleaved nucleic acid) or indirect using suitable fluorophores. Cleaving the nucleic acid may release a fluorophore that can be detected, passing the cleaved nucleic acid through a nanopore sequencer detects changes, a fluorescently labeled nuclease could be localized, and/or the cleaving affects electrical currents that can be detected. The detection of the cleaved product can also include a quantitative detection, i.e. the amount of fragment(s) as detected is used to determine the amount of sensed RNA in said cell, tissue and/or sample.

Preferred is a method according to the present invention, wherein the length of said indels as detected is between about 1 to 15, and more preferable between about 1 to 9 nucleotides, and wherein optionally said indels can be detected through sequencing, restriction digest and or detection of length changes of the target nucleic acid, as well as qPCR. In one preferred aspect, this will allow an improvement of the efficiency of gene editing by so-called iterative self-targeting. The presence of indels in most instances allows a re-targeting of the sequence, hence leading to a re-attack. The approach can then lead to larger sized indels and/or a higher frequency of homologous recombination, since some indels don't disrupt said re-attack. In practice, this approach advantageously allows for a follow-up of lineage tracing.

Base editing that can be detected represents a distinct means of editing. In general, there are two classes of base editors-cytosine base editors (CBEs) and adenine base editors (ABEs). Cytosine base editors are created by fusing Cas9 nickase or catalytically inactive "dead" Cas9 (dCas9) to a cytidine deaminase like APOBEC. Base editors are targeted to a specific locus by the present system, and they can convert cytidine to uridine within a small editing window near the PAM site. Uridine is subsequently converted to thymidine through base excision repair, creating a C to T change (or a G to A on the opposite strand). Adenosine base editors have been engineered to convert adenosine to inosine, which is treated like guanosine by the cell, creating an A to G (or T to C) change. Adenine DNA deaminases do not exist in nature, but have been created by directed evolution of the *Escherichia coli* TadA, a tRNA adenine deaminase. Like cytosine base editors, the evolved TadA domain is fused to a Cas9 protein to create the adenine base editor.

Both types of base editors are available with multiple Cas9 variants including high fidelity Cas9's (see below). Further advancements have been made by optimizing expression of the fusions, modifying the linker region between Cas variant and deaminase to adjust the editing window, or adding fusions that increase product purity such as the DNA glycosylase inhibitor (UGI) or the bacteriophage Mu-derived Gam protein (Mu-GAM). While many base editors are designed to work in a very narrow window proximal to the PAM sequence, some useful base editing systems create a wide spectrum of single-nucleotide variants (somatic hypermutation) in a wider editing window, and are thus well suited to directed evolution applications. Examples of these base editing systems include targeted AID-mediated mutagenesis (TAM) and CRISPR-X, in which Cas9 is fused to activation-induced cytidine deaminase (AID).

In a preferred embodiment of the methods according to the present invention, said method is performed in vivo, for example in a cell, tissue or in a bacterium, fungus, plant or animal, or in vitro, in a sample. The sample can be a solid or liquid sample, and can be selected from a sample comprising cells, and an acellular in vitro sample. The cells are preferably plant cells or animal cells, such as mammalian cells, preferably human cells. The sample can be a biological sample, preferably obtained from a tissue sample, saliva, blood, plasma, sera, stool, urine, sputum, mucous, lymph, synovial fluid, cerebrospinal fluid, ascites, pleural effusion, seroma, pus, or swab of skin or a mucosal membrane surface. In one aspect, the cells, tissues and/or samples can be crude samples and/or wherein the one or more nucleic acid molecules are not purified or amplified from the sample prior to application of the methods. In another aspect, the cells, tissues and/or samples can be purified or partially purified (enriched) samples and/or the one or more nucleic acid molecules are purified or amplified from the sample prior to application of the methods. In another aspect, the cells can be part of an environmental sample such as air, a natural body of water (e.g. river, lake, ocean), wastewater, or soil.

The methods according to the present invention can be partially or fully automated, e.g. performed fully or in part by robots. The methods according to the present invention can involve the use of computers and respective databases for performing and/or analysis of the results as obtained.

In one aspect, several or even a multitude of target nucleic acids are analyzed in one or more samples, tissues and/or cells, and preferably in a multitude of samples, tissues and/or cells. In one aspect, several or even a multitude of sensed RNAs are detected in one or more samples, tissues and/or cells, and preferably in several or even a multitude of samples, tissues and/or cells.

In a preferred embodiment of the methods according to the present invention, more than one non-naturally occurring tracrRNAs are selected, designed, generated (produced, see above) and used, each specifically hybridizing with a different portion of said sensed RNA in one or more samples, tissues and/or cells, and preferably in several or even a multitude of samples, tissues and/or cells.

The present system could, for example, target anywhere from 2 to 7 genetic loci by cloning multiple tracrRNAs into a single plasmid. These multiplex tracrRNA vectors can conceivably be suitably combined with any of the aforementioned CRISPR nucleases in order be used in the aspects of the invention.

In a preferred embodiment of the methods according to the present invention, said at least one sensed RNA is single or initially double stranded. In the context of the present invention, a sensed RNA is any RNA of interest to be detected using the methods according to the present invention. Usually and preferably, the sensed RNA is a single-stranded RNA molecule, such as an mRNA or non-coding RNAs. The RNA can be of natural origin or artificially produced. The single stranded sensed RNA can be from a human cell, an animal cell, a plant cell, an immune cell, a cancerous cell, an infected cell, or a diseased cell, and/or can be derived from a virus, a parasite, a helminth, a fungus, a protozoan, a bacterium, or a pathogenic bacterium.

In a preferred embodiment of the methods according to the present invention, said at least one sensed RNA is derived from a virus selected from Zika virus, human immunodeficiency virus (HIV), hepatitis B virus, hepatitis C virus, herpes virus, coronavirus, influenza, herpes simplex virus I, herpes simplex virus II, papillomavirus, rabies virus, cytomegalovirus, human serum parvo-like virus, respiratory syncytial virus, varicella-zoster virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus, Sendai virus, feline leukemia virus, reovirus, polio virus, simian virus 40, mouse mammary tumor virus, dengue virus, rubella virus, west Nile virus, and yellow fever virus.

In a preferred embodiment of the methods according to the present invention, said at least one sensed RNA is derived from a pathogenic bacterium selected from *Mycobacterium tuberculosis, Streptococcus agalactiae*, methicillin-resistant *Staphylococcus aureus, Legionella pneumophila, Streptococcus pyogenes, Escherichia coli, Neisseria gonorrhoeae, Neisseria meningitidis*, Pneumococcus, *Cryptococcus neoformans, Treponema pallidum*, Lyme disease spirochetes, *Pseudomonas aeruginosa, Mycobacterium leprae*, and *Brucella abortus*.

In a preferred embodiment of the methods according to the present invention, the at least one sensed RNA is derived from a gene the transcription and/or expression thereof is modified in response to external factors, such as, for example, metabolic factors or signals, hormones, pathogens, toxins, drugs, ageing and/or biotic or abiotic stress.

In a preferred embodiment of the methods according to the present invention, the sensed RNAs are selected to be environment, species, strain, disease, cell- and/or tissue specific.

In this aspect, the methods of the invention help to identify and/or to group cells or organisms based on the sensed RNAs as selected. The at least one sensed RNA is preferably related to a condition selected from a viral infection, such as, for example, coronavirus infection, infection with a pathogen, a metabolic disease, cancer, neurodegenerative diseases, ageing, a drug, and biotic or abiotic stress.

In a preferred embodiment of the methods according to the present invention, the at least one sensed RNA can be added to said cell, tissue and/or sample prior to step a), and/or wherein said method further comprises at least one step selected from in vitro transcription of DNA into RNA, reverse transcription of RNA into DNA, and—optimally—subsequent in vitro transcription of said DNA into RNA. This can be done in order to provide suitable or desired signal amplification. Usually, the sensed RNA in said cell, tissue or sample is present in a range of from about 500 fM to about 1 uM, e.g. from about 500 fM to about 1 nM, preferably is present in a range of from about 1 pM to about 1 nM. Optimally, the method can detect a single molecule per cell, tissue and/or sample.

In another preferred embodiment of the methods according to the present invention, any tracrRNA-dependent CRISPR nuclease enzyme can be used, as long as it requires a tracrRNA for the binding function thereof as listed, for example, in Evolutionary classification of CRISPR-Cas systems: a burst of class 2 and derived variants (Nat Rev Microbiol. 2020; 18(2):67-83), the listing of which is incorporated herein by reference. Preferably, the nuclease is selected from type II Cas9 and type V Cas12 nuclease enzymes, as well as the recently identified CasX (now type V-E) (Liu et al. CasX enzymes comprise a distinct family of RNA-guided genome editors. Nature, 2019 February; 566 (7743): 218-223). Examples are type II Cas9 nuclease selected from the group consisting of II-A, —B, and —C, and type Cas12 nuclease selected from the group consisting of type V-B, —C, -D, -E, —F, -G, and -K. Usually, suitable plasmid systems are used in order to introduce and express Cas nucleases. Type V-A, which was identified as the first known type V system in the human pathogenic bacterium *Francisella tularensis* in 2013, has the signature effector protein Cas12a (formerly designated Cpf1). Shmakov et al. identified type V-B and type V-C in 2015, Harrington et al. identified type V-F in 2018, and Yan et al. identified type V-G, type V-H, and type V-I in 2019. By querying uncultivated bacteria in groundwater and sediment samples via genome-resolved metagenomics, Burstein and colleagues identified type V-D and type V-E in 2017 (Tong B, et al. The Versatile Type V CRISPR Effectors and Their Application Prospects. Front Cell Dev Biol. 2021 Feb. 4; 8:622103. doi: 10.3389/fcell.2020.622103. PMID: 33614630; PMCID: PMC7889808).

Deltcheva et al. (in: CRISPR RNA maturation by trans-encoded small RNA and host factor RNase III. *Nature.* 2011; 471(7340):602-607. doi:10.1038/nature09886) report that differential RNA sequencing of the human pathogen *Streptococcus pyogenes* uncovered tracrRNA, a trans-encoded small RNA with 24 nucleotide complementarity to the repeat regions of crRNA precursor transcripts. They show that tracrRNA directs the maturation of crRNAs by the activities of the widely conserved endogenous endoribonuclease RNase III and the CRISPR-associated Cas9 (Csn1) protein; all these components are found to be essential to protect *S. pyogenes* against prophage-derived DNA. The tracrRNA pairs with the repeat region, providing a substrate for RNase III. All examples of type V-B/C/E/F/G/K nucleases using sgRNAs are effectively relying on the tracrRNA. The cleaved RNA duplex is then bound by Cas9, and the crRNA portion directs the DNA targeting. Also, tracrRNAs have been identified in subtype V-B systems, although in this case, the cleavage enzyme remains uncharacterized (Liu L, Chen P, Wang M, Li X, Wang J, Yin M, Wang Y. 2017C2c1-sgRNA complex structure reveals RNA-guided DNA cleavage mechanism. *Mol. Cell* 65, 310-322).

In yet another preferred embodiment of the methods according to the present invention, the at least one tracrRNA-dependent CRISPR nuclease enzyme is modified, for example mutated, and/or a recombinant fusion protein. A given RNA targeting sequence will have additional sites throughout the genome where partial homology exists, or there could be multiple target nucleic acids, e.g. as part of an in vitro diagnostic, that resemble each other. These sites are called off-targets and need to be considered when designing an ncrRNA. In addition to optimizing RNA design, CRISPR specificity can also be increased through modifications to Cas9. If high specificity is crucial using the dual nickase approach to create a double nick-induced double strand break can be used, which can also be combined with HDR-mediated gene editing for specific gene edits. Another approach is the use of mutated Cas nucleases, called high fidelity enzymes. For example, phage-assisted continuous evolution (PACE) methods resulted in xCas9 3.7 which has 7 mutations found in the REC2, REC3, and PAM interacting domains and allows for expanded PAM recognition as well as increased specificity and lower off-target activity. Therefore, the tracrRNA-dependent CRISPR nuclease enzyme can be mutated in the PAM interacting domains in order to alter PAM-recognition. As another example, by screening *E. coli* cells transformed with a pooled library of SpCas9 variants, mutated variants can be identified, like the so-called Sniper-Cas, which has less off-target activity than wild type Cas9 (Directed evolution of CRISPR-Cas9 to increase its specificity. *Nat Commun.* 2018 Aug. 6; 9(1): 3048, Lee, J., Jung, M. h., Jeong, E., Lee, J. K. Using Sniper-Cas9 to Minimize Off-target Effects of CRISPR-Cas9 Without the Loss of On-target Activity Via Directed Evolution. *J. Vis. Exp.* (144), e59202, doi:10.3791/59202 (2019)).

Cas9, for example, can be fused with transcriptional repressors or activators, and targeting these dCas9 fusion proteins to the promoter region results in robust transcriptional repression (CRISPR interference, or CRISPRi) or activation (CRISPRa) of downstream target genes. The simplest dCas9-based activators and repressors consist of dCas9 fused directly to a single transcriptional activator (e.g. VP64) or repressor (e.g. KRAB). Additionally, activation strategies have been developed for more potent activation of target genes in mammalian cell, such as co-expression of epitope-tagged dCas9 and antibody-activator effector proteins (e.g. SunTag® system); dCas9 fused to several different activation domains in series (e.g. dCas9-VPR; or co-expression of dCas9-VP64 with a modified scaffold sgRNA and additional RNA-binding helper activators (e.g. SAM activators). Importantly, unlike the genome modifications induced by Cas9 or Cas9 nickase, dCas9-mediated gene activation or repression is reversible, since it does not permanently modify the genomic DNA. dCas9 has also been used for genome-wide screens to activate or repress gene expression in mice and human cells. Synthetic CRISPR-Cas gene activators have been developed for bacteria by using a scaffold RNA that contains the gRNA and an RNA hairpin to recruit activation proteins. CRISPRi can also been adapted for diverse bacterial species using a modular system called Mobile-CRISPRi. In this system, CRISPRi is introduced into bacteria using conjugation and stably integrated into the chromosome.

In another aspect of the methods according to the present invention, said first portion of said sensed RNA comprises a protospacer adjacent motif (PAM). As an example, for Cas12 nucleases, the PAM is present within the repeat portion upstream of the guide portion of the resulting ncrRNA, whereas for Cas9, the PAM is present in the repeat portion downstream of the guide portion of the ncrRNA. By selecting targets with the appropriate PAM, the generated crRNA can target its own site. This allows editing only if the gene is transcribed. This strategy greatly limits editing, for example to specific tissues, depending on the expression profile of the gene to be targeted.

As mentioned above, in a preferred embodiment of the methods according to the present invention, the sensed RNA and the non-naturally occurring tracrRNA create a dsRNA, and thus a dsRNA cleaving enzyme, such as RNase III enzyme recognition site or domain. An ssRNA cleaving enzyme, such as RNase A, can also be applied to promote further processing or clear RNAs not converted into ncrRNAs. Preferably, said dsRNA cleaving enzyme substrate in said sensed RNA has a length of 10 or more nucleotides, such as up to about 50 nucleotides or even more, preferably of 11 and more nucleotides, and more preferred of about 12 nucleotides or more. Preferred ranges are between 9 and 15 nucleotides, more preferred 10 to 14 nucleotides, and most preferred 12 nucleotides.

In another aspect, the portions of the nucleic acid molecules as used in the methods of the present invention that hybridize are complementary to at least 80%, preferably complementary to more than 90%, more preferably to more than 95%, and most preferably are 100% complementary to each other. As discussed above, it was surprisingly found that ncrRNAs can deviate from traditional crRNAs, indicating the "robustness" of the system with respect to the stem-like secondary structure basically mimicking the original repeat:anti-repeat stem, and a particular focus was put on the base stem bound by Cas9 and Cas12 (see FIGS. 20-25). The results show that bulges can be tolerated to quite some degree, especially when the bulge is smaller, away from the base of the stem, or on the repeat side. A very similar result was found when accommodating some mismatches in the stem. Therefore, the nucleotide sequence of said at least one portion of said tracrRNA that specifically hybridizes with a first portion of said sensed RNA can be produced and/or modified in order to be complementary to at least 80%, preferably complementary to more than 90%, more preferably to more than 95%, and most preferably are 100% complementary to said first portion to said sensed RNA.

In another aspect of the methods according to the present invention, said methods, at least in part, comprise a quantitative analysis. Preferred is therefore a step comprising detecting the amount of the at least one target nucleic acid as modified, e.g. the products cleaved and/or edited and/or said at least one sensed RNA, as well as the bound target nucleic acid in said sample, tissue and/or cell. Preferably the amount per sample, tissue and/or cell is determined, when compared to a control. Quantification assays are known to the person of skill, and may include absorbance (e.g. UV, spectrophotometry) and/or fluorescence assays, and real-time PCR. The assays can quantify the amount(s) and/or ratios of the nucleic acid(s) as quantified (modified at least one target nucleic acid and/or said at least one sensed RNA) as a single value (e.g. as the result or at the "end" of the assay as used) or can monitor changes over time in the nucleic acids, i.e. preferably further comprising detecting a change in the amount of said modification of said at least one target nucleic acid (e.g. the products cleaved and/or edited) and/or said at least one sensed RNA in said sample, tissue and/or cell, in particular when compared to a control.

In yet another aspect of the methods according to the present invention, multiple labels and/or markers are used. Markers can be used both for the nucleic acid molecules that form part of the assays, as well as the protein components (e.g. nuclease and/or fusions). Labels and markers can be included into the components of the assays (in particular the nucleic acids and/or the proteins), as well as constitute moieties that are attached, either covalently or non-covalently.

Another aspect of the present invention then relates to a method for detecting a medical condition in a cell, tissue or organism, such as a mammal, preferably a human, wherein said condition is related to the presence of, expression of and/or mutation(s) in at least one sensed RNA. The method comprises performing the method according to the invention as above, and detecting said medical condition based on the presence of, expression of and/or mutation(s) in said at least one sensed RNA as detected. The medical conditions that can be detected using the present invention are those that are related to the at least one sensed RNA molecule. As explained above, the sensed RNA can either itself constitute the origin of the condition or disease, for example in case of infections, e.g. viral, such as, for example, coronavirus infection, bacterial and/or fungal infections of the cells, tissues and/or samples as tested. Other conditions may relate more indirectly to the at least one sensed RNA molecule, for example in case of an RNA that is aberrantly transcribed (present or found), expressed, processed (e.g. splicing) and/or mutated. The sensed RNA molecule can be present in an increased or decreased amount when compared to a healthy control (e.g. a control based on a group of healthy or diseased samples).

In a preferred embodiment of the methods according to the present invention, said at least one sensed RNA is single or initially double stranded. The single stranded sensed RNA can be/relates to from a human cell, an animal cell, a plant cell, an immune cell, a cancerous cell, an infected cell, or a diseased cell, and/or can be derived from a virus (see above), a parasite, a helminth, a fungus, a protozoan, a bacterium, or a pathogenic bacterium (see above). In a preferred embodiment of the methods according to the present invention, the at least one sensed RNA is derived from/related to a gene the transcription and/or expression thereof is modified in response to external factors, such as, for example, metabolic factors or signals, hormones, pathogens, toxins, drugs, ageing and/or biotic or abiotic stress. Consequently, the at least one sensed RNA is preferably related to a condition selected from a viral infection, such as, for example, coronavirus infection, infection with a pathogen, a metabolic disease, cancer, neurodegenerative diseases, ageing, a drug, and biotic or abiotic stress). Usually, the presence of or the increased or decreased amount of the sensed RNA is indicative for the presence of said disease or condition. Another aspect of the method relates to a monitoring of the amount or presence of said sensed RNA during a treatment of said individual, patient or organism, in particular the individual, patient or organism from which the cell, tissue and/or sample has been obtained.

In yet another aspect of the present invention, the methods of the present invention comprise a step wherein said one or more sensed RNAs are detected as (part of) a set of RNAs constituting a gene signature (i.e. a set of sensed RNAs that is specific for an organism, a cell and/or tissue). The method thus detects one or more gene signatures, wherein each gene signature identifies an organism, a cell and/or tissue, such as a plant, animal or microbial species, one or more plant, animal or microbial phenotypes, or both. In turn, the methods of the present invention can be used to identify a set of RNAs constituting a gene signature, e.g. an expression profile for one or more sensed RNAs, wherein said signature is specific for an organism, a cell and/or tissue, such as a plant, animal or microbial species, one or more plant, animal or microbial phenotypes, or both (see also above for transcriptional recording).

Examples for preferred in vitro diagnostic formats for methods of the present invention are microarrays, in particular with double-stranded DNA to monitor many DNAs at once, and lateral flow assays. Lateral flow assays are known to the person of skill, and operate on the same principles as enzyme-linked immunosorbent assays (ELISA). In essence, these tests run the liquid sample along the surface of a pad with reactive molecules that show a visual positive or negative result.

As mentioned above, in a preferred embodiment of the methods according to the present invention, the at least one sensed RNA can be added to said cell, tissue and/or sample prior to step a), and/or wherein said method further comprises at least one step selected from in vitro transcription of DNA into RNA, reverse transcription of RNA into DNA, and—optimally—subsequent in vitro transcription of said DNA into RNA. This can be done in order to provide suitable or desired signal amplification. Usually, the sensed RNA in said cell, tissue or sample is present in a range of from about 500 fM to about 1 uM, e.g. from about 500 fM to about 1 nM, preferably is present in a range of from about 1 pM to about 1 nM. Optimally, the method can detect a single molecule per cell, tissue and/or sample.

Yet another aspect of the present invention then relates to a method for treating a disease or medical condition in a cell, tissue or organism, such as a mammal, preferably a human, wherein said condition is related to the presence of, expression of and/or mutation(s) in at least one sensed RNA. The method comprises providing a suitable treatment to said cell, tissue or organism, in particular a specific medical treatment, performing the method according to the invention as above, and modifying said treatment of said disease or medical condition based on the presence of, expression of and/or mutation(s) in said at least one sensed RNA as detected. The medical conditions that can be detected using the present invention are those that are related to the at least one sensed RNA molecule. As explained above, the sensed RNA can either itself constitute the origin of the condition or disease, for example in case of infections, e.g. viral, such as, for example, coronavirus infection, bacterial and/or fungal infections of the cells, tissues and/or samples as tested. Other conditions may relate more indirectly to the at least one sensed RNA molecule, for example in case of an RNA that is aberrantly transcribed (present or found), expressed, processed and/or mutated. The sensed RNA molecule can be present in an increased or decreased amount when compared to a healthy control (e.g. a control based on a group of healthy or diseased samples).

In a preferred embodiment of the methods according to the present invention, said at least one sensed RNA is single or initially double stranded. The single stranded sensed RNA can be/relates to from a human cell, an animal cell, a plant cell, an immune cell, a cancerous cell, an infected cell, or a diseased cell, and/or can be derived from a virus (see above), a parasite, a helminth, a fungus, a protozoan, a bacterium, or a pathogenic bacterium (see above). In a preferred embodiment of the methods according to the present invention, the at least one sensed RNA is derived from/related to a gene the transcription and/or expression thereof is modified in response to external factors, such as, for example, metabolic factors or signals, hormones, pathogens, toxins, drugs, ageing and/or biotic or abiotic stress. Consequently, the at least one sensed RNA is preferably related to a condition selected from a viral infection, such as, for example, coronavirus infection, infection with a pathogen, a metabolic disease, cancer, neurodegenerative diseases, ageing, a drug, and biotic or abiotic stress). Usually, the presence of or the increased or decreased amount of the sensed RNA is indicative for the presence of said disease or condition. Another aspect of the method relates to a monitoring of the amount or presence of said sensed RNA during a treatment of said individual, patient or organism, in particular the individual, patient or organism from which the cell, tissue and/or sample has been obtained.

For medical treatments, reprogrammed tracrRNAs would provide a quantitative readout of specific RNAs of interest in a patient sample that would directly inform the course of treatment. For instance, reprogrammed tracrRNAs can be used to detect viral sequences in a blood draw or sputum to determine the specific virus infecting the patient such as, for example, coronavirus infection. The identified virus would directly inform the course of treatment. For instance, identifying rhinovirus would result in a more modest treatment plan involving fluids and rest, whereas identifying coronavirus would require close monitoring and containment, while identifying ebola would require immediate medical intervention. Similarly, reprogrammed tracrRNAs can be used to detect specific RNAs in a cancer biopsy to identify key markers of cancer progression and drug susceptibilities. This information would in turn inform the doctor how to proceed with the course of treatment. Finally, reprogrammed tracrRNAs could be used with a sample containing an infecting bacterial or fungal pathogen (e.g. Clostridioides *difficile* in a stool sample, *Pseudomonas aeruginosa* in a sputum sample) to identify specific markers of antibiotic resistance to determine the best regime of antibiotics to administer to a patient.

An embodiment of the above described method for treating a disease or medical condition in a cell, tissue or organism, such as a mammal, preferably a human, wherein said condition is related to the presence of, expression of and/or mutation(s) in at least one sensed RNA, in particular a viral RNA or DNA, reprogrammed (e.g. specific for a virus target nucleic acid) tracrRNAs according to the invention are be used to detect viral sequences in a blood draw or sputum to determine the specific virus, such as, for example, coronavirus, infecting the patient. The attending physician then treats the viral infection as detected with antiviral chemotherapeutics and/or biologics. In the course of the treatment, the reprogrammed tracrRNAs provides a quantitative readout of specific RNAs of interest in the patient sample that would directly inform about the course and effect/success of the treatment. The attending physician will then adjust the treatment accordingly, i.e. provide more with antiviral chemotherapeutics and/or biologics, if required. This treatment schedule can be repeated, if required.

Also, identifying a virus like rhinovirus can result in a more modest treatment plan involving fluids and rest, whereas identifying coronavirus would require close monitoring and containment, while identifying ebola would require immediate medical intervention. Similarly, similarly as above, reprogrammed tracrRNAs (e.g. specific for a cancer target nucleic acid) can be used to detect specific RNAs in a cancer biopsy to identify key markers of cancer progression and drug susceptibilities. This information would in turn inform the doctor how to proceed with the course of treatment.

Finally, again similarly as above, reprogrammed tracrRNAs (e.g. specific for a bacterial or fungal target nucleic acid) could be used with a sample containing an infecting bacterial or fungal pathogen (e.g. Clostridioides *difficile* in a stool sample, *Pseudomonas aeruginosa* in a sputum sample) to identify specific markers of antibiotic resistance to determine the best regime of antibiotics to administer to a patient.

In another preferred aspect thereof, the object of the present invention is solved by providing a non-naturally occurring tracrRNA nucleic acid molecule, comprising an anti-repeat region sequence that is designed to specifically hybridize to a preselected sensed RNA sequence through forming a complex that mimics the natural crRNA: tracrRNA duplex. The non-naturally occurring tracrRNA nucleic acid molecule may be part of a complex comprising the non-naturally occurring tracrRNA nucleic acid molecule according to the present invention, at least one tracrRNA-dependent CRISPR nuclease enzyme, and at least one sensed RNA., and may be further bound to a target DNA nucleic acid molecule comprising a sequence based or designed based on the at least one sensed RNA sequence.

Thus, the non-naturally occurring tracrRNA nucleic acid molecule may be part of a complex comprising the non-naturally occurring tracrRNA nucleic acid molecule according to the present invention, at least one tracrRNA-dependent CRISPR nuclease enzyme, and at least one sensed RNA, and may be further bound to a target DNA nucleic acid molecule comprising a sequence based or designed based on the at least one sensed RNA sequence.

In the context of the present invention, the non-naturally occurring tracrRNA nucleic acid molecule comprises an anti-repeat region sequence that is designed to specifically hybridize to a preselected sensed RNA sequence through forming a complex that mimics the natural crRNA: tracrRNA duplex. This shall mean that the non-naturally occurring tracrRNA nucleic acid molecule and the preselected sensed RNA sequence molecule form a duplex that structurally resembles the consensus structure of crRNA: tracrRNA duplexes as disclosed in the literature. For example, the crRNA:tracrRNA duplex may form a lower stem, bulge, and upper stem modules for Cas9, lower stem and upper stem modules for Cas12b, and a stem and triple helix for Cas12e. The crRNA contains the spacer module, and the tracrRNA contains the nexus and terminal hairpins (see, for example, Briner A E, et al. Guide RNA functional modules direct Cas9 activity and orthogonality. Mol Cell. 2014 Oct. 23; 56(2):333-339. doi: 10.1016/j.molcel.2014.09.019. Epub 2014 Oct. 16. PMID: 25373540, or Crawley, A. B., Henriksen, E. D., Stout, E. et al. Characterizing the activity of abundant, diverse and active CRISPR-Cas systems in lactobacilli. Sci Rep 8, 11544 (2018). https://doi.org/10.1038/s41598-018-29746-3).

In another preferred aspect thereof, the object of the present invention is solved by providing a detection system for a sensed RNA comprising a) a non-naturally occurring tracrRNA designed to bind to at least one portion of said sensed RNA, said sensed RNA further comprising a portion that specifically hybridizes with a first portion of a target nucleic acid, and b) at least one tracrRNA-dependent CRISPR nuclease enzyme. Preferred is a detection system for the parallel detection of several sensed RNAs in parallel, comprising a set of several non-naturally occurring tracrRNAs for said several sensed RNAs. Another detection system comprises several non-naturally occurring tracrRNAs that hybridize at several positions on one sensed RNA.

This aspect of the present invention provides the components, e.g. non-naturally occurring tracrRNA nucleic acid molecule according to the invention as above, for performing the methods according to the invention as a detection system, for example as a part of a diagnostic kit. Preferably, said detection system is provided in one or more containers, and comprises suitable enzymes, buffers, and excipients, as well as instructions for use. The components can be—at least in part—immobilized on a substrate, wherein said substrate can be exposed to said cell, tissue and/or sample. The detection system can be applied to multiple discrete locations on said substrate, such as a flexible materials substrate, for example a chip. The flexible materials substrate can be a paper substrate, a fabric substrate, or a flexible polymer-based substrate.

Examples for preferred in vitro diagnostic formats for methods of the present invention are microarrays, in particular with double-stranded DNA to monitor many DNAs at once, and lateral flow assays. Lateral flow assays are known to the person of skill, and operate on the same principles as enzyme-linked immunosorbent assays (ELISA). In essence, these tests run the liquid sample along the surface of a pad with reactive molecules that show a visual positive or negative result.

In another preferred aspect thereof, the object of the present invention is solved by providing the use of the non-naturally occurring tracrRNA nucleic acid molecule or the sensed RNA detection system according to the aspect as above for performing a method according to any one of the aspects as above, in particular for detecting a sensed RNA, a viral sensed RNA, a sensed RNA transcribed from a disease marker, and/or for generating an expression profile for one or more sensed RNAs as mentioned above.

The examples described herein can be used for wide-ranging applications, such as diagnosing medical conditions to inform the course of treatment, identifying SNPs associated with health outcomes or disease, such as in acute sepsis, determining the identity of pathogen, virulence factors, resistance markers, SNPs, viral detection, i.e. the identity, and/or viral variants (see, for example, SARS CoV-2 as disclosed herein), cancer diagnostics, in cancer samples, such as biopsies, determining mutations, and/or SNPs, identifying microbial contaminants in potable water, identifying viral or microbial contaminants in fermentations or cell cultures, identifying plant or insect variants, or identifying key microbial members in mixed communities (e.g. in the gut, soil, water), such as analysis of microbiomes and/or microbial sentinels (i.e. commensal bacteria that serve as reporters for non-invasive measurements), in particular the identity, relative abundance, resistance markers, metabolic genes, phylum/genus/species/strain-specific genes, and the like, and the tracking of viral or bacterial spread in vivo, such as in whole organisms, or based on samples, for example taken from the environment (e.g. spread of viruses or resistant bacteria detected in waste water samples, etc.).

In the context of the present invention, unless explicitly mentioned otherwise, the term “about” shall mean a value as given+/−10%.

Starting from the characterization of a native CRISPR-Cas9 system in the bacterial pathogen *C. jejuni*, the inventors found that cellular transcripts can be converted into non-canonical crRNAs through hybridization with the tracrRNA. This discovery adds ncrRNAs to the list of RNA guides found in nature, including crRNAs, small CRISPR-Cas associated RNAs (scaRNAs) that similarly pair with the tracrRNA anti-repeat, and “natural” sgRNAs formed through upstream transcription of the tracrRNA. Importantly, these prior examples are all encoded within CRISPR-Cas loci.

The inventors further demonstrated that non-natural tracrRNAs can link the presence of an RNA-of-interest to sequence-specific DNA targeting by Cas9. The RNA-of-interest otherwise had no association with the Cas9 or the CRISPR-Cas system. Thereby, non-natural tracrRNAs enable in vivo applications with Cas9 such as multiplexed transcriptional recording or transcription-dependent editing. The most immediate application involves multiplexed RNA detection in vitro through LEOPARD, as disclosed herein. In a preferred embodiment, LEOPARD adds to the existing CRISPR diagnostic platforms based on Cas12a or Cas13 while offering scalable multiplexing in a single reaction and the first diagnostic platform involving Cas9.

The inventors' reliance on gel electrophoresis provided a proof-of-principle demonstration of multiplexed detection. More advanced implementations are also possible though, such as existing technologies based on microarrays or next-generation sequencing chips associate DNA sequences with specific spatial locations, potentially scaling up to millions of targets monitored in parallel. Either approach will enhance assay sensitivity due to the limited number of DNA molecules in a given cluster, with the detection of sensed RNAs well below the 40 nM used in the exemplary gel-based assays. DNA targets linked to fluorophores with distinct spectra and cleavable quenchers can also be employed as sequence-specific and scalable readouts.

Incorporating isothermal pre-amplification similar to existing CRISPR diagnostics will also offer a means to enhance sensitivity. With further development, LEOPARD will become a powerful diagnostic tool not only for viral detection but also for other applications requiring multiplexed readouts, such as screening for cancer mutations, identifying pathogens and antibiotic-resistance markers, or determining gene expression profiles for drug susceptibility, as also discussed herein.

Herein, non-natural tracrRNAs were exemplary established with Cas9, and Cas12 nucleases that also rely on tracrRNAs (see also FIGS. 9 to 11, and 22 to 25). Extending tracrRNA reprogramming to these and other nucleases know to the person of skill and as described herein expands the available repertoire of nucleases and incorporate their unique attributes, such as signal amplification or programmable transposition.

Figure 18:
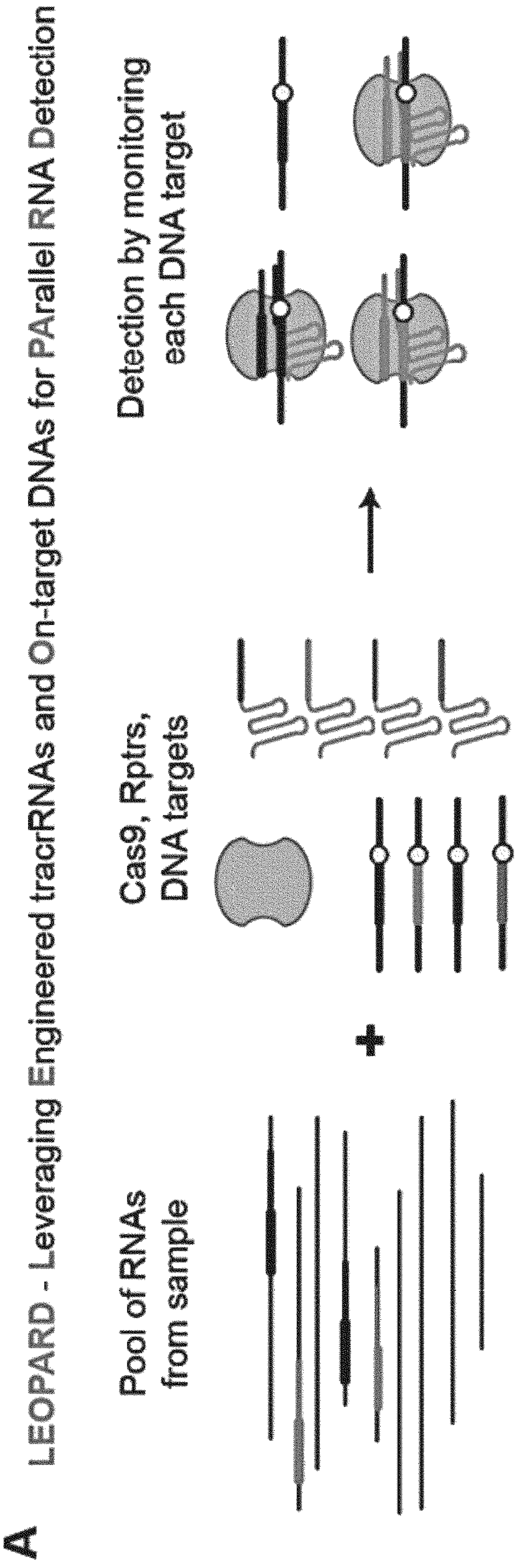
Figure 18:
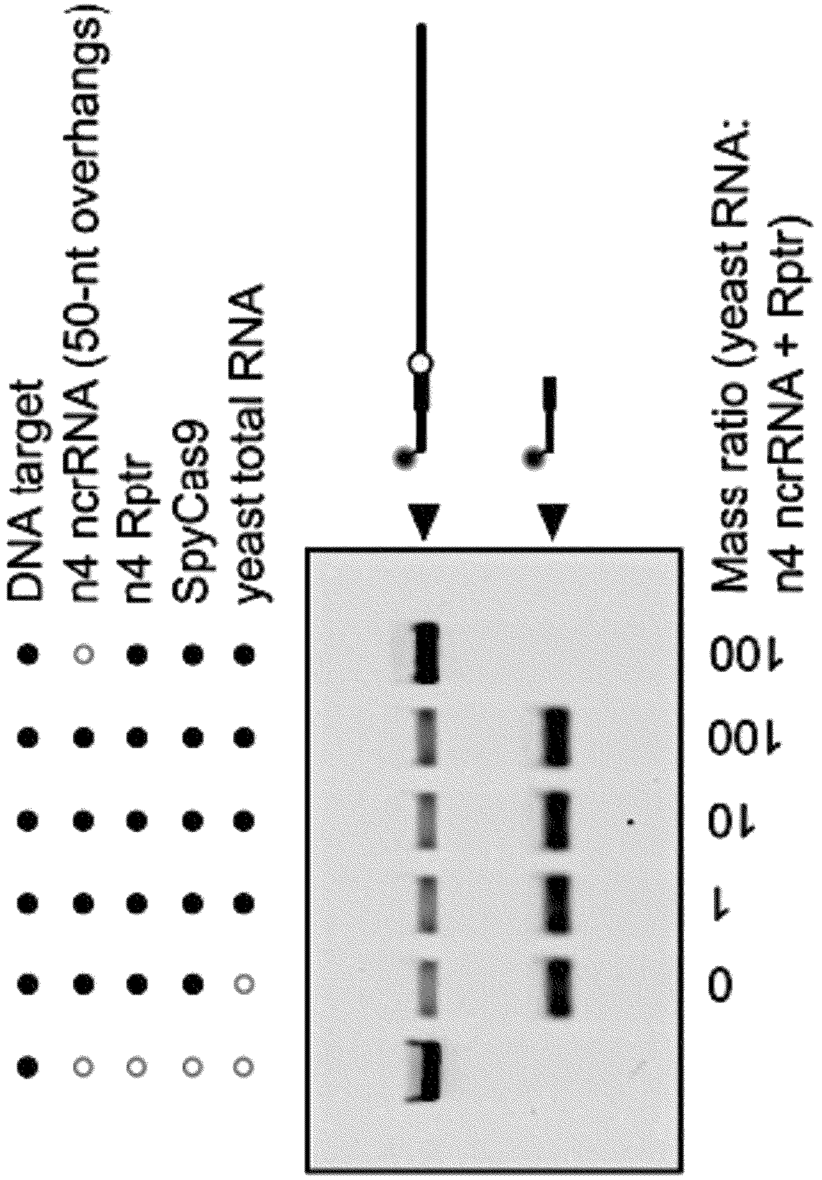
Figure 18:
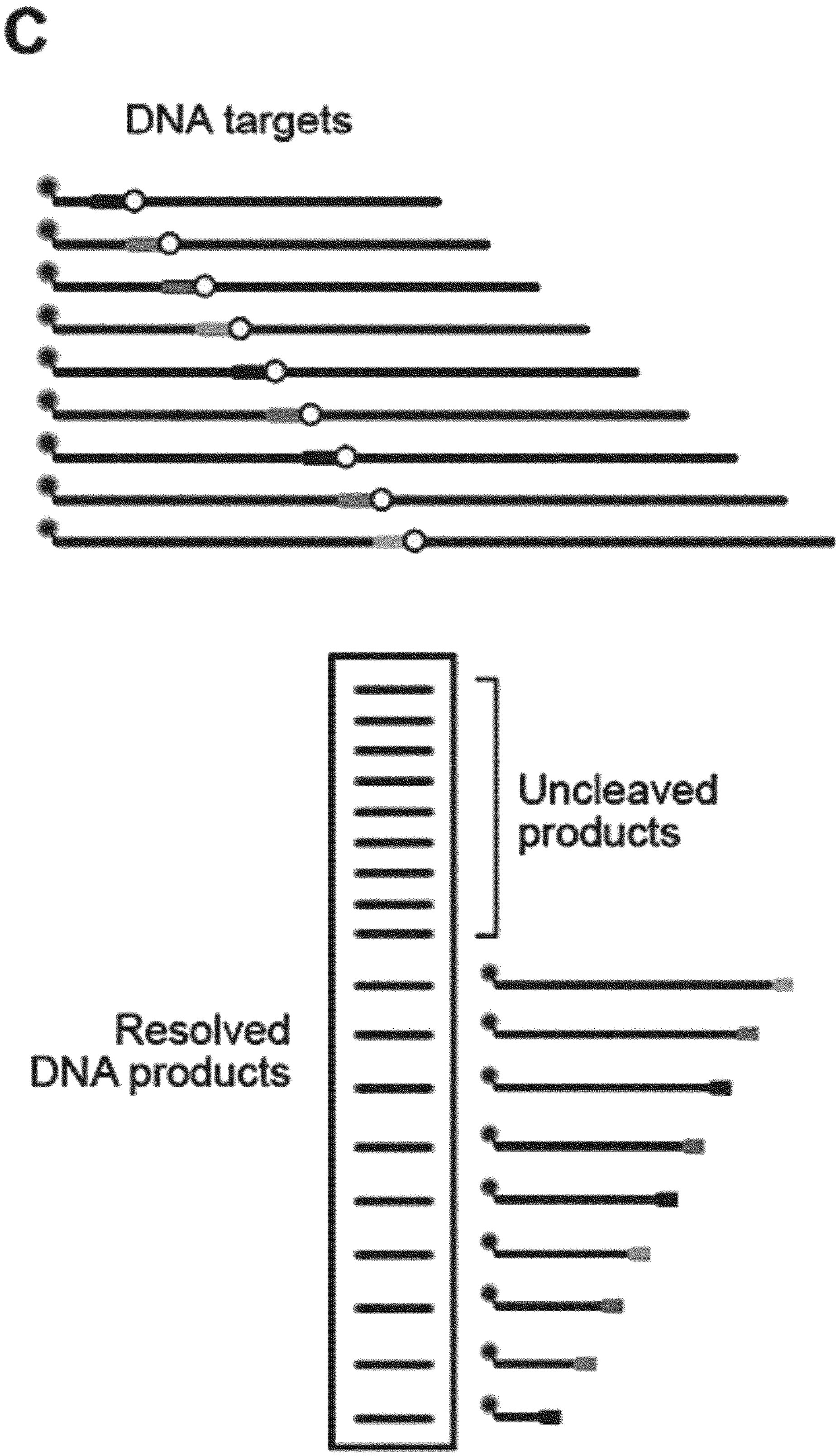
Figure 18:
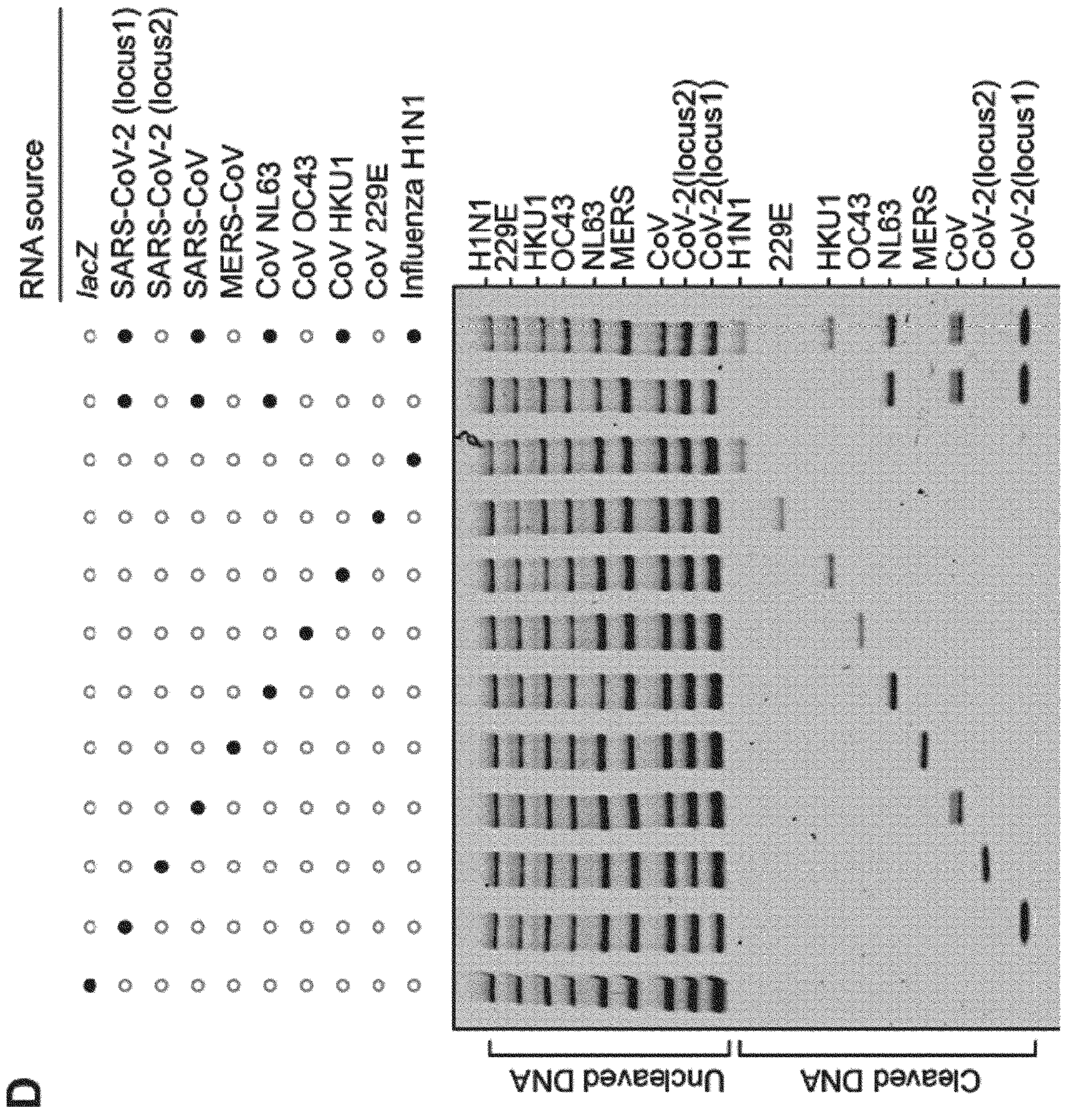
Figure 18:
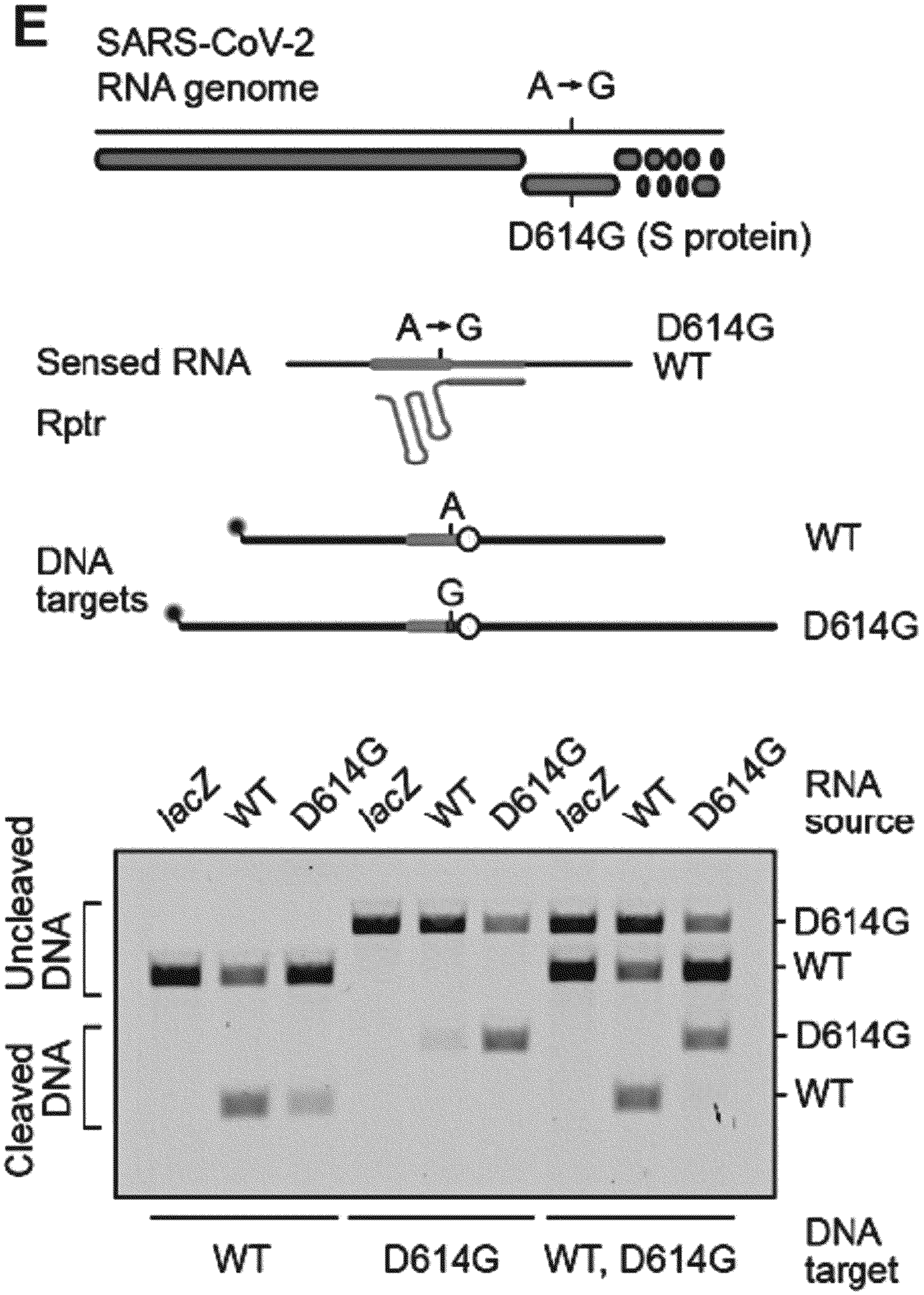

While systematically perturbing the standard crRNA: tracrRNA duplex, the inventors found that many deviations—particularly outside of the 5' end of the repeat—were tolerated by Cas9 and Cas12 and still led to targeting of designed DNA targets. However, despite this promiscuity, targeting is still determined by the upstream guide sequence and the requirement for a flanking PAM. Thus, both anti-repeat hybridization and guide-dependent DNA targeting limit the potential of off-targeting. Correspondingly, the inventors did not observe any detectable off-targeting when assessing multiple viral RNAs or introducing yeast total RNA with LEOPARD (FIG. 18 B, D). Design rules for non-natural tracrRNAs that account for potential off-targeting as well as on-target activity, similar to existing sgRNA design algorithms help advance the conversion of any RNA into a sequence-specific guide for CRISPR technologies.

As stated herein, the present invention particularly relates to the following items.

Item 1. A non-naturally occurring tracrRNA nucleic acid molecule, comprising an anti-repeat region sequence that is designed to specifically hybridize to a preselected sensed RNA sequence through forming a complex that mimics the natural crRNA:tracrRNA duplex.

Item 2. A complex comprising the non-naturally occurring tracrRNA nucleic acid molecule according to Item 1, at least one tracrRNA-dependent CRISPR nuclease enzyme, and at least one sensed RNA.

Item 3. The non-naturally occurring tracrRNA nucleic acid molecule according to Item 2, further bound to a target DNA nucleic acid molecule comprising a sequence based or designed based on the at least one sensed RNA sequence.

Item 4. A method for detecting at least one sensed RNA in a cell, tissue, and/or sample, said method comprising: a) contacting said sample with at least one non-naturally occurring tracrRNA comprising a portion that specifically hybridizes with a first portion of said sensed RNA, wherein a second portion of said sensed RNA specifically hybridizes with at least one target nucleic acid, in particular DNA, RNA, or ssDNA; wherein said at least one non-naturally occurring tracrRNA is hybridized or is able to be hybridized with said sensed RNA in the presence of at least one tracrRNA-dependent CRISPR nuclease enzyme, optionally further comprising the presence of a dsRNA-cleaving enzyme, such as RNase III; b) detecting binding of said at least one tracrRNA-dependent CRISPR nuclease enzyme to said at least one nucleic acid DNA; c) wherein binding detects said at least one sensed RNA in said cell, tissue and/or sample.

Item 5. The method according to Item 4, wherein said nuclease is inactivated in its cleaving and/or nicking activity.

Item 6. A method for detecting at least one sensed RNA in a cell and/or sample, said method comprising: a) contacting said sample with at least one non-naturally occurring tracrRNA comprising a portion that specifically hybridizes with a first portion of said sensed RNA, wherein a second portion of said sensed RNA specifically hybridizes with at least one target nucleic acid; wherein said at least one non-naturally occurring tracrRNA is hybridized or is able to be hybridized with said sensed RNA in the presence of at least one tracrRNA-dependent CRISPR nuclease enzyme, optionally further comprising the presence of a dsRNA-cleaving enzyme, such as RNase III; b) detecting cleavage of said at least one target nucleic acid in said sample by said nuclease enzyme; c) wherein detecting said cleavage of at least one target nucleic acid detects said at least one sensed RNA in said cell, tissue and/or sample.

Item 7. The method according to any one of Items 4 to 6, wherein detecting said bound and/or cleaved at least one target nucleic acid comprises detecting a change in the signal of a suitable label, such as a dye, a fluorophore, or electrical conductivity, and/or detecting the said cleaved at least one target nucleic acid fragment itself.

Item 8. A method for detecting at least one sensed RNA in a cell, tissue and/or sample, said method comprising: a) contacting said sample with at least one non-naturally occurring tracrRNA comprising a portion that specifically hybridizes with a first portion of said sensed RNA, wherein a second portion of said sensed RNA specifically hybridizes with at least one target nucleic acid; wherein said least one non-naturally occurring tracrRNA is hybridized or is able to be hybridized with said sensed RNA in the presence of at least one tracrRNA-dependent CRISPR nuclease enzyme, optionally further comprising the presence of a dsRNA-cleaving enzyme, such as RNase III; and b) nicking or cleaving of said at least one target nucleic acid in said sample by said nuclease, c) detectably editing said at least one target nucleic acid comprising, for example, non-homologous end joining (NHEJ) repair, microhomology-mediated end joining (MMEJ), homologous-directed repair (HDR), base editing, or prime editing and d) suitably detecting said editing of said at least one target nucleic acid comprising, for example, at least one method selected from detecting the presence and/or length of indels or gene edits, the activation/repression of a gene or other genetic element as encoded by said at least one target nucleic acid, and/or the detection of said prime or base editing; e) wherein detecting said editing of said at least one target nucleic acid detects said at least one sensed RNA in said cell, tissue and/or sample.

Item 9. The method according to any one of Items 4 to 8, wherein said method is performed in vivo or in vitro.

Item 10. The method according to any one of Items 4 to 9, wherein said sample is selected from a sample comprising cells, and an acellular in vitro sample, wherein said cells are preferably plant cells or animal cells, such as mammalian cells, preferably human cells.

Item 11. The method according to any one of Items 4 to 10, wherein several or a multitude of sensed RNAs are detected in one or more samples, tissues and/or cells.

Item 12. The method according to any one of Items 4 to 11, wherein said at least one sensed RNA is single stranded.

Item 13. The method according to any one of Items 4 to 12, wherein said at least one sensed RNA is environment, species, strain, disease, cell- and/or tissue specific or related to a condition selected from a viral infection, such as, for example, coronavirus infection, infection with a pathogen, a metabolic disease, cancer, neurodegenerative diseases, ageing, a drug, and biotic or abiotic stress.

Item 14. The method according to any one of Items 4 to 13, wherein said at least one sensed RNA is added to said cell, tissue and/or sample prior to step a), and/or further comprising a step of transcribing DNA into sensed RNA prior to step a).

Item 15. The method according to any one of Items 4 to 14, wherein said at least one tracrRNA-dependent CRISPR nuclease enzyme is selected from type II Cas9 and type V Cas12 nuclease enzymes, such as type II Cas9 nuclease selected from the group consisting of II-A, —B, and —C, and type Cas12 nuclease selected from the group consisting of type V-B, —C, -D, -E, —F, -G, and -K.

Item 16. The method according to any one of Items 4 to 15, wherein said at least one tracrRNA-dependent CRISPR nuclease enzyme is a recombinant fusion protein.

Item 17. The method according to any one of Items 4 to 16, wherein said portion of said at least one non-naturally occurring tracrRNA that specifically hybridizes with said first portion of said sensed RNA hybridizes with 10 or more nucleotides, preferably with 11 and more nucleotides, and more preferred with about 12 nucleotides or more.

Item 18. The method according to any one of Items 4 to 17, wherein said first portion of said sensed RNA comprises a protospacer adjacent motif (PAM).

Item 19. The method according to any one of Items 4 to 18, wherein said non-naturally occurring tracrRNA furthermore comprises at least one portion hybridizing with said sensed RNA providing a dsRNA cleaving enzyme substrate.

Item 20. The method according to Item 19, wherein said substrate of a dsRNA-cleaving enzyme in said sensed RNA has a length of 10 or more nucleotides, preferably of 11 and more nucleotides, and more preferred of about 12 nucleotides or more.

Item 21. The method according to any one of Items 4 to 20, wherein said portions that hybridize are complementary to at least 80%, preferably complementary to more than 90%, more preferably to more than 95%, and most preferably are 100% complementary.

Item 22. The method according to any one of Items 4 to 21, wherein the nucleotide sequence of said at least one portion of said tracrRNA that specifically hybridizes with a first portion of said sensed RNA is produced and/or modified in order to be complementary to at least 80%, preferably complementary to more than 90%, more preferably to more than 95%, and most preferably are 100% complementary to said first portion to said sensed RNA.

Item 23. The method according to any one of Items 4 to 22, wherein more than one non-naturally occurring tracrRNA are generated and used that each specifically hybridize with a different portion of said sensed RNA.

Item 24. The method according to any one of Items 4 to 23, further comprising detecting the amount of said at least one target nucleic acid and/or said at least one sensed mRNA in said sample, tissue and/or cell, preferably the amount per sample, tissue and/or cell.

Item 25. The method according to Item 24, further comprising detecting a change in the amount of said at least one target nucleic acid and/or said at least one sensed mRNA in said sample, tissue and/or cell when compared to a control.

Item 26. The method according to any one of Items 8 to 25, wherein the length of said indels as detected is between 1 to 14, and more preferable between 5 to 9 nucleotides, and wherein optionally said indels can be detected through sequencing and/or qPCR.

Item 27. The method according to any one of Items 4 to 26, wherein multiple labels and/or markers are used.

Item 28. A method for detecting a medical condition in a mammal, wherein said condition is related to the presence of, expression of and/or mutation(s) in at least one sensed RNA, comprising performing the method according to any one of Items 4 to 27, and detecting said medical condition based on the presence of, expression of and/or mutation(s) in said at least one sensed RNA as detected.

Item 29. The method according to Item 25, wherein said at least one sensed RNA is environment, species, strain, disease, cell- and/or tissue specific or related to a condition selected from a viral infection, such as, for example, coronavirus infection, infection with a pathogen, a metabolic disease, cancer, neurodegenerative diseases, ageing, a drug, and biotic or abiotic stress.

Item 27. The method according to Item 25 or 26, wherein said at least one sensed RNA is added to said cell, tissue and/or sample prior to step a), and/or further comprising a step of transcribing DNA into sensed RNA prior to step a).

Item 28. A sensed RNA detection system comprising a) a non-naturally occurring tracrRNA designed to bind to at least one portion of said sensed RNA, said sensed RNA further comprising a portion that specifically hybridizes with a first portion of a target nucleic acid, and b) at least one tracrRNA-dependent CRISPR nuclease enzyme.

Item 29. The sensed RNA detection system according to Item 28, further comprising c) at least one target nucleic acid molecule comprising a label for detecting cleavage of said target nucleic acid.

Item 30. The sensed RNA detection system according to Item 28 or 29, further comprising d) at least one dsRNA cleaving enzyme, such as RNase III enzyme.

Item 31. The sensed RNA detection system according to any one of Items 28 to 30, wherein at least one of said components a) to d) is encoded on a nucleic acid vector system.

Item 32. Use of the sensed RNA detection system according to any one of Items 28 to 31 for performing a method according to any one of Items 1 to 26, in particular for detecting a sensed RNA, a viral sensed RNA, a sensed RNA transcribed from a disease marker, or for generating an expression profile for one or more sensed RNAs.

The present invention will now be further described in the following examples with reference to the accompanying Figures, nevertheless, without wanting to be limited thereto.

For the purposes of the present invention, all references as cited herein are incorporated by reference in their entireties. The present disclosure includes as sequence listing comprising SEQ ID Nos: 1 to 128 as part of the description, which is also incorporated by reference in its entirety.

In the figures, the non-naturally occurring tracrRNA according to the present invention is sometimes referred to as "rptr".

FIG. 1 shows the discovery of non-canonical crRNAs. A) Depiction of the identification of RNAs that co-immunoprecipitate with Cas9 in *Campylobacter jejuni* CG8421. B) A set of 47 RNAs enriched as part of co-immunoprecipitation shared a motif complementary to the anti-repeat portion of the tracrRNA. The ensuing RNAs resembled crRNAs but were derived from RNAs encoded outside of the CRISPR-Cas system. C) Elucidated mechanism for the generation of non-canonical crRNAs (ncrRNAs). This mechanism should apply to any tracrRNA-dependent CRISPR nuclease. The tracrRNA as shown is SEQ ID NO: 97.

Figure 3:
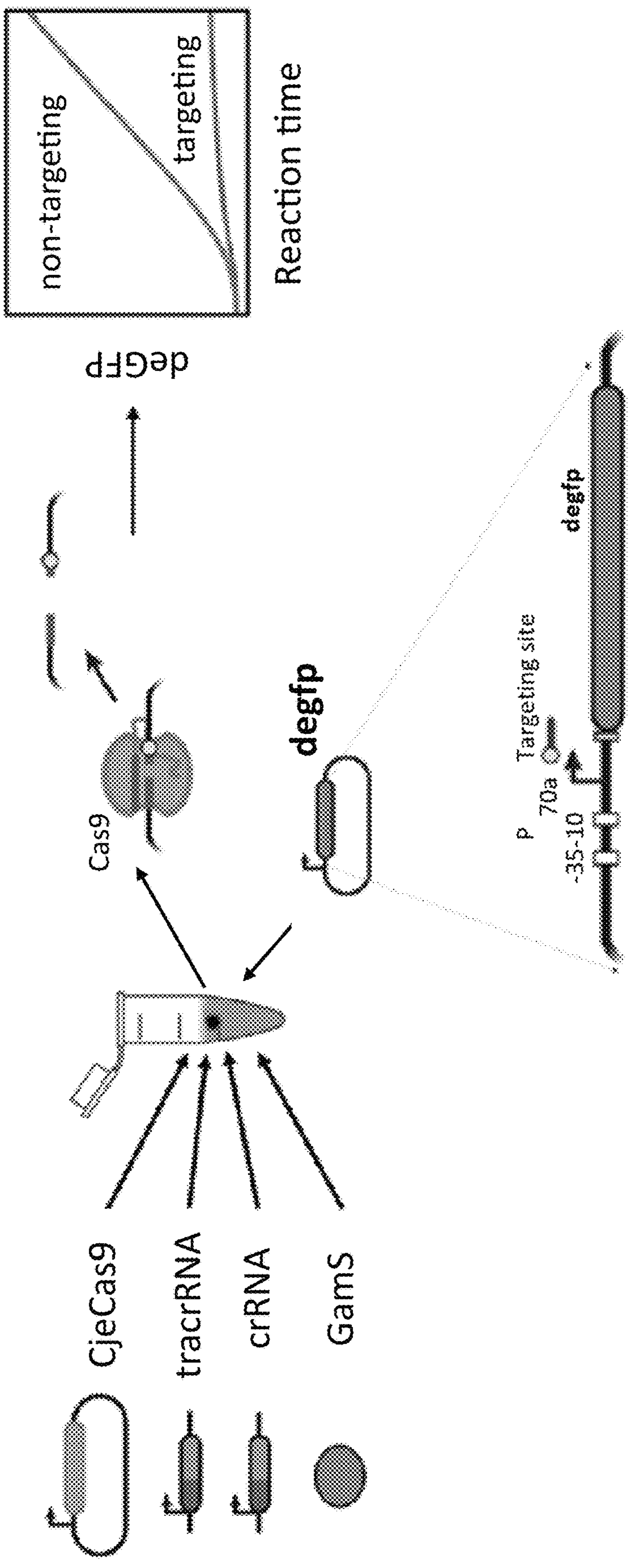

FIG. 2 shows a schematic overview of the conversion of a sensed RNA into an ncrRNA through the at least one non-naturally occurring tracrRNA and at least one tracrRNA-dependent CRISPR nuclease enzyme. Cas9 serves as a representative nuclease, although other CRISPR nucleases rely on a tracrRNA for crRNA biogenesis and function. FIG. 3 shows a schematic overview of the in vitro DNA cleavage assay comprising cell-free transcription-translation system (TXTL) as used in the context of the present invention, and as described in the examples, below. As part of the assay, plasmid or linear DNA encoding the nuclease (e.g. CjeCas9), a natural or non-natural tracrRNA, a crRNA or sensed RNA, and a GFP reporter optimized for TXTL expression (deGFP) targeted by the crRNA or ncrRNA are combined into the reaction. GamS is added to prevent the degradation of linear DNA by RecBCD. GFP fluorescence is then measured over time. Reduction or loss of fluorescence occurs when the crRNA:tracrRNA:CRISPR nuclease complex binds and cleaves the target within the reporter DNA, thereby halting GFP production.

FIG. 4 shows that the duplex between the repeat and anti-repeat can accommodate different sequences with little impact on targeting activity by CjeCas9. A) Different mutations made to the repeat:anti-repeat duplex of an sgRNA used by the CjeCas9. Mutations were made to change the sequence of the duplex while maintaining its secondary structure. The repeat and anti-repeat were fused in the form of an sgRNA to separate possible impacts of misfolding by the crRNA or tracrRNA on the resulting targeting activity. B) Results from the TXTL assay. The mutations resulted in limited impact on the time to target cleavage. NT: non-targeting sgRNA control. Related SEQ ID NOs: 18-21, sgRNAs were transcribed from J23119 promoter (SEQ ID NO: 13) and terminated with a rho-independent T500 terminator (SEQ ID NO: 14). NT: non-targeting sgRNA control (SEQ ID NO: 16), T: wild type targeting sgRNA (SEQ ID NO: 17), Target DNA (SEQ ID NO: 15).

Figure 5A:
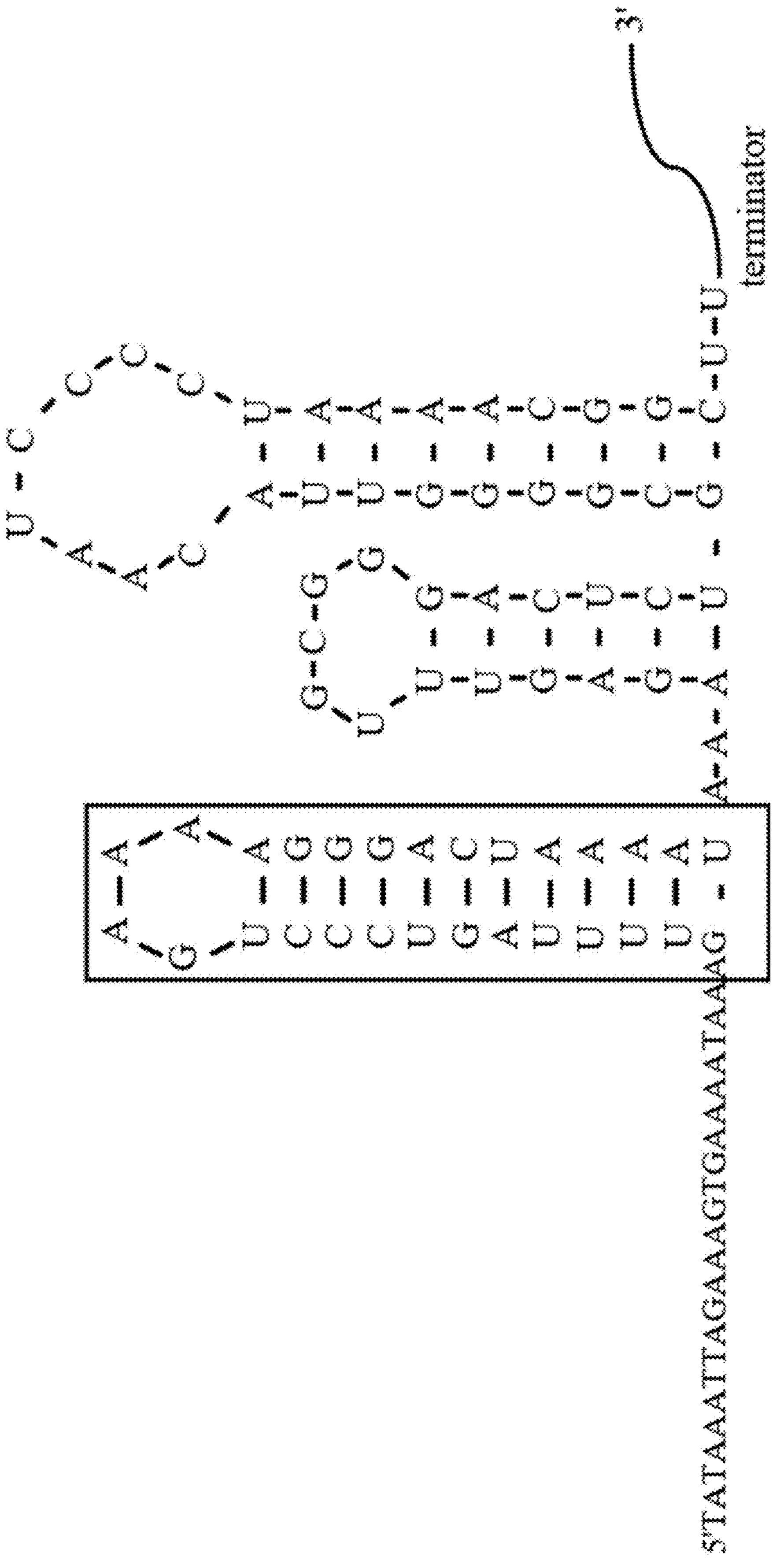
Figure 5B:
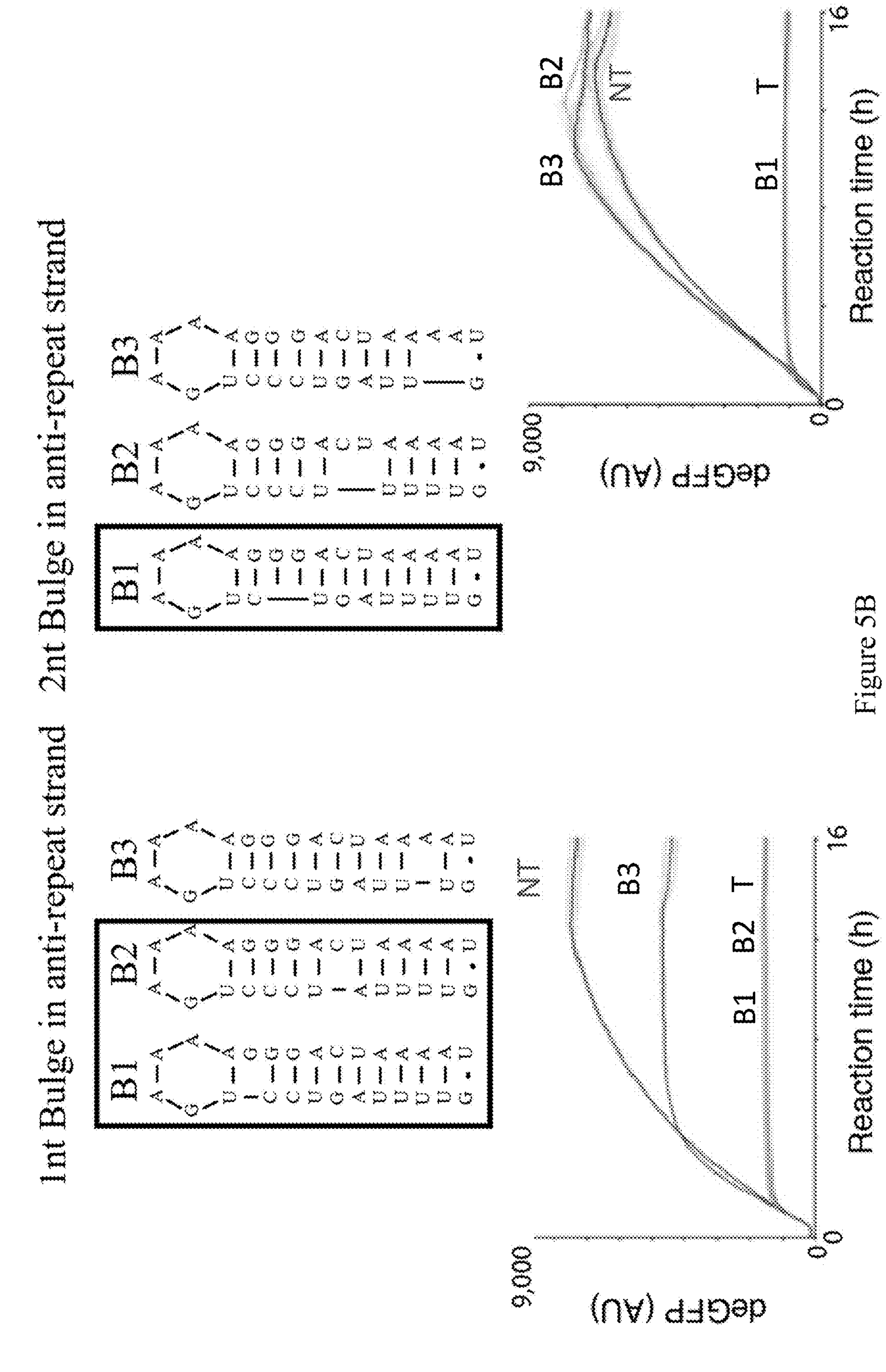
Figure 5C:
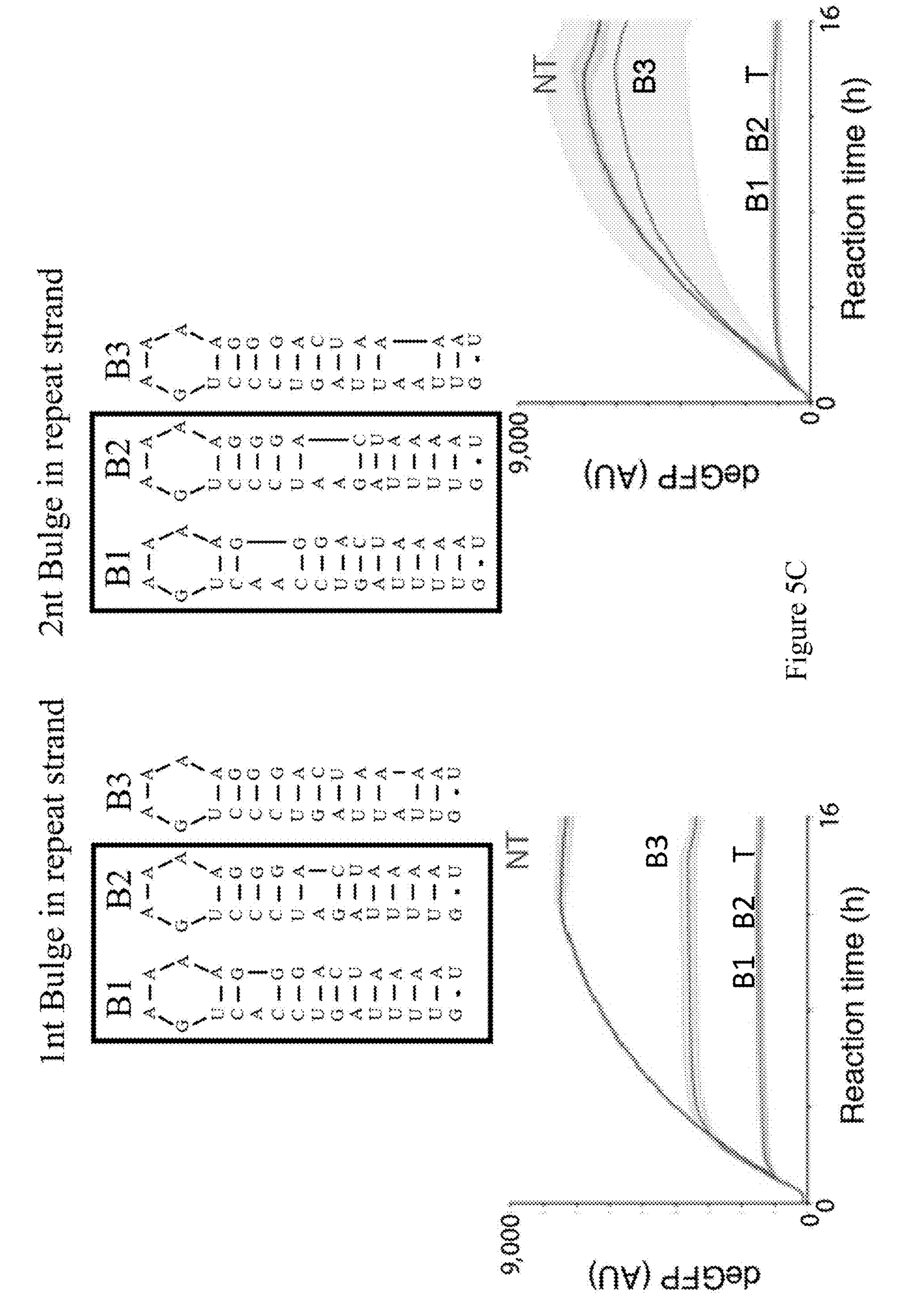

FIG. 5 shows that the duplex between the repeat and anti-repeat can accommodate some bulges on either side as part of DNA targeting by CjeCas9. A) Mutated region of the fused repeat:anti-repeat duplex boxed in boxed in black. The repeat and anti-repeat were fused in the form of an sgRNA to separate possible impacts of misfolding by the crRNA or tracrRNA on the resulting targeting activity. Transcription of the sgRNA is terminated with a rho-independent terminator depicted in yellow. B) Results from the TXTL assay following introduction of one-nt or two-nt bulges into the anti-repeat portion of the duplex. C) Results from the TXTL assay following introduction of one-nt or two-nt bulges into the repeat portion of the duplex. NT: non-targeting sgRNA control. Boxed duplexes maintained targeting activity despite the presence of the bulges. Related SEQ ID NOs: 23-33, sgRNAs were transcribed from J23119 promoter (SEQ ID NO: 13) and terminated with a rho-indpendent T500 terminator (SEQ ID NO: 14). NT: non-targeting sgRNA control (SEQ ID NO: 16), T: wild type targeting sgRNA (SEQ ID NO: 17), Target DNA (SEQ ID NO: 15).

FIG. 6 shows that the duplex between the repeat and anti-repeat can accommodate mismatches as part of DNA targeting by CjeCas9. A) Mutated region of the fused repeat:anti-repeat duplex is boxed in black. The repeat and anti-repeat were fused in the form of an sgRNA to separate possible impacts of misfolding by the crRNA or tracrRNA on the resulting targeting activity. Transcription of the sgRNA is terminated with a rho-independent terminator depicted in yellow. B) Results from the TXTL assay following introduction of one-nt or two-nt mismatches or G:U wobble pairs into the duplex. NT: non-targeting sgRNA control. Boxed duplexes maintained targeting activity despite the presence of the bulges. Related SEQ ID NO: 34-42, sgRNAs were transcribed from J23119 promoter (SEQ ID NO: 13) and terminated with a rho-indpendent T500 terminator (SEQ ID NO: 14). NT: non-targeting sgRNA control (SEQ ID NO: 16), T: wild type targeting sgRNA (SEQ ID NO: 17), Target DNA (SEQ ID NO: 15).

FIG. 7 shows that the region of the repeat:anti-repeat duplex involved in RNase III processing can accommodate mismatches and bulges as part of DNA targeting by CjeCas9. A) Mutated region within the repeat:anti-repeat duplex is boxed in gray. The modified crRNA and tracrRNA were expressed separately. B) TXTL results for mismatches. C) TXTL results for bulges. NT: non-targeting sgRNA control. Related SEQ ID NOS: 48-54. tracrRNA (SEQ ID NO: 45) was transcribed from OR2-OR1 promoter (SEQ ID NO: 43) and terminated with a rho-indpendent T500 terminator (SEQ ID NO: 14). CrRNA variants were transcribed from J23119 promoter (SEQ ID NO: 13) and terminated with a rho-indpendent T7 terminator (SEQ ID NO: 44). NT: non-targeting crRNA control (SEQ ID NO: 46), T: wild type targeting crRNA with 3' 300 overhang (SEQ ID NO: 47), Target DNA (SEQ ID NO: 15).

FIG. 8 shows that extensions to the 5' end or the 3' end of the crRNA have limited impact on targeting activity by CjeCas9. A) TXTL results for 5' extensions. B) TXTL results for 3' extensions. Related SEQ ID NOs: 56-60. tracrRNA (SEQ ID NO: 45) was transcribed from J23119 promoter (SEQ ID NO: 13) and terminated with a rho-indpendent T7 terminator (SEQ ID NO: 44). CrRNA variants were transcribed from J23119 promoter (SEQ ID NO: 13) and terminated with a rho-indpendent T7 terminator (SEQ ID NO: 44). NT: non-targeting crRNA control (SEQ ID NO: 46), WT: fliF-targeting crRNA (SEQ ID NO: 55), Target DNA (SEQ ID NO: 15).

FIG. 9 shows that non-natural tracrRNAs can be designed to direct formation of active ncrRNAs used by CjeCas9 from a sensed RNA. A) General design approach for non-natural tracrRNAs and accompanying DNA targets for CjeCas9. Left: sequence and secondary structure of a crRNA hybridized to the natural tracrRNA. The guide sequence of the crRNA is indicated by N's. Right: sequence and secondary structure of a non-natural tracrRNA paired with a sensed RNA. The anti-repeat portion of the non-natural tracrRNA hybridizes with one portion of the sensed RNA, while the upstream portion of the sensed RNA becomes the guide sequence in the resulting ncrRNA. The DNA target is designed to encode the guide sequence of the ncrRNA flanked by a PAM recognized by this nuclease. B) TXTL results demonstrating DNA targeting directed by a sensed RNA and a non-natural tracrRNA. Each non-natural tracrRNA is designed to hybridize to a specific region of the tested RNA. The tested RNA is the mRNA associated with peak 113 from a CjeCas9 co-immunoprecipitation experiment performed by the inventors using *C. jejuni* strain 84-21. This mRNA is derived from genes CJ8421_04970 & 04975 & 04980. T: presence of the target sequence in the GFP reporter construct. NT: absence of the target sequence in the GFP reporter construct. Overall, the tested non-natural tracrRNAs generally resulted in strong cleavage activity. Related SEQ ID NOS: 62~71. Peak113-harbored mRNA (SEQ ID NO: 61) was transcribed from J23119 promoter (SEQ ID NO: 13) and terminated with a rho-indpendent T7 terminator (SEQ ID NO: 44). Reprogrammed tracrRNAs were transcribed from OR2-OR1 promoter (SEQ ID NO: 43) and terminated with a rho-indpendent T500 terminator (SEQ ID NO: 14).

FIG. 10 shows that non-natural tracrRNAs can be designed to direct formation of active ncrRNAs used by SpyCas9 from a sensed RNA. A) General design approach for non-natural tracrRNAs and accompanying DNA targets for SpyCas9. Left: sequence and secondary structure of a crRNA hybridized to the natural tracrRNA. The guide sequence of the crRNA is indicated by N's. Right: sequence and secondary structure of a non-natural tracrRNA paired with a sensed RNA. The anti-repeat portion of the non-natural tracrRNA hybridizes with one portion of the sensed RNA, while the upstream portion becomes the guide sequence in the resulting ncrRNA. The DNA target is designed to encode the guide sequence of the ncrRNA flanked by a PAM recognized by this nuclease. B) TXTL results demonstrating DNA targeting directed by a sensed RNA and a non-natural tracrRNA. Each non-natural tracrRNA is designed to hybridize to a specific region of the tested RNA. The tested RNA is the mRNA associated with peak 113 from the co-immunoprecipitation experiment. This mRNA is derived from genes CJ8421_04970 & 04975 & 04980. T: presence of the target sequence in the GFP reporter construct. NT: absence of the target sequence in the GFP reporter construct. Overall, all five tested non-natural tracrRNAs resulted in strong cleavage activity. Related SEQ ID NOs: 72~81. Peak113-harbored mRNA (SEQ ID NO: 61) was transcribed from J23119 promoter (SEQ ID NO: 13) and terminated with a rho-indpendent T7 terminator (SEQ ID NO: 44). Reprogrammed tracrRNAs were transcribed from OR2-OR1 promoter (SEQ ID NO: 43) and terminated with a rho-indpendent T500 terminator (SEQ ID NO: 14).

FIG. 11 shows that non-natural tracrRNAs can be designed to direct formation of active ncrRNAs used by SthlCas9 from a sensed RNA. A) General design approach for non-natural tracrRNAs and accompanying DNA targets for SthlCas9. Left: sequence and secondary structure of a crRNA hybridized to the natural tracrRNA. The guide sequence of the crRNA is indicated by N's. Right: sequence and secondary structure of a non-natural tracrRNA paired with a sensed RNA. The anti-repeat portion of the non-natural tracrRNA hybridizes with one portion of the sensed RNA, while the upstream portion becomes the guide sequence in the resulting ncrRNA. The DNA target is designed to encode the guide sequence of the ncrRNA flanked by a PAM recognized by this nuclease. B) TXTL results demonstrating DNA targeting directed by a sensed RNA and a non-natural tracrRNA. Each non-natural tracrRNA is designed to hybridize to a specific region of the tested RNA. The tested RNA is the mRNA associated with peak 113 from the co-immunoprecipitation experiment. This mRNA is derived from genes CJ8421_04970 & 04975 & 04980. T: presence of the target sequence in the GFP reporter construct. NT: absence of the target sequence in the GFP reporter construct. Overall, all five tested non-natural tracrRNAs resulted in strong cleavage activity. Related SEQ ID NOS: 82-91. Peak113-harbored mRNA (SEQ ID NO: 61) was transcribed from J23119 promoter (SEQ ID NO: 13) and terminated with a rho-independent T7 terminator (SEQ ID NO: 44). Reprogrammed tracrRNAs were transcribed from OR2-OR1 promoter (SEQ ID NO: 43) and terminated with a rho-independent T500 terminator (SEQ ID NO: 14).

Figure 12:
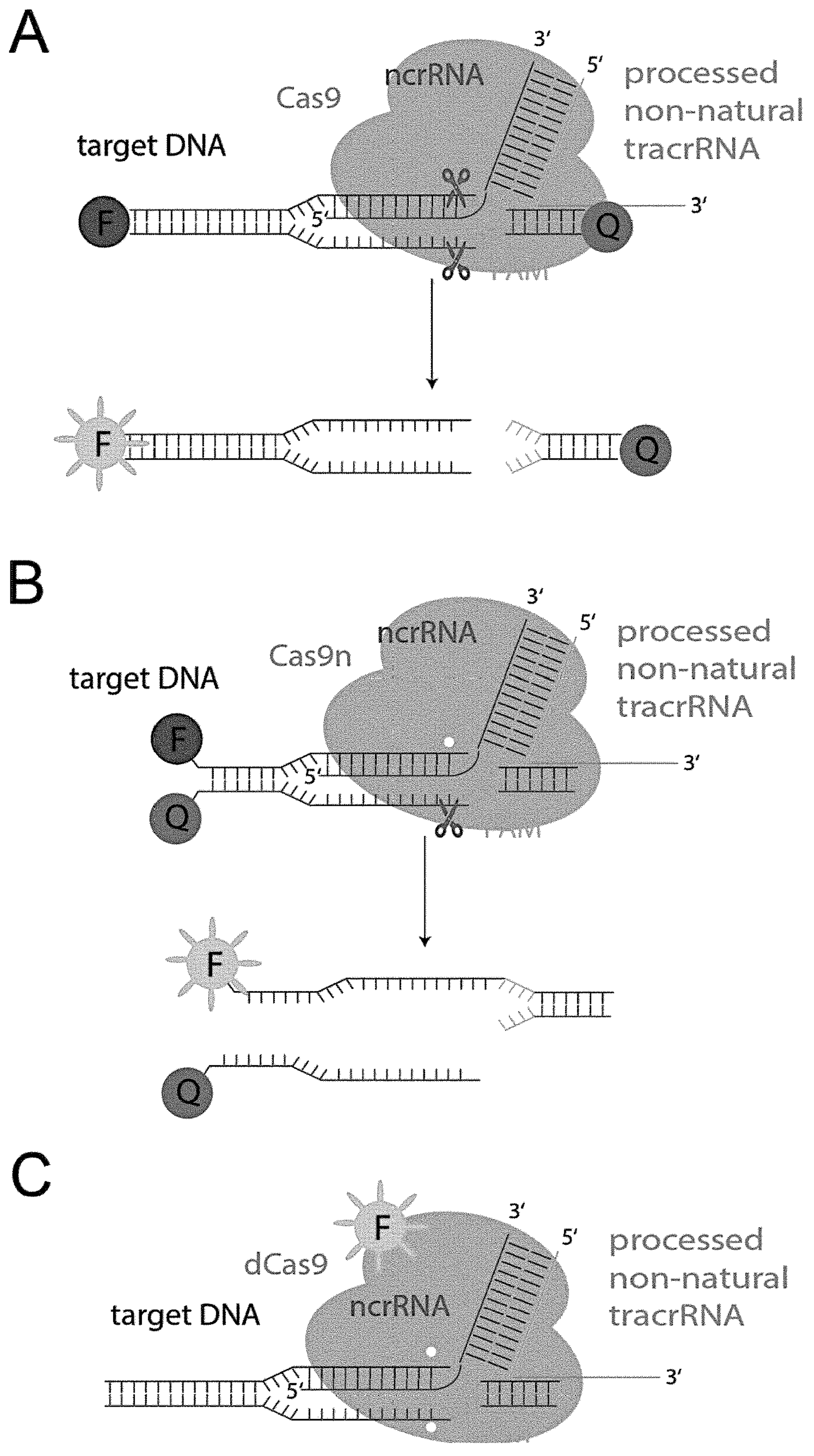

FIG. 12 shows examples of the in vitro diagnostic "reporter" function to report the presence of a sensed RNA in a sample. In the two provided examples, the sensed RNA is converted into an ncrRNA through the non-natural tracrRNA and complexes with the tracrRNA-dependent CRISPR nuclease. Recognition of the DNA target specified by ncrRNA yields a detectable signal. A) DNA recognition and subsequent cleavage yields a fluorescent signal. The target nucleic acid is covalently linked to a fluorophore (F) on one end and a quencher (Q) on the other end. The two molecules are sufficiently close for the quencher to mask the fluorophore. However, target cleavage allows the two DNA pieces to be separated, resulting in a fluorescent signal. B) DNA recognition and subsequent nicking yields a fluorescent signal. The target nucleic acid is covalently linked to a fluorophore and quencher on the same end of the target and non-target strands, respectively. Targeting by a tracrRNA-dependent CRISPR nuclease mutated to nick (e.g. Cas9n) only the non-target strand results in release of the non-target strand linked to the quencher. Once the strand diffuses away, a fluorescent signal is produced. C) DNA binding localizes a fluorescent signal. A catalytically-dead tracrRNA-dependent CRISPR nuclease (e.g. dCas9) is functionally linked to a fluorescent signal.

Figure 13:
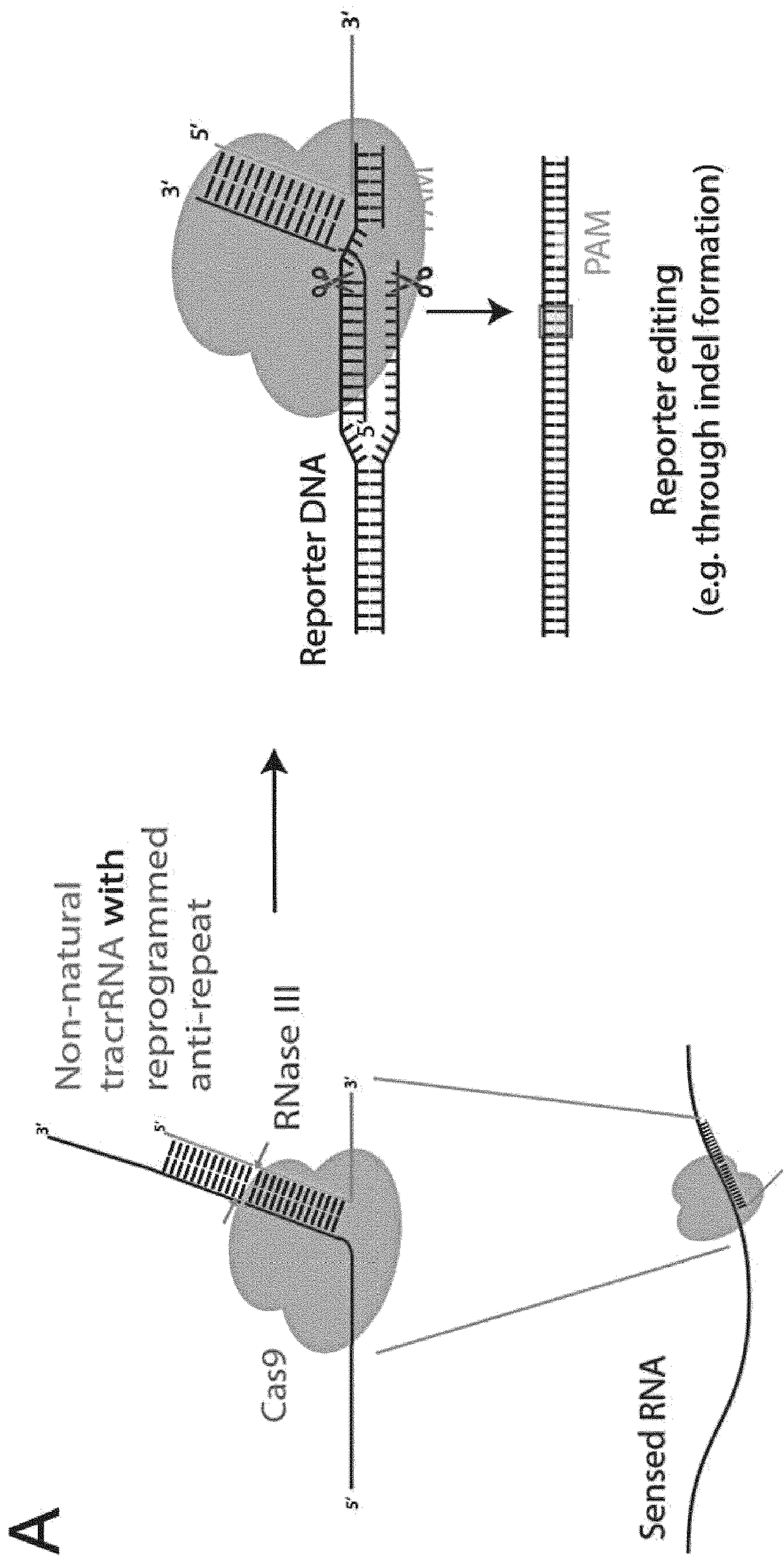

FIG. 13 shows examples of in vivo transcriptional recording in which a sensed RNA is converted into a readable signal. In each example, the sensed RNA is converted into an ncrRNA through the non-natural tracrRNA, and the ncrRNA directs the tracrRNA-dependent CRISPR nuclease to the target "reporter" DNA. A) The "reporter" DNA undergoes editing, resulting in a detectable edit that is stored in the DNA. An indel is shown, although many other types of edits are possible (e.g. through HDR, base editing, prime editing or RNA editing). B) The expression of a reporter gene is modulated. A fusion between dCas9 and the transcriptional activation domain VP16 is shown, although many other modes of expression modulation are possible (e.g. fusing other regulatory domains to the nuclease, using a catalytically-dead nuclease or a catalytically-active nuclease paired with a partially mutated guide sequence, using scaffold sgRNAs that recruit the regulatory domains).

FIG. 14 shows how non-natural tracrRNAs can be employed to drive transcription-dependent targeting. The non-natural tracrRNA is designed to hybridize to a region within the sensed RNA encoding a PAM. The ensuing ncrRNA drives targeting of the genetic locus encoding the sensed RNA. As a result, targeting only occurs when the locus is transcribed. If targeting results in a smaller indel (e.g. a 1-nt deletion), the transcribed sensed RNA will encode the mutation and still drive targeting. The practical effect is larger indels or more opportunities for alternative repair pathways (e.g. HDR).

Figure 15A:
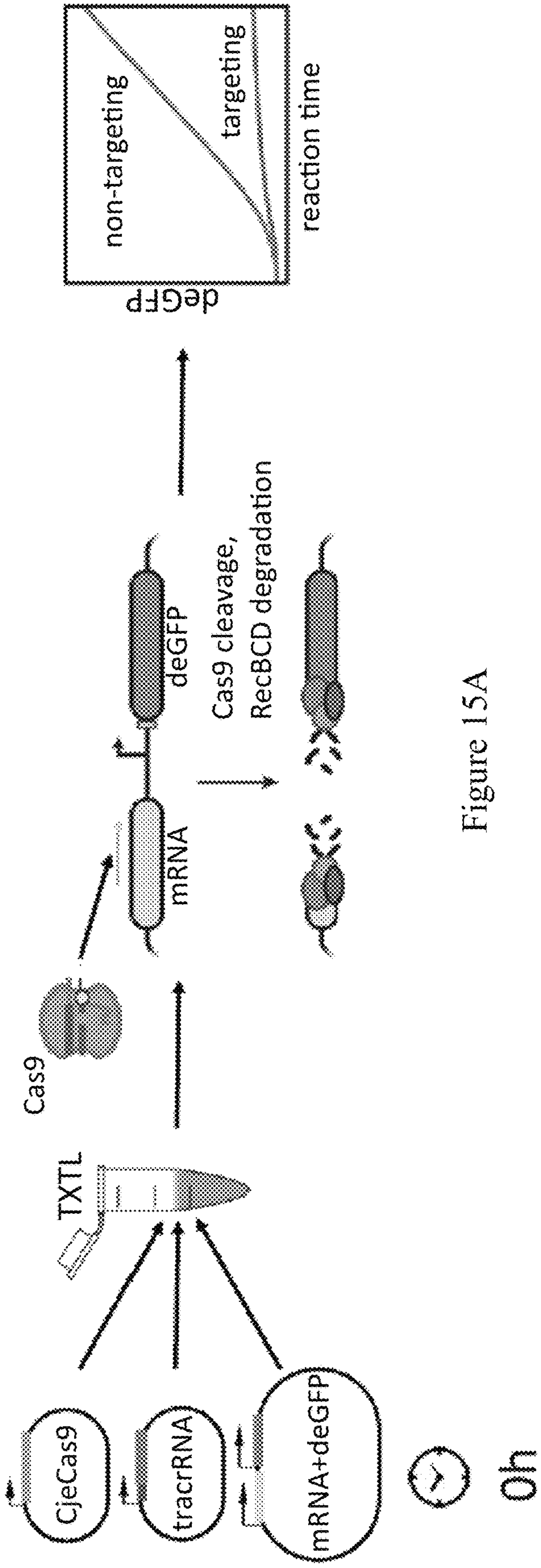
Figure 15B:
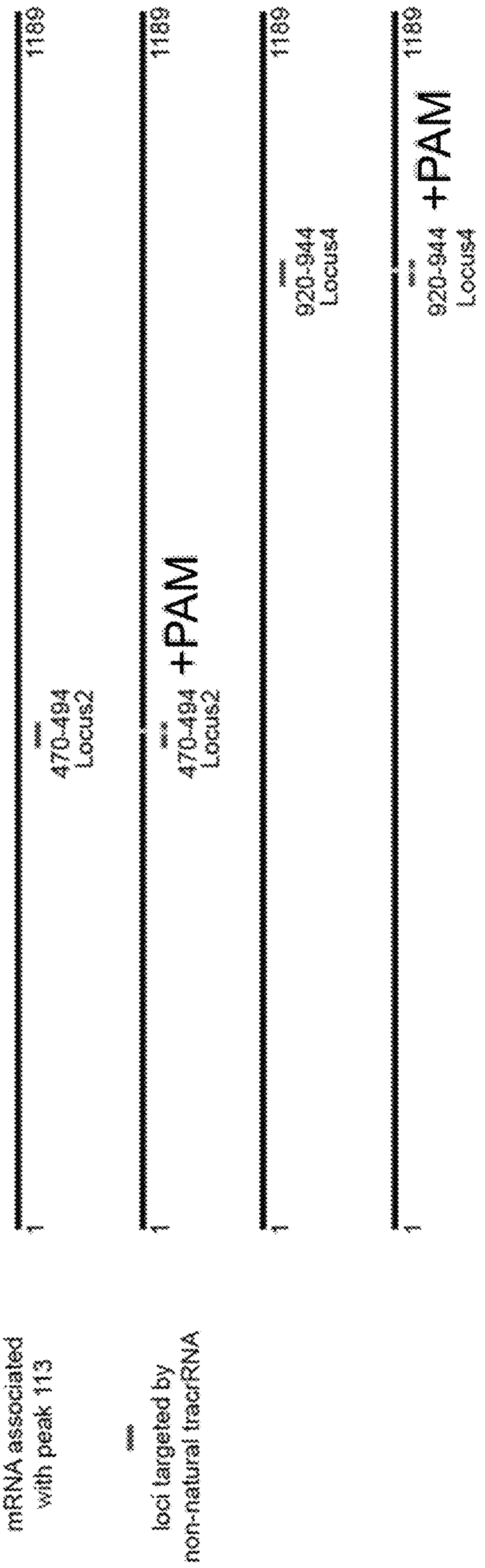
Figure 15C:
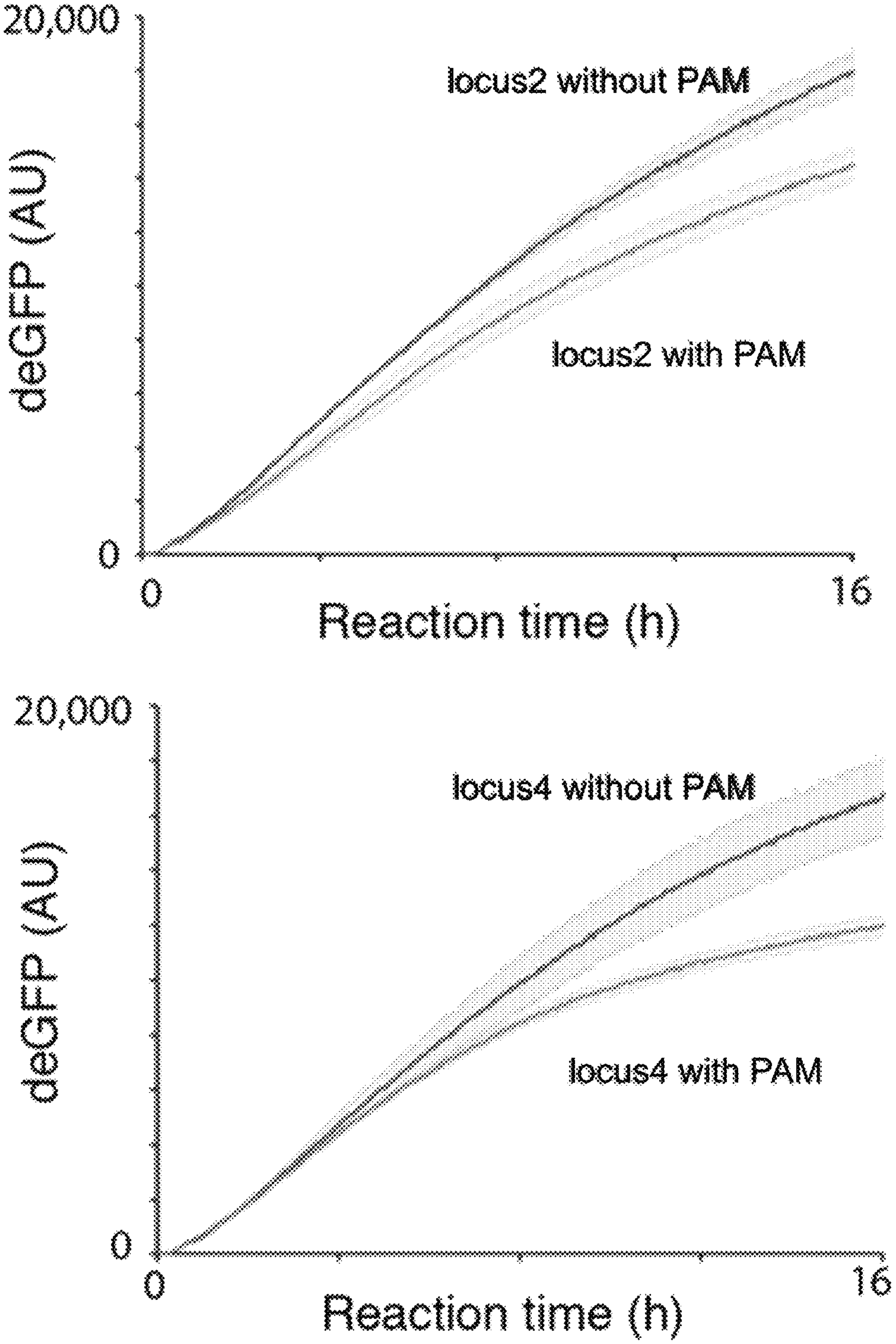

FIG. 15 shows that transcription-dependent targeting can be achieved with non-natural tracrRNAs hybridizing to sensed RNAs harboring a PAM. A) TXTL setup to detect transcription-dependent targeting. As part of the setup, the sensed RNA is expressed from a plasmid also encoding the GFP reporter (SEQ ID NO: 96) under a different promoter. Cleavage of the plasmid DNA leads to loss of GFP expression through rapid degradation by RecBCD present in the TXTL mix. A sensed RNA and complementary non-natural tracrRNA lacking the PAM serve as negative controls. B) Locations within the peak 113 mRNA to which the non-natural tracrRNAs utilized by CjeCas9 are designed to hybridize. The mRNA and the non-natural tracrRNA were both mutated to encode a PAM recognized by the CjeCas9. C) TXTL results showing reduced fluorescence levels in the presence of the PAM, in line with the sensed RNA driving cleavage of its own DNA sequence by CjeCas9. Peak113-harbored mRNA and its variants with PAM (SEQ ID NOs: 61, 93, 95) were transcribed from J23119 promoter (SEQ ID NO: 13) and terminated with a rho-independent T7 terminator (SEQ ID NO: 44). Reprogrammed tracrRNAs and their variants with PAM (SEQ ID NOs: 64, 92, 68, 94) were transcribed from OR2-OR1 promoter (SEQ ID NO: 43) and terminated with a rho-independent T500 terminator (SEQ ID NO: 14).

Figure 16:
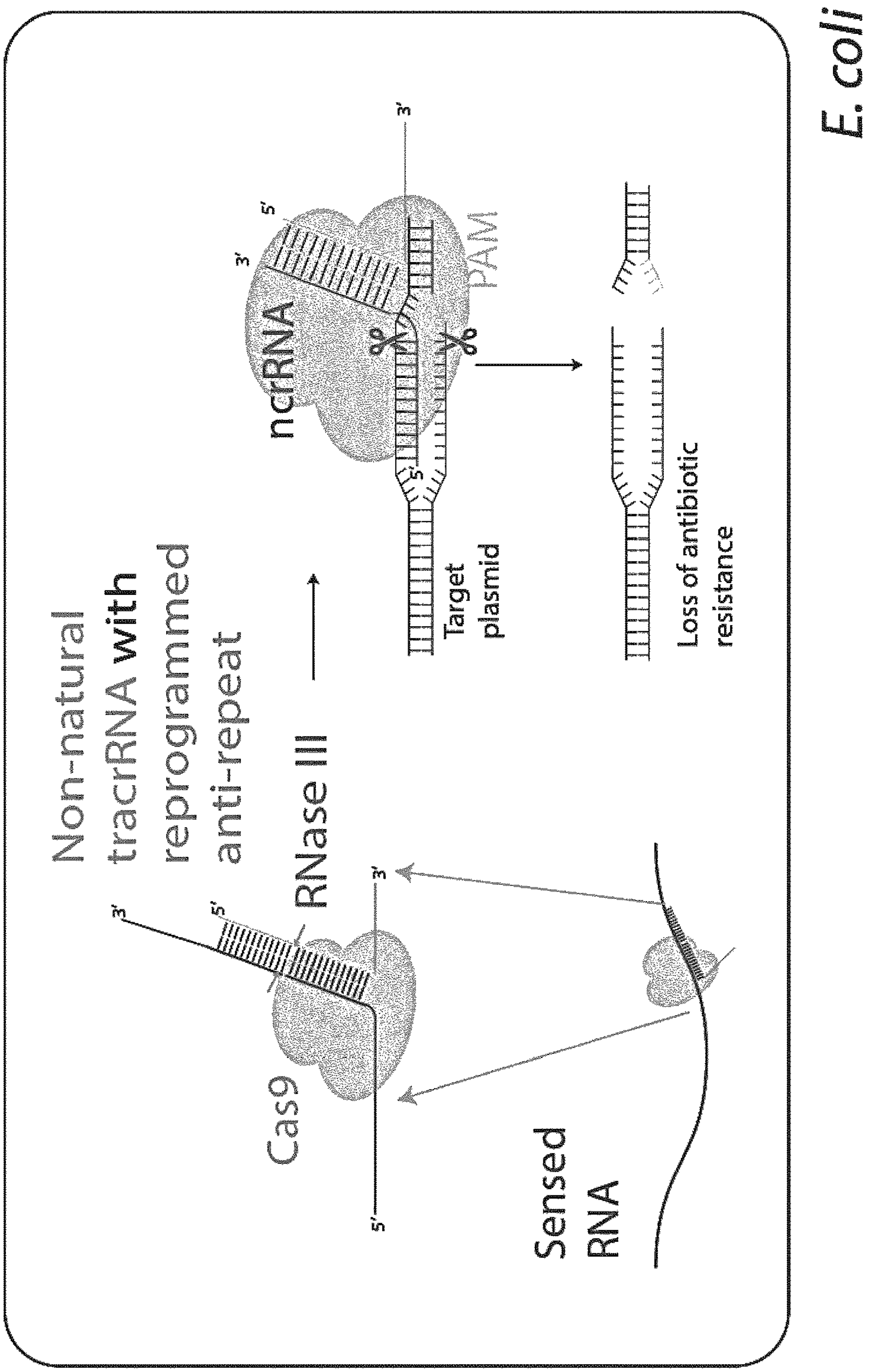
Figure 16:
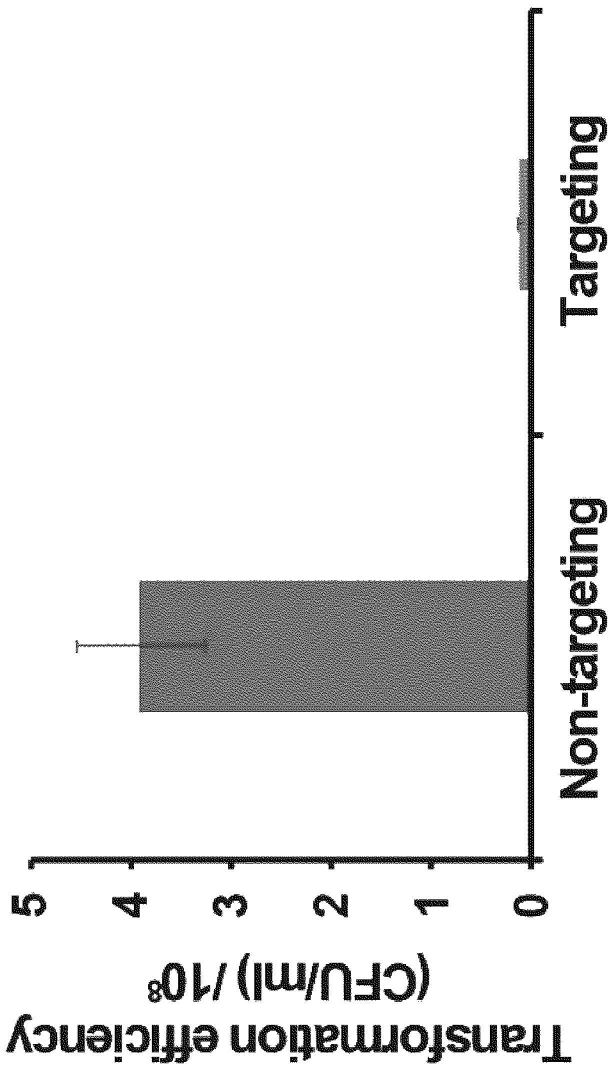

FIG. 16 shows that RNA detection can be achieved in vivo with non-natural tracrRNAs. A) Experimental setup in *E. coli* to link the presence of a sensed RNA to cleavage of a plasmid encoding the corresponding target sequence. The assay was conducted with the CjeCas9 and a non-natural tracrRNA designed to convert a portion of the sensed RNA (derived from peak 113) into an active ncrRNA. B) Plasmid clearance results. *E. coli* cells harboring plasmids expressing the sensed RNA, the reprogrammed tracrRNA, and CjeCas9 were transformed with a plasmid with (targeting) or without (non-targeting) the target and then plated to select for colonies harboring all plasmids. The presence of the sensed RNA and the target sequence resulted in a large reduction in the number of transformed colonies compared to a non-targeting control. Sensed mRNA (SEQ ID NO: 61) was transcribed from J23119 promoter (SEQ ID NO: 13) and terminated with a rho-independent T7 terminator (SEQ ID NO: 44). Reprogrammed tracrRNA (SEQ ID NO: 66) were transcribed from OR2-OR1 promoter (SEQ ID NO: 43) and terminated with a rho-independent T500 terminator (SEQ ID NO: 14). Target DNA (SEQ ID NO: 67).

Figure 17:
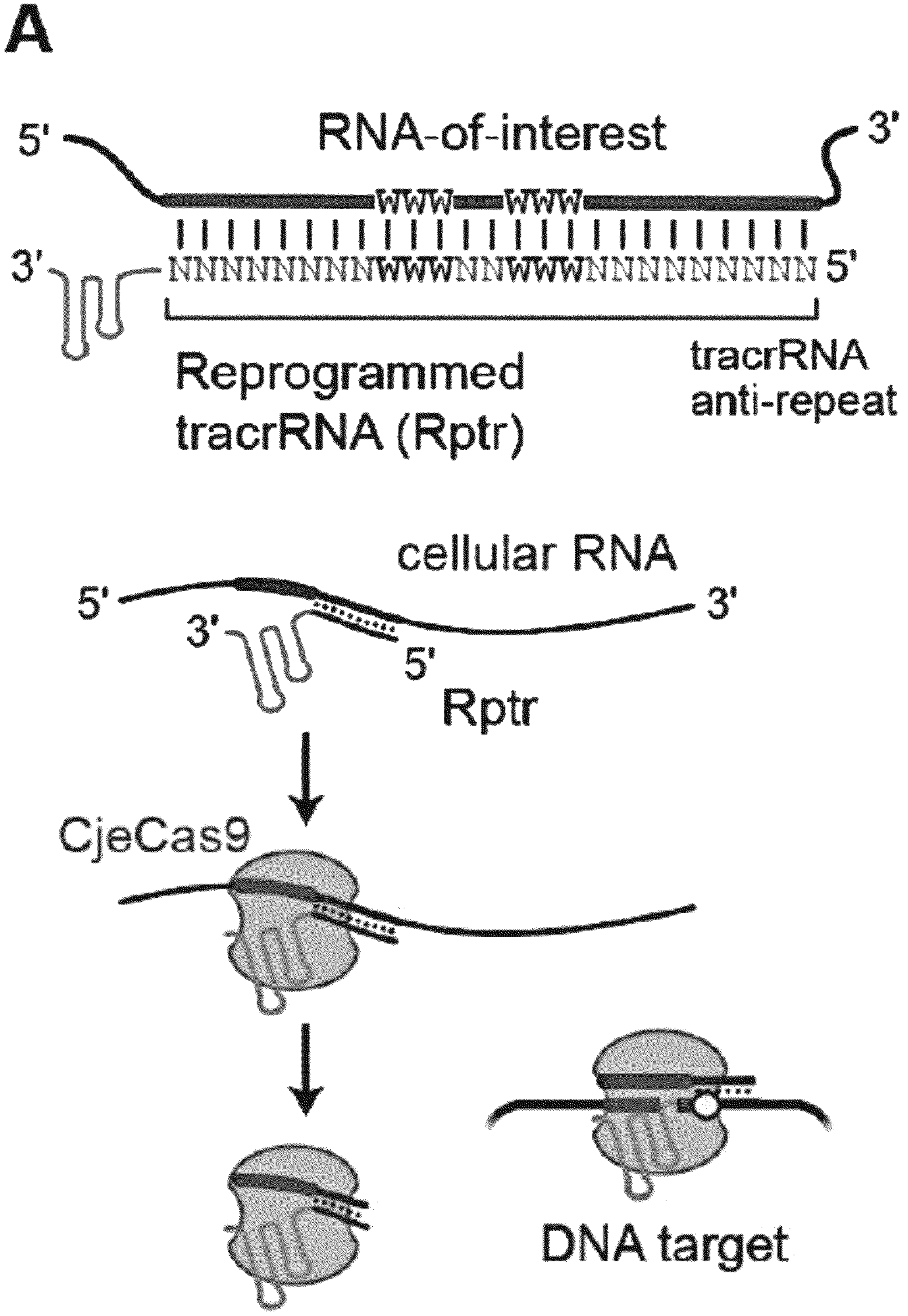
Figure 17:
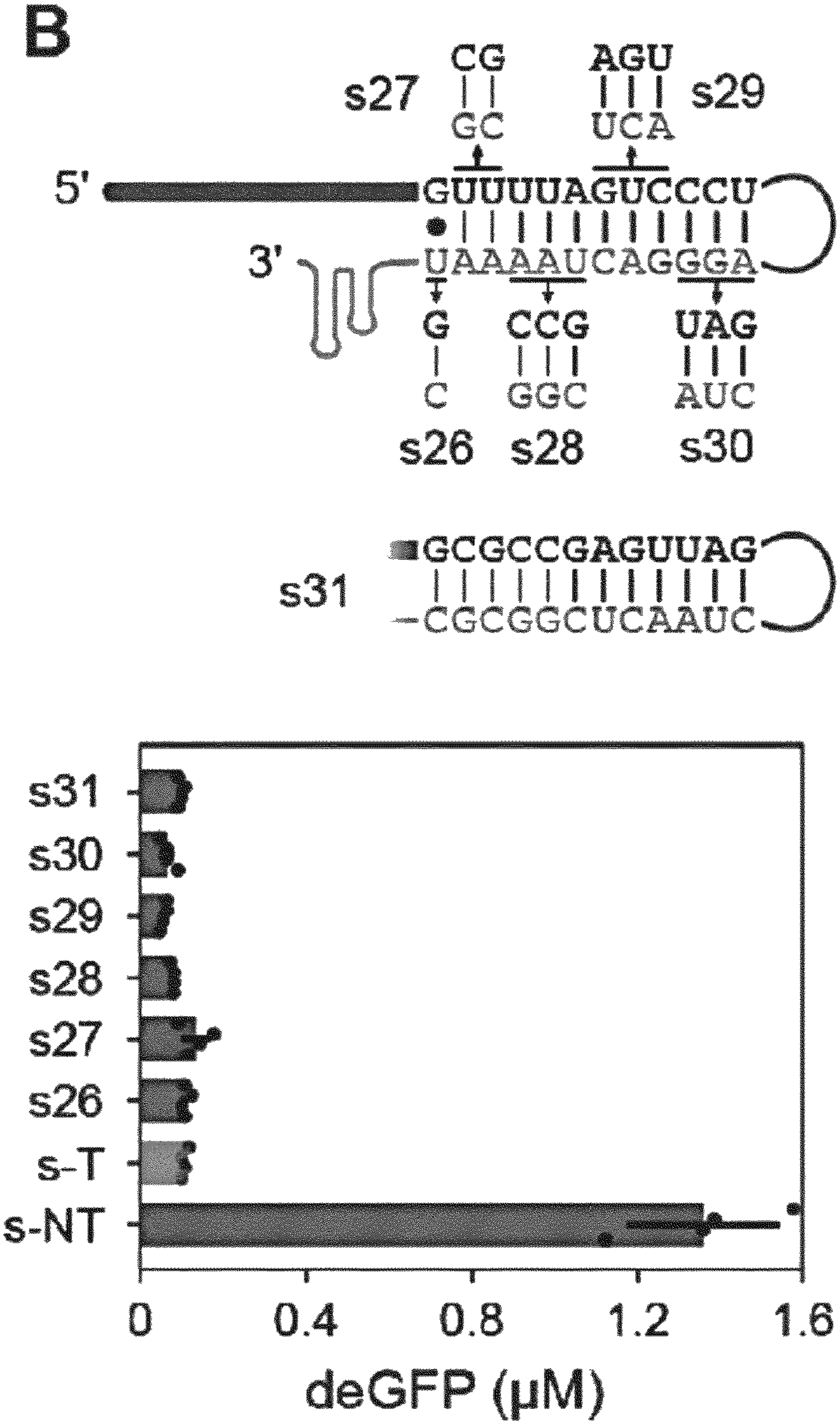
Figure 17:
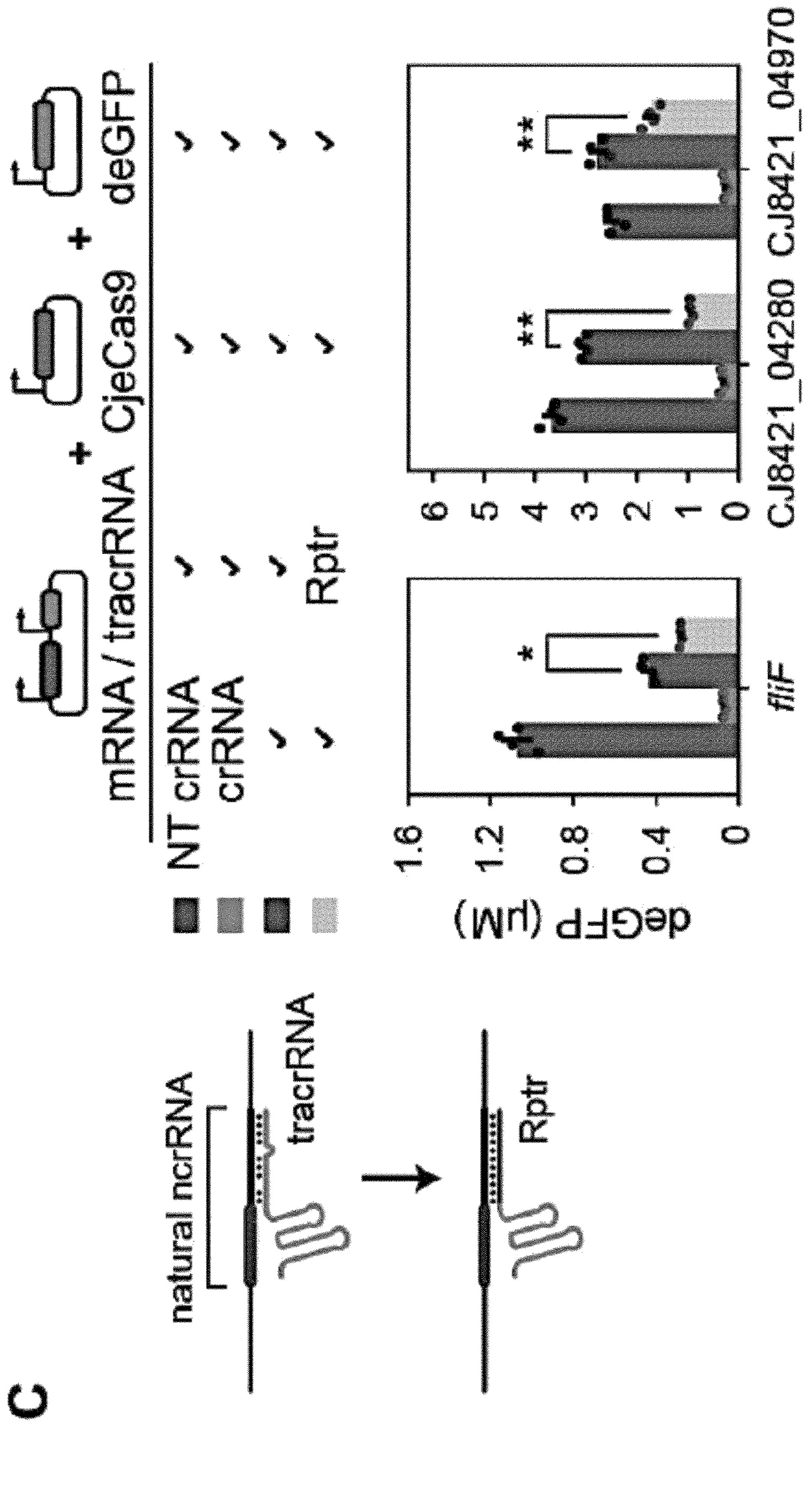
Figure 17:
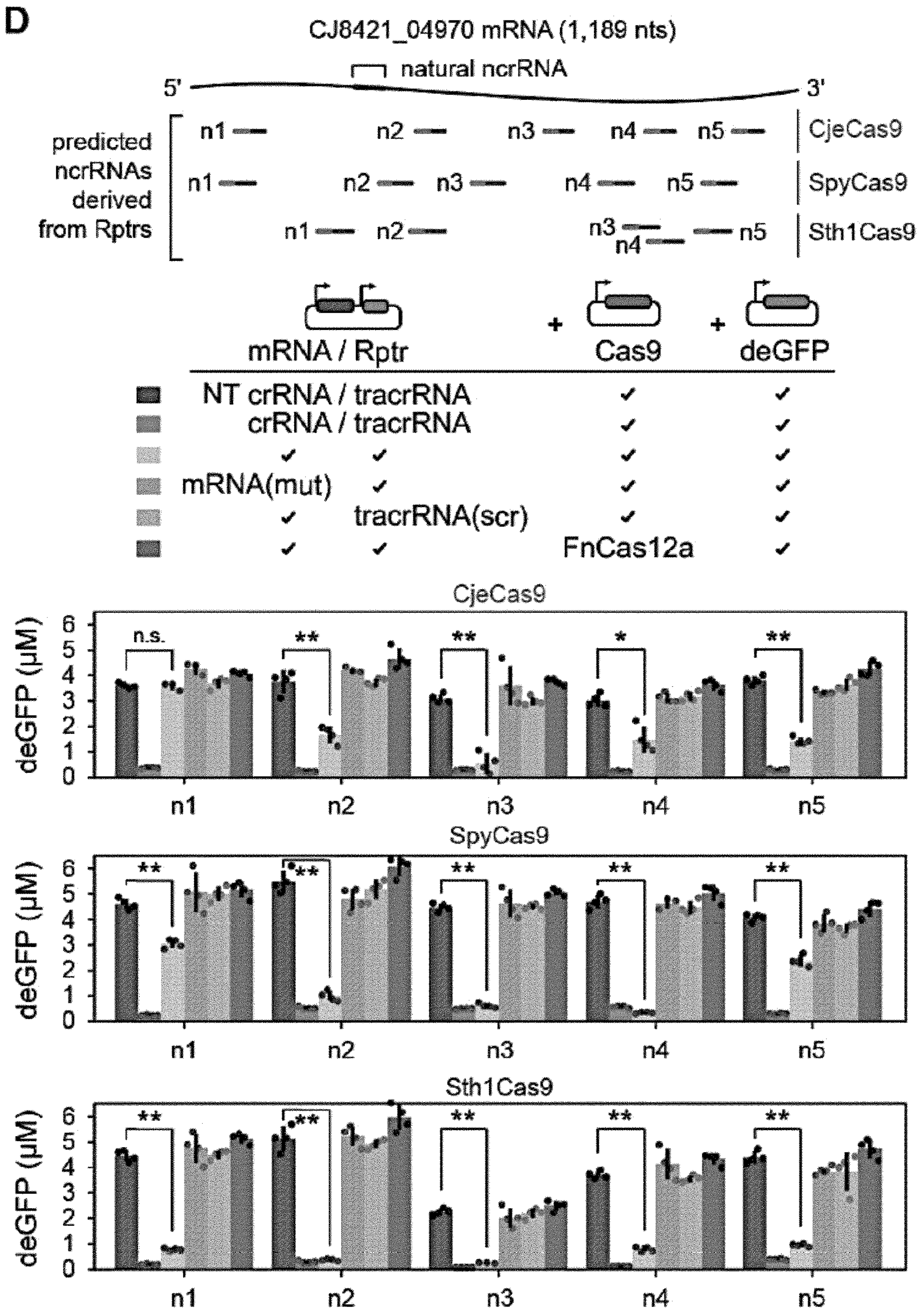

FIG. 17 shows that reprogrammed tracrRNAs co-opt RNA transcripts to guide different Cas9 orthologs. A) Design of reprogrammed tracrRNAs (non-natural tracrRNAs) utilized by CjeCas9. The RpT-RNA converts an RNA of-interest into an ncrRNA that directs Cas9 to its PAM-flanked DNA target. W=A or T. PAM: yellow circle. B) Toleration of mutations to the RNA duplex of an sgRNA that preserve secondary structure in TXTL. The duplex reflects the first 12 nts of cellular RNA pairing with the tracrRNA. C) Enhancing DNA targeting by less-functional or non-functional ncrRNAs by converting the tracrRNA into a non-natural tracrRNA in TXTL. D) Sequence-specific DNA targeting in TXTL using non-natural tracrRNAs compatible with three different Cas9 nucleases. Values in B-D represent the mean and standard deviation from four replicates in TXTL. *: $p<0.01$. **: $p<0.001$, n.s.: not significant. Sequences as shown are GUUUUAGUCCCU (SEQ ID NO: 98), AGGGACUAAAAU (SEQ ID NO: 99), GCGCCGAGUUAG (SEQ ID NO: 100), and CUAACUCGGCGC (SEQ ID NO: 101).

FIG. 18 shows that reprogrammed tracrRNAs enable multiplexable RNA detection with single-base resolution in vitro. A) Overview of the multiplexed diagnostic platform LEOPARD. B) Highly specific ncrRNA-mediated cleavage of target DNA by Cas9 in vitro. C) Multiplexed monitoring of DNA targets. A Cy5 fluorescent dye is appended to one end of each DNA target, and the lengths of the sequences flanking each target are varied to ensure that all products can be visualized based on size when resolved on a gel. D) Parallel detection of nine different RNA fragments associated with respiratory viruses by denaturing PAGE. Filled dots in D and E indicate the presence of the component listed on the right. (E) Specific detection of the D614G point mutation within the spike protein of SARS-CoV-2. Each detected T7-transcribed RNA in B, D and E comprised the intended ncrRNA sequence with 50-nt extensions on either end.

Figure 19:
Figure 19:
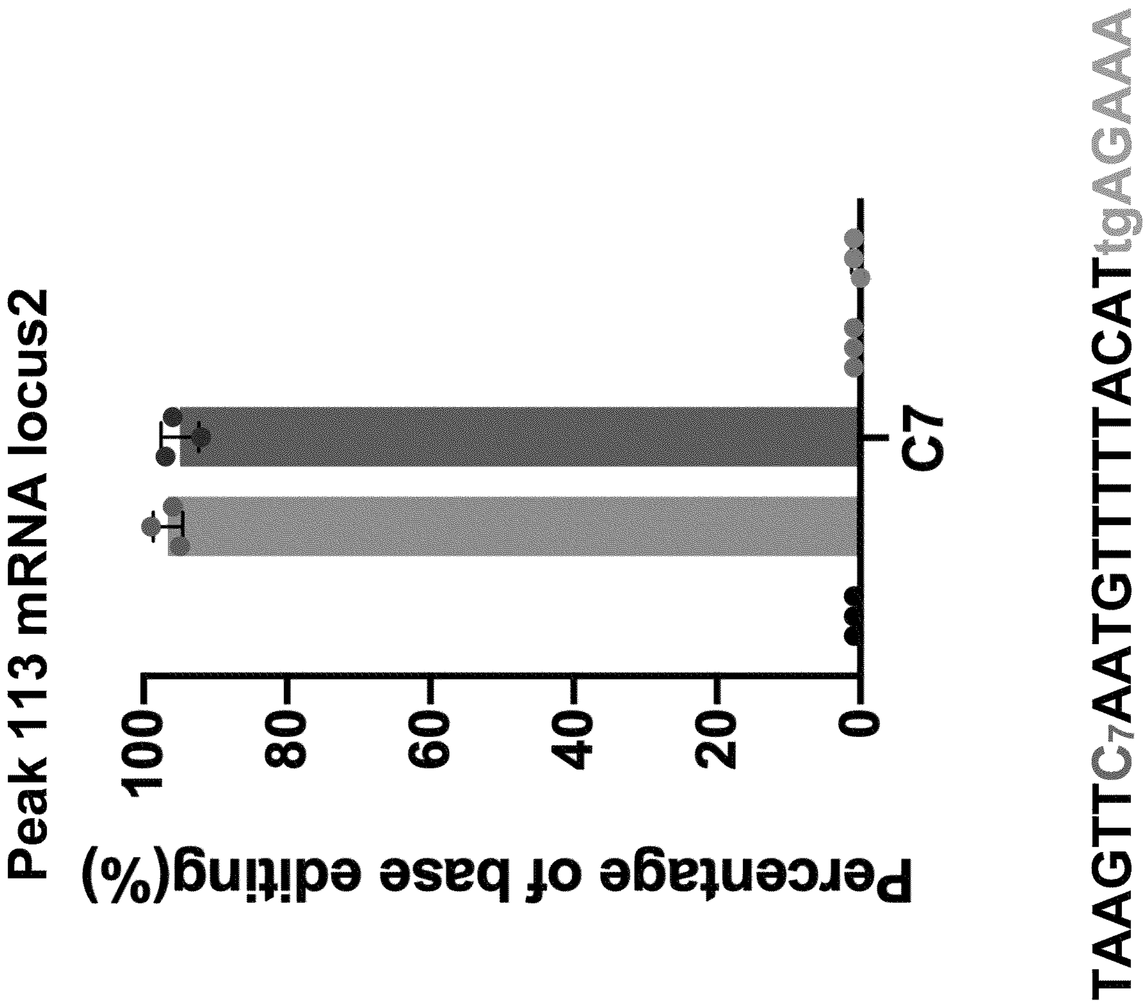

FIG. 19 shows the method for transcriptional recording according to the present invention. In this embodiment, the SthlnCas9 base editor can record transcriptional events. Expressing the non-natural tracrRNA with the sensed RNA leads to base editing of the target DNA on a plasmid in *E. coli*. Editing was as efficient as that by the designed crRNA: tracrRNA. A) Tested constructs. Check marks indicate use of the construct above the line. NT: non-target; mRNA(mut): mRNA encoding the ncrRNA with point mutations in the putative "seed" region of the guide; tracrRNA(scr): tracrRNA with anti-repeat sequence scrambled. Blue rectangle in target plasmid, target sequence; yellow circle, Cas9 PAM. B) Editing efficiency in *E. coli* based on the tested constructs. The sequence as shown is taagttcaatgtttttacattgagaaa (SEQ ID NO: 102).

Figure 20:
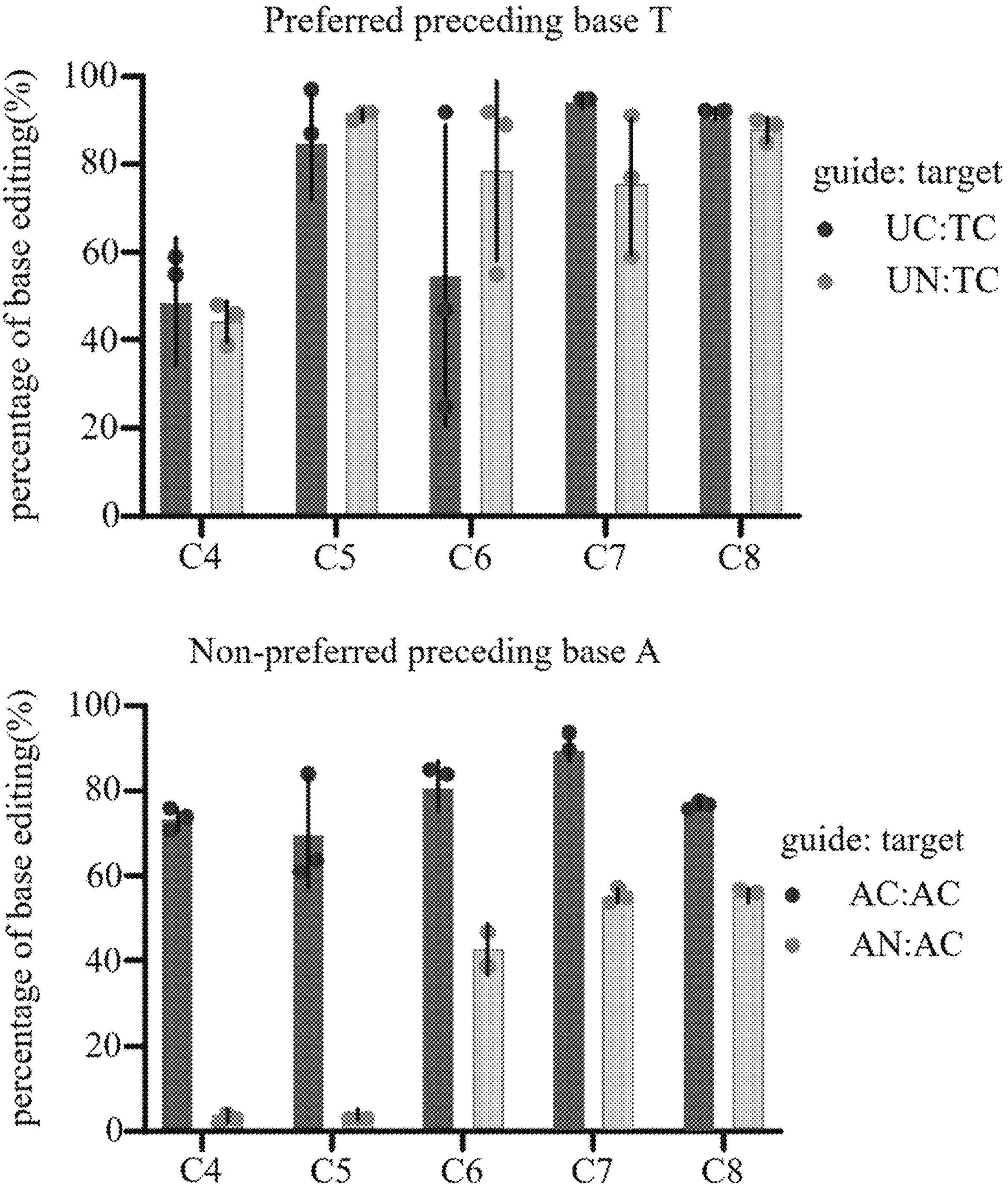

FIG. 20 shows the method for transcriptional recording according to the present invention, where RNAs lacking a C in the editing region were recorded. For these, the target did not originally include a C, but we inserted one at different locations to assess editing. In this case, editing was observed when the C was inserted at different locations, even though it created a mismatch between the guide and the target. Editing was assessed similar to FIG. 19. The sequences as shown are agaauuuaugugaauuuuauug (SEQ ID NO: 103), and agaatttatgtgaattttattgtgagaaa (SEQ ID NO: 104).

Figure 21:
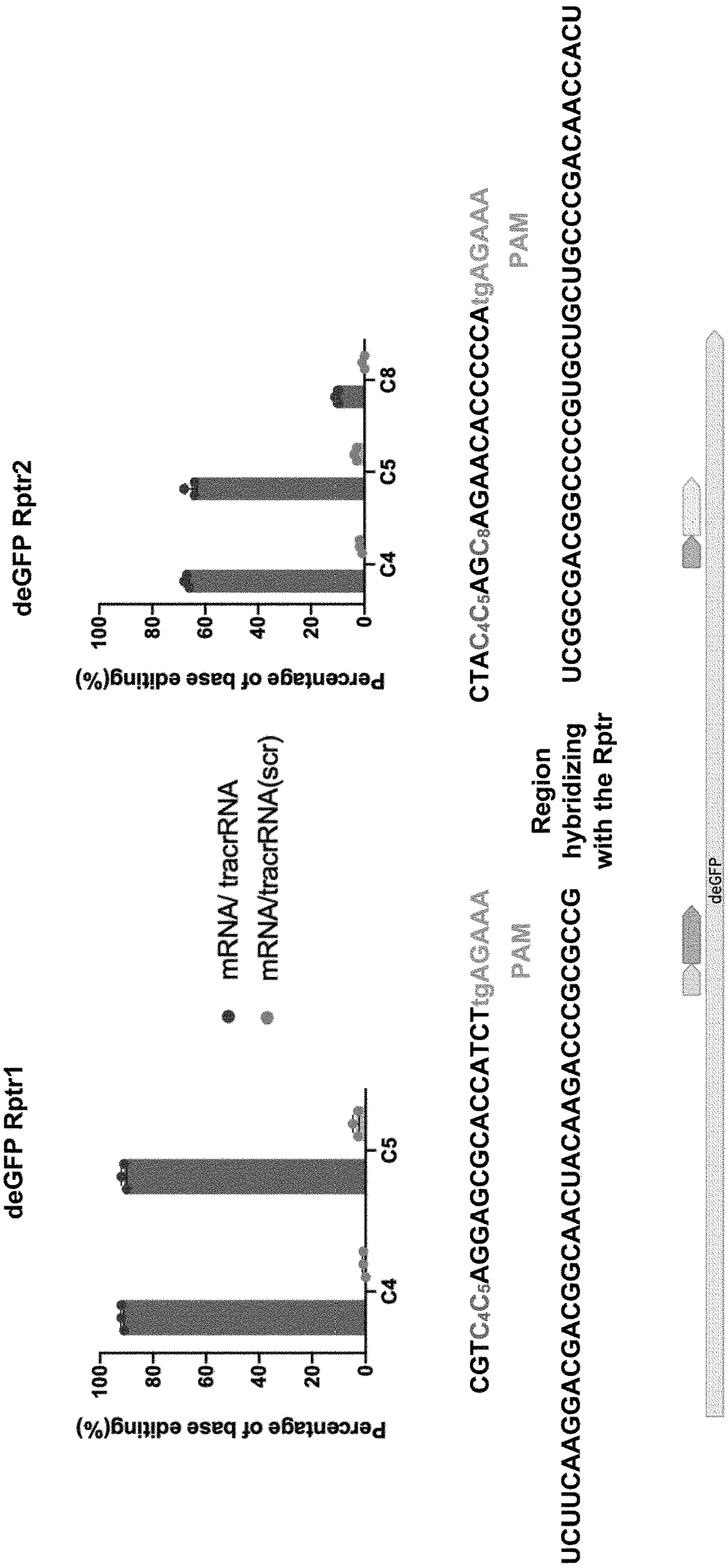

FIG. 21 shows efficient transcriptional recording with a non-natural tracrRNA and a high GC-content mRNA. Non-natural tracrRNAs were designed to hybridize to regions of higher-GC content within the deGFP mRNA, and then base editing was assessed using a target sequence in a plasmid. These results show that low-GC content within the non-natural tracrRNA-hybridizing region of the sensed mRNA is not a requirement for transcriptional recording. Editing was assessed similar to FIG. 19. tracrRNA(scr): tracrRNA with anti-repeat sequence scrambled. The sequences as shown are cgtccaggagcgcaccatcttgagaaa (SEQ ID NO: 105), ctaccagcagaacacccccatgagaaa (SEQ ID NO: 106), ucuucaaggacgacggcaacuacaagacccgcgccg (SEQ ID NO: 107), and ucggcgacggccccgugcugcugcccgacaaccacu (SEQ ID NO: 108).

FIG. 22 shows the transcriptional recording of an endogenous gene in *E. coli*. Here, the non-natural tracrRNA is designed to sense expression of xylA, which is induced when D-xylose is added to the medium. In this case, transcriptional recording using the SthlnCas9 base editor increased when D-xylose was added. These experiments were conducted similar to FIG. 19. The sequences as shown are ttatcgaaccgaaaccgcaatgagaaa (SEQ ID NO: 109), and ggcggtcgtgaaggttacgatgagaaa (SEQ ID NO: 110).

Figure 23:
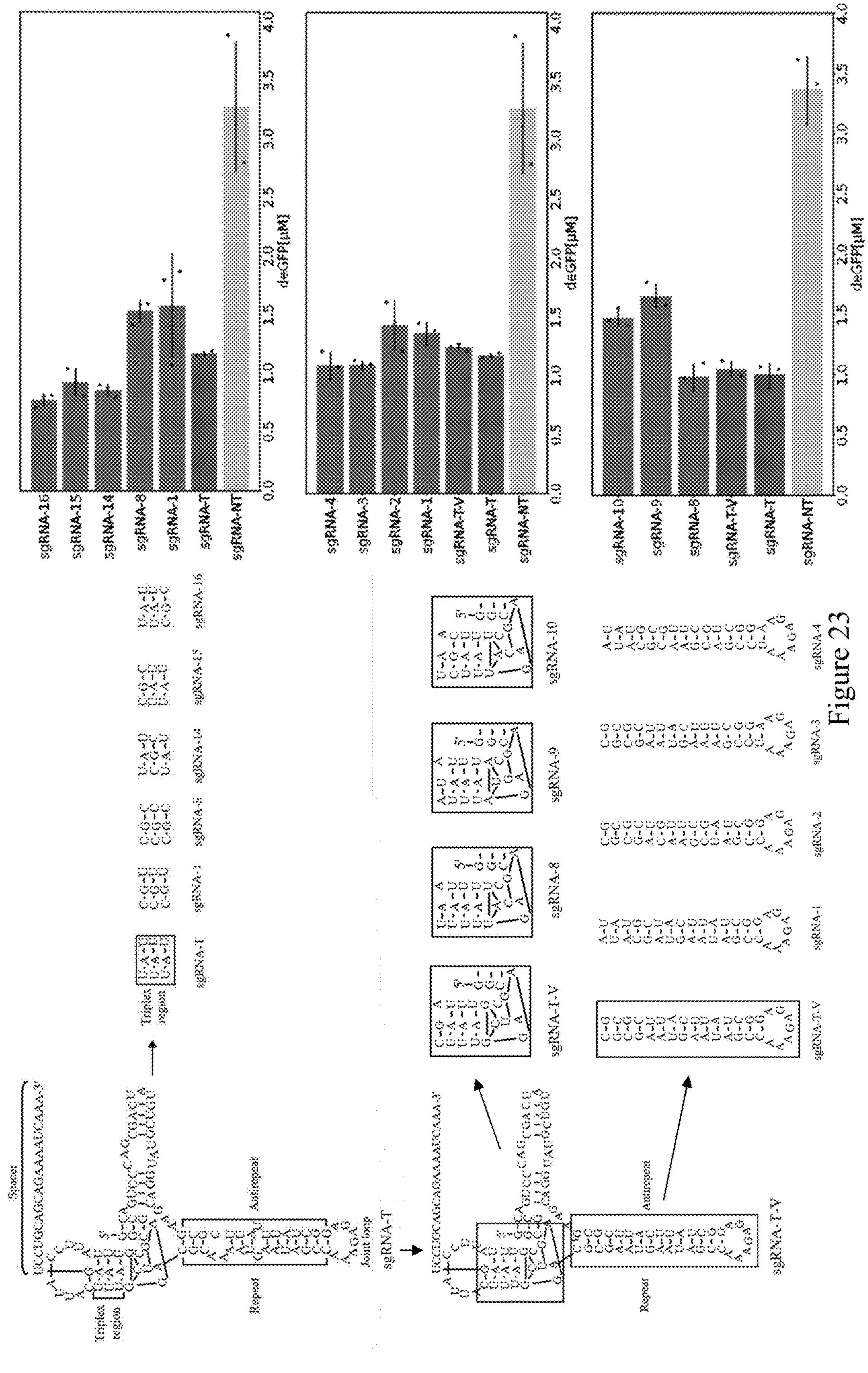

FIG. 23 shows the crRNA:tracrRNA duplex for CasX/Cas12e can be modified (reprogrammed), while still maintaining targeting activity. For this, a systematic mutation analysis was performed. It was confirmed that the non-naturally occurring tracrRNA encoded as an sgRNA still guides sequence-specific DNA cleavage for CasX/12e. The sequences as shown are SEQ ID NO: 111 to SEQ ID NO: 119).

Figure 24:
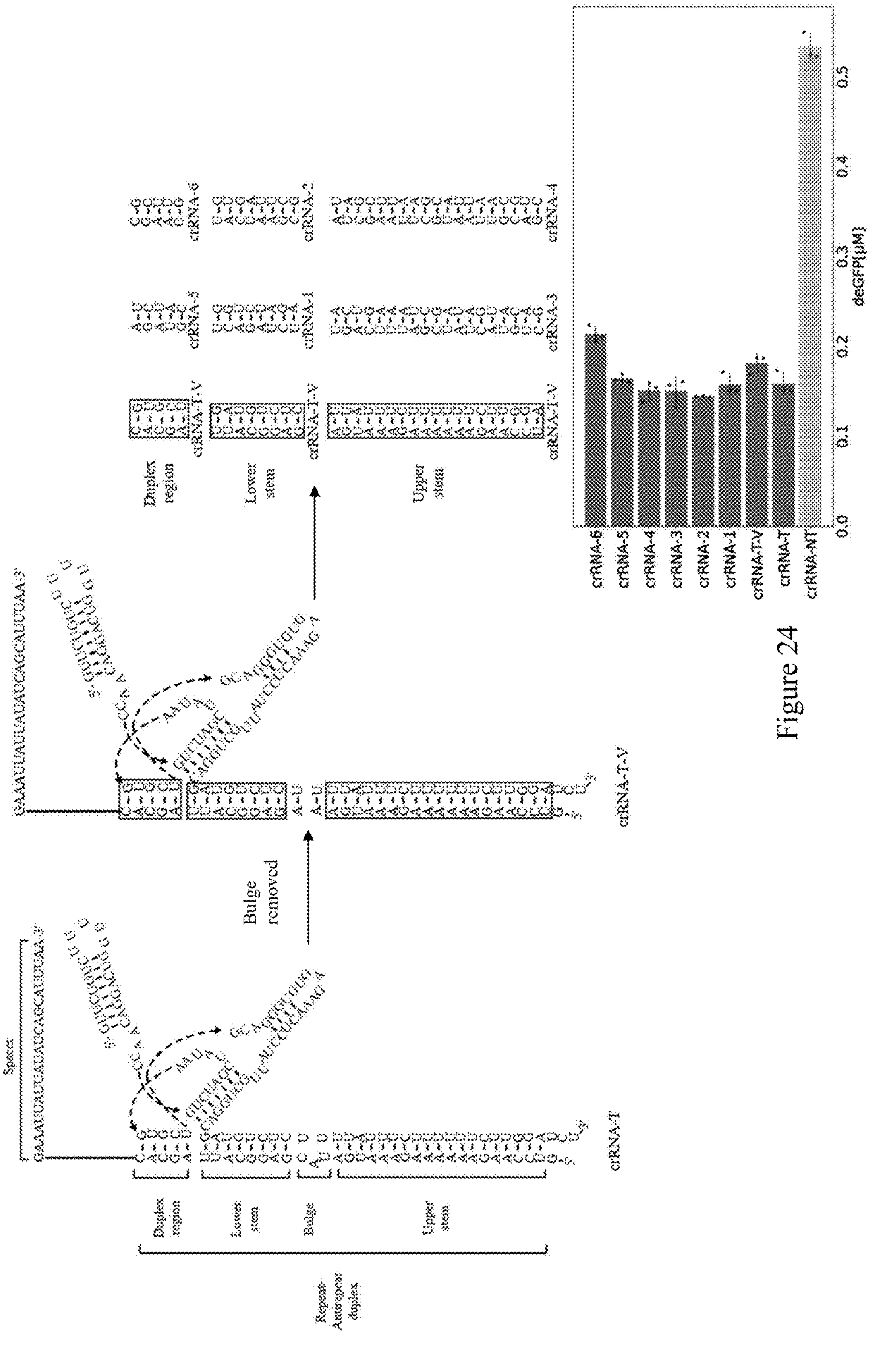

FIG. 24 shows the crRNA:tracrRNA duplex can be modified (reprogrammed), while still maintaining targeting activity. For this, a systematic mutation analysis of BhCas12b tracrRNA/crRNA was performed. It was confirmed that the non-naturally occurring tracrRNA still guides sequence-specific DNA cleavage for BhCas12b. The sequences as shown are SEQ ID NO: 120 to SEQ ID NO: 128).

Figure 25:
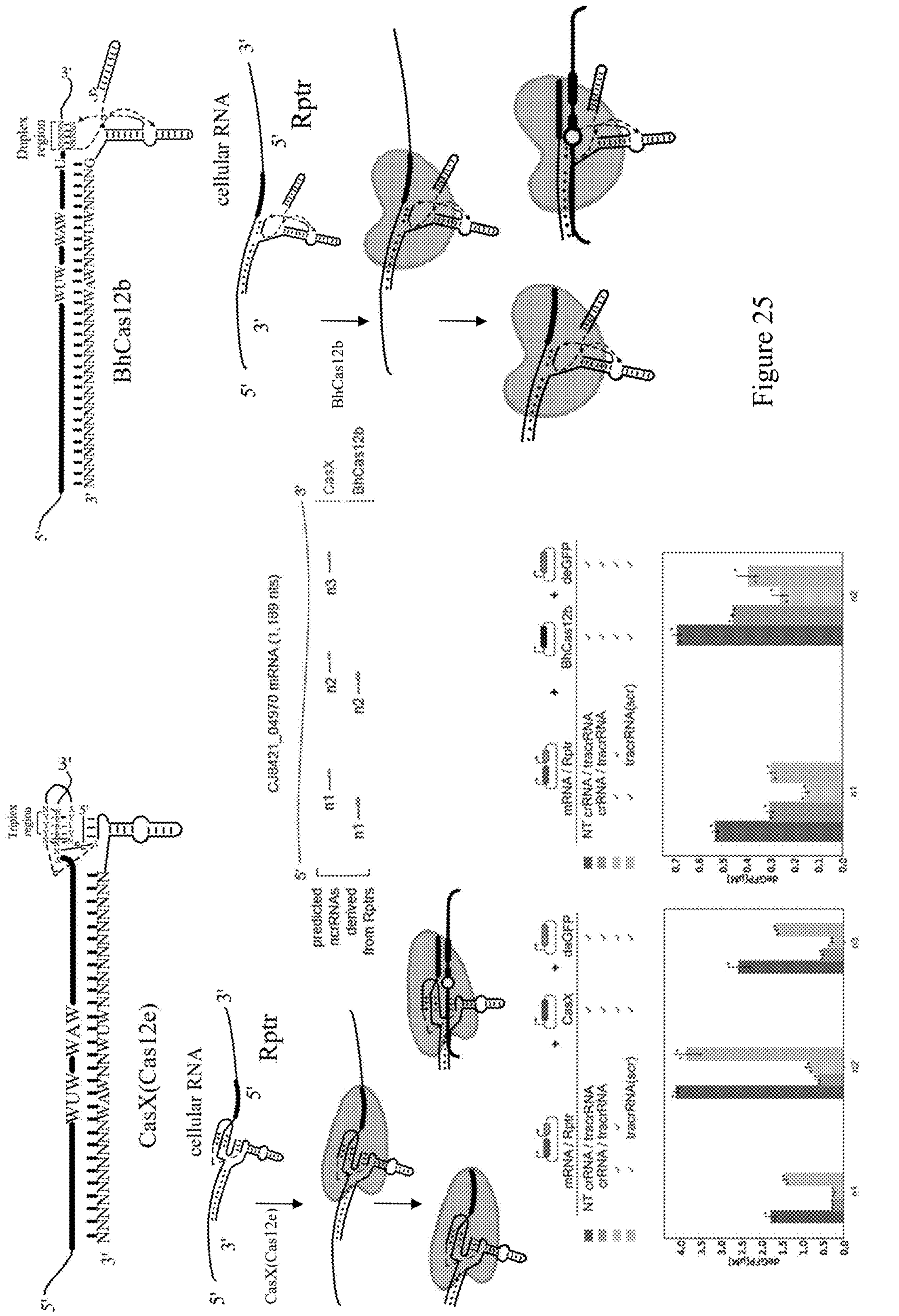

FIG. 25 shows a demonstration of reprogrammed/modified non-naturally occurring tracrRNAs directing DNA cleavage when the sensed RNA is present. The non-naturally occurring tracrRNA still guides sequence-specific DNA cleavage for Cas12b and Cas12e.

EXAMPLES

Construction and growth of *C. jejuni* mutant strains *C. jejuni* mutant strains (deletion, chromosomal 3xFLAG-tagging) were constructed using double-crossover homologous recombination (High-resolution transcriptome maps reveal strain-specific regulatory features of multiple *Campylobacter jejuni* isolates. *PLoS Genet.* 2013; 9(5):e1003495). Briefly, PCR products with 500 bp homologous ends or genomic DNA with desired mutation were introduced into *C. jejuni* using electroporation or natural transformation, respectively, as described previously (High-resolution transcriptome maps reveal strain-specific regulatory features of multiple *Campylobacter jejuni* isolates. *PLoS Genet.* 2013; 9(5):e1003495). *C. jejuni* strains were routinely grown on Müller-Hinton agar plates or with shaking in *Brucella* broth (BB), both supplemented with 10 g/ml vancomycin, at 37° C. under microaerobic (10% $CO_2$, 5% $O_2$) conditions.

RIP-seq of *C. jejuni* Cas9-3xFLAG Co-immunoprecipitation (Co-IP) combined with RNA-seq (RIP-seq) to identify direct RNA binding partners of Cas9-3xFLAG in *C. jejuni* was performed essentially as previously described (CRISPR RNA-Dependent Binding and Cleavage of Endogenous RNAs by the *Campylobacter jejuni* Cas9. *Mol Cell.* 2018; 69(5):893-905.e7).

Briefly, Co-IP of chromosomally tagged Cas9-3xFLAG was performed using anti-FLAG antibody and Protein A-Sepharose beads from the lysates of *C. jejuni* CG8421 cas9-3 x FLAG and WT (untagged, control) strains grown to mid-exponential phase ($OD_{600}$=0.6) at 37° C. Cells were harvested by centrifugation, and pellets were resuspended in 1 mL Buffer A (20 mM Tris-HCl, pH 8.0, 150 mM KCl, 1 mM $MgCl_2$, 1 mM DTT), and subsequently centrifuged (3 min, 11,000×g, 4° C.). The pellets were shock-frozen in liquid nitrogen and stored at −80° C. Frozen pellets were thawed on ice and resuspended in 0.8 mL Buffer A. An equal volume of glass beads was then added to the cell suspension. Cells were lysed using a Retsch MM40 ball mill (30 $s^{-1}$, 10 min) in pre-cooled blocks (4° C.), and centrifuged for 2 min at 15,200×g, 4° C. The supernatant was transferred to a new tube, and an additional 0.4 mL of Buffer A was added to the remaining unlysed cells with beads. Lysis of the remaining cells was achieved by a second round of lysis at 30 $s^{-1}$ for 5 min. Centrifugation was repeated and this second supernatant was combined with the first one. The combined supernatant was centrifuged again for 30 min at 15,200×g, 4° C. for clarification and the resulting supernatant (lysate fraction) was transferred to a new tube. The lysate was incubated with 35 L anti-FLAG antibody (Monoclonal ANTI-FLAG M2, Sigma, #F 1804, RRID: AB_262044) for 30 min at 4° C. on a rocker. Next, 75 L of Protein A-Sepharose (Sigma, #P6649), prewashed with Buffer A, was added and the mixture was rocked for another 30 min at 4° C. After centrifugation, the supernatant was removed and the pelleted beads were washed 5 times with 0.5 mL Buffer A. Finally, 500 L Buffer A was added to the beads and RNA and proteins were separated using phenol-chloroform-isoamyl alcohol. From each CoIP, ~1000 ng of RNA was recovered from the aqueous phase. 100 L of 1× protein loading buffer was added to the final protein sample precipitated along with beads (CoIP sample). For verification of a successful CoIP, protein samples obtained during different stages of the coIP (culture, lysate, supernatant, wash, and CoIP) were analysed using western blot.

cDNA Library Preparation and Deep Sequencing

Residual gDNA was removed using DNase I treatment on the coIP RNA obtained above. cDNA libraries for Illumina sequencing were constructed by vertis Biotechnologie AG, Germany (http://www.vertis-biotech.com) in a strand-specific manner as described previously (High-resolution transcriptome maps reveal strain-specific regulatory features of multiple *Campylobacter jejuni* isolates. *PLoS Genet.* 2013; 9(5):e1003495). In brief, the RNA samples were poly(A)-tailed using poly(A) polymerase. Then, 5'-triphosphates were removed using tobacco acid pyrophosphatase (TAP), and an RNA adaptor was then ligated to the resulting 5'-monophosphate. First-strand cDNA was synthesized with an oligo(dT)-adaptor primer using M-HLV reverse transcriptase. In a PCR-based amplification step, using a high-fidelity DNA polymerase, the cDNA concentration was increased to 10-20 ng/μL. For all libraries, the Agencourt AMPure XP kit (Beckman Coulter Genomics) was used to purify the DNA, which was subsequently analyzed by capillary electrophoresis.

A library-specific barcode for multiplex sequencing was included as part of a 3'-sequencing adaptor. The cDNA inserts were flanked by TruSeq_Sense_primer (SEQ ID NO: 1) and TruSeq_Antisense_NNNNNN_primer (NNNNNN=6nt barcode for multiplexing) (SEQ ID NO: 2). The samples were run on an Illumina HiSeq instrument with ~100 cycles in single-read mode.

Analysis of RIP-seq sequencing data To assure high sequence quality, the Illumina reads in FASTQ were trimmed with a cut-off phred score of 20 by the program fastq_quality_trimmer from FASTX toolkit version 0.0.13. After trimming, we applied the pipeline READemption version 0.4.3 for the following analysis steps: poly(A)-tail sequences were clipped from the 3' ends of reads, size filtering was applied to eliminate read sequences shorter than 12 nt and the collections of remaining reads were mapped to the self-curated *C. jejuni* CG8421 genome using segemehl version 0.2.0 with an accuracy cut-off of 95%.

READemption was used to generate coverage plots representing the numbers of mapped reads per nucleotide. Reads that mapped to multiple locations contributed a fraction to the coverage value. Each read with a minimum overlap of 10 nt was counted with a value based on the number of locations where the read was mapped. If the read overlapped more than one annotation, the value was divided by the number of regions and counted separately for each region (e.g., 1/3 for a read mapped to 3 locations).

For visualization in the Integrated Genome Browser (IGB), the coverage files were normalized to the number of reads that could be mapped from the respective library. To restore the original data range, each graph was then multiplied by the minimum number of mapped reads over the two libraries.

Peak Detection and Binding Motif Analyses

In order to automatically define Cas9-bound RNA regions or peaks from the Cas9-3xFLAG coIP datasets, we applied an in-house tool "sliding_window_peak_calling_script" based on a sliding window approach that was originally developed to detect binding regions of CsrA in *C. jejuni* (The CsrA-FliW network controls polar localization of the dual-function flagellin mRNA in *Campylobacter jejuni. Nat Commun.* 2016; 7:11667). The script has been deposited at Zenodo under https://doi.org/10.5281/zenodo.49292. The script is written in Python 3 and requires installation of the Python 3 packages numpy and scipy for execution.

In brief, the "sliding_window_peak_calling_script" software uses rRNA normalized wiggle files of the Cas9-3xFLAG and control coIP libraries as input to determine sites showing a continuous enrichment of the Cas9-3xFLAG-tagged library compared to the control. The identification of enriched regions is based on four parameters: a minimum required fold-change (FC) for the enrichment, a factor multiplied by the $90^{th}$ percentile of the wiggle graph which reflects the minimum required expression (MRE) in the tagged library, a window size in nt (WS) for which the previous two values are calculated in a sliding window approach, and a nucleotide step size (SS) which defines the steps in which the window is moved along the genomic axis. All consecutive windows that fulfill the enrichment requirements are assembled into a single peak region. The peak detection is performed separately for the forward and reverse strand of each replicon. For the Cas9-3xFLAG coIP datasets, the following parameters were used: FC=5, MRE=3, WS=25 and SS=5. MEME was then used for the prediction of consensus motifs based on the peak sequences. The two significantly enriched motifs were then compared to the crRNA and tracrRNA sequences to deduce their probable mode of binding.

Northern Blot Analysis

For Northern Blot analysis, 100 g of DNaseI treated total RNA sample was loaded on each lane. After separation on 6% polyacrylamide (PAA) gels containing 7 M urea, RNA was transferred to Hybond-XL membranes (GE-Healthcare) by electroblotting. After blotting, the RNA was UV cross-linked to the membrane and hybridized with 732P-ATP end-labeled DNA oligonucleotides.

Plasmids Construction

All primers, gBlocks used in this work were ordered from Integrated DNA Technologies (IDT, Coralville, US). NEBuilder® HiFi DNA Assembly Cloning Kit was used for plasmid construction by Gibson assembly. The associated SEQ ID numbers (SEQ ID NOS: 1 to 96) can be found in the attached sequence listing, which is incorporated by reference in its entirety. Q5 site-directed mutagenesis kit was used for small insertion and nucleotides substitution. Unless otherwise specified, all nucleases used were expressed in plasmids with Cm selective marker and p15A origin of replication (ORI). All sgRNA or tracrRNA-crRNA or tracrRNA-ncrRNA plasmids were expressed in plasmids with Amp selective marker and ColE1 ORI, and all targeted plasmids were expressed in plasmids with Kan selective marker and pSC101 ORI.

For Cas9 and Cas12 plasmid construction, SpyCas9 and *E. coli* codon-optimized CjeCas9 genes were PCR-amplified from plasmids pCB843 and pCB588, then Gibson-assembled into a PCR-linearized vector pCBS583, respectively.

To construct plasmids encoding sgRNAs with different lengths of 5'-overhangs, gBlocks encoding fliF- or 1093-targeting sgRNAs and their variants with different 5'-overhangs were Gibson-assembled into PCR-linearized vector pCSM180, respectively. For crRNA with 5'-overhangs in the dual-RNA-guided (tracrRNA/crRNA) system, the tracrRNA expressing cassette was obtained by PCR-amplification with the template of gBlock CJfr0018 and primer pair of CJpr0304/CJpr0305 (SEQ ID NOs: 3-4) in order to introduce homologous arms with vector and crRNA cassettes. fliF-targeting crRNA and its 5' overhang variants expressing cassettes were obtained by PCR-amplification with the templates of CJfr0022, CJfr0070 and CJfr0071, and primer pair of CJpr0110/CJpr0291 (SEQ ID NOs: 5-9) to introduce homologous arms with vector and tracrRNA cassette. TracrRNA expressing cassette and crRNA with 5'-overhangs expressing cassettes were Gibson-assembled into PCR-linearized vector pCSM180, respectively.

Similar methods were performed in order to construct plasmids encoding crRNA with 3'-overhangs in the dual-RNA system, the only difference was to obtain fliF-targeting crRNA and its 3'-overhang variants expressing cassettes by PCR-amplification with the templates of CJfr0080, CJfr0081 and CJfr0176 (SEQ ID NOs: 10-12).

In order to construct reprogrammed ncrRNA plasmids for CjeCas9, SpyCas9, and SthlCas9, mRNA harboring peak 113 (spanning genes CJ8421_04970 & 04975 & 04980) was used as the template for modified tracrRNAs to target. This peak was one of the RNAs identified as significantly enriched as part of the CjeCas9 co-immunoprecipitation. gBlocks encoding modified tracrRNAs, and the peak 113-harbored mRNA was PCR-amplified from plasmid pCJ174 and Gibson-assembled into PCR-linearized vector pCSM180.

In order to construct a self-targeting ncrRNAs for CjeCas9, the peak 113-harbored mRNA and reporter gene GFP were arranged on one plasmid, and the modified tracrRNA on another plasmid. A PAM sequence was introduced into the base of the repeat-anti-repeat stem of tracrRNA-ncrRNA using Q5 site-directed mutagenesis.

For all targeted plasmids construction, target sequences were inserted upstream of promoter OR2-OR1 or between promoter OR2-OR1 and GFP CDS using Q5 site-directed mutagenesis with the template of pCSM168.

In Vitro DNA Cleavage Assay Using TXTL

TXTL systems were used to characterize the ncrRNAs, and how the tracrRNA can be reprogrammed/modified. The system works by introducing linear or plasmid DNA encoding each component into *E. coli*. The *E. coli* lysate then transcribes and translates the components based on *E. coli* signals (e.g. promoters, RBS). By using a GFP reporter containing the PAM-flanked target of the crRNA (or ncrRNA), the biogenesis and activity of the crRNA/ncrRNA can be monitored over time. The assay was performed as previously described (Rapid and Scalable Characterization of CRISPR Technologies Using an *E. coli* Cell-Free Transcription-Translation System. *Mol Cell.* 2018; 69(1):146-157.e3). All DNA fragments or plasmids used in the assay should be free of nucleases (DNases, RNases) and inhibitors of the TXTL machinery. Cas9, sgRNA/dual-RNA, and deGFP-encoding reporter plasmids were added into myTXTL Sigma 70 Master Mix (Arbor Biosciences) with a final concentration of 1.5 nM, 0.5 nM and 1 nM, respectively. When expressing linear fragments, GamS (Arbor Biosciences) at a final concentration of 5 uM was supplemented, and a fliF-targeted plasmid (pCJ002) with target sequence inserted between promoter and deGFP coding sequence was used. T7 RNA polymerase-encoding plasmid at a final concentration of 0.5 nM was supplemented when expressing T7 promoter-driven genes. Fluorescence was measured on a BioTek Synergy Neo2 plate reader using a 96-well V-bottom plate (Corning Costar 3357) with Excitation filter at 485 nm and Emission filter at 528 nm. Time-course measurements were run for 16 hours at 29° C. with an interval of 3 minutes between reads.

Reprogramming tracrRNA

Peak 113-harbored mRNA was used as the template for reprogram tracrRNAs to the target. Regions containing AT-enriched sequences preferentially recognized by the *E. coli* Rnase III were chosen as targets for reprogrammed tracrRNAs (In vivo cleavage rules and target repertoire of RNase III in *Escherichia coli. Nucleic Acids Res.* 2018; 46(19):10380-10394). These regions contained an AT-enriched motif, and were 25 bp in length for CjeCas9, and 38 bp for SpyCas9 and SthlCas9. For CjeCas9, the anti-repeat part of native tracrRNA was replaced with the sequences complementary to the chosen targets, respectively. For SpyCas9 and SthlCas9, an extra four or three nucleotides were introduced between the 6th and 7th, or between the 9th and 10th nucleotides (counting from bottom to top in the duplex) in the anti-repeat part of tracrRNA to create a bulge, which is necessary to maintain SpyCas9 and SthlCas9 activity (Guide RNA functional modules direct Cas9 activity and orthogonality. *Mol Cell.* 2014; 56(2):333-339). Correspondingly, the 20-bp to 24-bp sequences upstream of these base-pairing regions were treated as spacers.

Plasmid Clearance Assay in *E. coli*

The plasmid clearance assay was performed as previously described (CRISPR RNA-Dependent Binding and Cleavage of Endogenous RNAs by the *Campylobacter jejuni* Cas9. *Mol Cell.* 2018; 69(5):893-905.e7). 40 nM sgRNA, ncrRNA plasmids were electroporated into *E. coli* strains containing Cas9 and targeted or non-targeted plasmids.

After 1 h recovery in SOC medium, 3 ul of 10-fold serial dilutions of these transformants were spotted onto LB plates with Cm+Amp+Kan antibiotics for overnight incubation at 37° C. Colonies from countable spots were used to calculate the fold-reduction of transformation efficiency by dividing non-targeting CFUs by targeting CFUs.

In Vitro RNA Transcription by T7 RNA Polymerase

RNA was in vitro-transcribed for 4 h at 37° C. using HiScribe™ T7 High Yield RNA Synthesis Kit (New England Biolabs) according to the products' manual. The transcribed RNA was purified using RNA Clean & Concentrator-25 (Zymo Research) with residual DNA removed by in-column DNase I treatment according to the products' manual.

In Vitro RNA Transcription and Detection Using LEOPARD

Sensed RNAs and non-natural tracrRNAs were encoded in synthetic gBlocks beginning with a T7 promoter and were transcribed using the HiScribe T7 in vitro transcription kit (New England Biolabs, cat. #E2040S). The transcribed RNAs were purified using RNA Clean & Concentrator-25 (Zymo Research) with residual DNA removed by In-Column DNase I treatment. A Cy5-labeled forward primer paired with different reverse primers were used to PCR-amplify the associated DNA targets from targeted plasmids.

Sensed RNAs and their associated non-natural tracrRNAs were annealed at a 1:1 molar ratio in 1×NEB3.1 buffer (New England Biolabs, cat. #B7203S) by heating at 95° C. for 2 minutes and gradually cooling to 25° C. over 45 min using a thermocycler. SpyCas9 (New England Biolabs, cat. #M0386M) was then added, and the mixture was incubated at room temperature for 25 min to promote RNP assembly. DNA targets were then added, and the reaction was incubated at 37° C. for 1 h to promote DNA cleavage.

To explore the impact of adding RNases on ncrRNA, ShortCut® RNase III (New England Biolabs, cat. #M0245L) at a final concentration of 33.3 U/ml and/or RNase A (Thermo Fisher Scientific, cat. #EN0531) at a final concentration of 166.7 g/ml were added before or during the DNA cleavage step. Proteinase K (New England Biolabs, cat. #P8107S) was then added at a final concentration of 25.8 U/ml, and the reaction was incubated at room temperature for 15 min to digest Cas9. For reactions with unlabeled DNA, the final concentration of the DNA target was 10 nM, while the final concentrations of the sensed RNAs, non-natural tracrRNAs and SpyCas9 were all 200 nM. The unlabeled DNA products were separated on a 2% agarose gel and visualized by Intas GelStick Imager.

For reactions with Cy5-labeled DNA, the final concentration of the DNA target was 2 nM, while the final concentration of each sensed RNA and non-natural tracrRNA was 40 nM. The final concentration of SpyCas9 was 40 nM for individual RNA detection and 360 nM for multiplexed RNA detection. For multiplexed RNA detection, all nine non-natural tracrRNAs and DNA targets were present in a single reaction tube for detecting virus RNAs individually or in a set of three or five.

The resulting products for individual or multiplexed RNA detection were loaded along with Novex® TBE HiDensity buffer without tracking dyes, separated on a 4-20% Novex™ TBE gel (Invitrogen, cat. #EC6225BOX).

Simultaneous Detection of RNAs from Different Respiratory Viruses in One Test and Distinguishing SARS-CoV-2 and its Dominant D614G Variant with Single-Base Resolution Using LEOPARD In vitro RNA transcription and detection using LEOPARD was performed as indicated above. For multiplexed RNA detection, all non-natural tracrRNAs and DNA targets were present in a single reaction tube for detecting virus RNAs individually or in a set of three or five. The resulting products for individual or multiplexed RNA detection were loaded along with Novex® TBE HiDensity buffer without tracking dyes, and separated on a 4-20% Novex™ TBE gel (Invitrogen, cat. #EC6225BOX). The individual products for specific detection of the D614G mutation in the SARS-CoV-2 Spike protein and the experiment with yeast total RNA were loaded on a 2% agarose gel. Images for gels with Cy5 labels were captured on an Amersham Typhoon™ Biomolecular Imager (GE Healthcare). FIG. 18 E shows specific detection of the D614G point mutation within the spike protein of SARS-CoV-2. Each detected T7-transcribed RNA comprised the intended ncrRNA sequence with 50-nt extensions on either end.

The D614G mutation in the spike protein of SARS-CoV-2 serves as a proof of function-example, as this mutation results from a single nt change (A23403G) and has been associated with increased infectivity and its global spread. By placing this nt change within the seed region of the target, the inventors could detect the WT or D614G RNA using one non-natural tracrRNA combined with either the WT or D614G target (FIG. 18 E). The inventors found that the matching DNA target was preferentially cleaved when testing each target individually. However, combining the two targets in a single reaction yielded discernable cleavage only for the matching target, presumably through preferential binding and cleavage of the perfect target by Cas9. LEOPARD therefore can confer multiplexed RNA detection in a single reaction with single-base resolution.

Identifying the Anti-Repeat Region for Different tracrRNAs

As part of designing the non-natural tracrRNAs, the sequence of the anti-repeat region of the tracrRNA is changed to be complementary to a region of the sensed RNA. Identifying these regions is relatively straightforward and can be achieved by evaluating the base-pairing potential of the tracrRNA with one of the repeats in the CRISPR array, such as by using common RNA folding algorithms such as NUPACK or mfold. Alternatively, this region can be determined experimentally by hybridizing purified repeat and purified tracrRNA and then evaluating RNA structure through common probing approaches (e.g. using DMS, SHAPE). The anti-repeat region will be the region either partially or fully base paired with the repeat region and should begin around the 5' end of the tracrRNA sequence. See FIGS. 9-11 for examples.

Use of Non-Natural tracrRNAs for RNA Detection In Vitro

A collection of RNAs are extracted from a sample using common approaches to purify RNA, such as GenEasy RNA extraction kit sold by Sigma-Aldrich or the RNeasy RNA extraction kit sold by Qiagen. The sample can be from a human or animal (e.g. blood, sputum, biopsy), a plant (e.g. clipped root, clipped leaf), soil, water, or air.

A set of RNAs to be detected within each sample are selected based on the specific needs of the user. An accompanying set of non-natural tracrRNAs are designed by changing the sequence of the anti-repeat portion of the tracrRNA to be complementary to a portion of the RNA. FIGS. 9-11 show the regions of the tracrRNA to be changed when using the CjeCas9, the SpyCas9, or the SthlCas9, although a similar approach can be extended to other tracrRNA-dependent CRISPR nucleases. If using the *E. coli* RNase III, A/T-rich sequences are generally preferred, although other variants of RNase III or other dsRNA-cleaving enzymes (e.g. Rntp1, Pac1p, DCL1, Dicer, Drosha) could also be used based on their sequence preferences. The region of complementarity can also be extended or reduced to better promote RNA:RNA hybridization and enzymatic cleavage. Multiple non-natural tracrRNAs can also be designed to recognize different regions of the sensed RNA, thereby generating multiple ncrRNAs from a single transcript. The upstream portion of the region in the sensed RNA that pairs with the non-natural RNA becomes the guide sequence for DNA targeting. The length of this region varies based on the nuclease (e.g. 20-24 nts across the CjeCas9, SpyCas9, and SthlCas9 as shown in FIGS. 9-11). These RNAs are generated by in vitro transcription from a DNA template or by custom synthesis through a standard commercial supplier (e.g. IDT).

A dsDNA target is then designed for each ncrRNA. The target comprises the guide sequence of the ncrRNA flanked by an appropriate PAM recognized by the CRISPR nuclease (e.g. NNNNACAC for CjeCas9, NGG for SpyCas9, NNAGAA for SthlCas9). See FIGS. 9-11 for a visual depiction specifically for the CjeCas9, SpyCas9, and SthlCas9. The dsDNA targets are generated by annealing custom-synthesized DNA oligonucleotides (e.g. from IDT) or from a custom-synthesized dsDNA (e.g. gBlocks from IDT). As part of the synthesis process, different chemical moieties can be added for use of the DNA targets as part of RNA detection in vitro, such as fluorophores and quenchers or tags for click chemistry to add other moieties or to covalently link the DNA to a surface.

The reaction also involves purified tracrRNA-dependent nuclease (e.g. SpyCas9) and optionally the dsRNA-cleaving enzyme (e.g. RNase III). The nuclease can be catalytically-dead or catalytically-active depending on whether the detection step involves target nucleic acid binding or cleavage.

As part of representative detection assays, the purified RNAs from the sample are mixed with the set of non-natural tracrRNAs in a binding buffer that promotes RNA hybridization (e.g. 50 mM Tris-HCl, 150 mM NaCl, 10 mM $MgCl_2$ and 0.05% Tween-20, pH 7.8). and incubated at 37° C. for 10 minutes to form duplexes between the RNAs.

The tracrRNA-dependent CRISPR nuclease and dsRNA-cleaving enzyme are then added, and the mixture is incubated at the same temperature for an additional 20 minutes. During this step, the dsRNA-cleaving enzymes cleaves RNA duplexes, such as those formed between a sensed RNA and a non-natural tracrRNA, and ribonucleoprotein complexes form between the tracrRNA-dependent nuclease and the cleaved RNA duplex. The resulting mixture is then exposed to the DNA targets, allowing ribonucleoprotein complexes to target their respective DNA targets. The DNA targets can be added as soluble molecules or they can be affixed to a solid surface (e.g. magnetic beads, on a silicon chip). A wash step can then be added (e.g. with the binding buffer) to remove RNAs, the dsRNA-cleaving enzyme, unbound ribonucleoprotein complexes, and any cleaved and unaffixed portions of DNA targets.

Finally, the DNA targets are assessed to measure the extent to which they were recognized by the ribonucleoprotein complexes (see FIG. 12 for different representative examples). Different formats can be used here. For instance, the DNA target can include a fluorophore fused to one end and a quencher fused to the other end or in the vicinity on another surface (e.g. when affixing the DNA target to a silicon chip). Cleavage of the target would then release a piece of DNA fused to the quencher, thereby generating a fluorescent signal. The change in size of the DNA can also be measured without the need for a change in a fluorescent signal by separating DNAs by size (e.g. through capillary electrophoresis, gel electrophoresis). As a separate example, the fluorophore and quencher could be attached to either strand on the same side. Nicking of the non-target strand by a mutated version of the tracrRNA-dependent CRISPR nuclease (e.g. Cas9n) could release the strand fused to the quencher, thereby allowing the quencher to diffuse away and producing a fluorescent signal. As a final example, a fluorophore or dye (e.g. FITC, Texas Red) could be fused to the tracrRNA-dependent CRISPR nuclease or the tracrRNA, where the nuclease does not cleave its DNA target (e.g. through mutations to the endonuclease domains or encoding PAM-distal mismatches within the target). By localizing the target to a specific location (e.g. on a silicon chip), the fluorescence/colorimetric intensity at that position reflects a bound ribonucleoprotein complex for that target. This localization can be detected spatially using different approaches such as with cameras or photodiode arrays.

In all of these examples, the measured output is linked to specific DNA targets, thus serving as an indirect readout of the presence of the sensed RNA. The readout can be rendered quantitative to specify the concentration of each sensed RNA in the sample based on the fluorescence intensity. For instance, if a cluster of molecules encoding the same DNA target sequence are present, then the fluorescence intensity would scale with the number of DNA molecules recognized by riboncleoprotein complexes encoding the appropriate ncrRNA—and thus the number of sensed RNA molecules that produced the ncrRNAs.

Beyond using dsDNA targets, ssDNA and RNA targets can also be used as part of the diagnostic platform. Multiple Cas9 and Cas12 nucleases (e.g. CjeCas9, NmeCas9, SauCas9) have been shown to recognize ssDNA and RNA, where recognition involves base pairing to the guide region of the guide RNA but does not involve the PAM. Similar setups for detection could be employed, such attaching a fluorophore to one end and a quencher to the other end of the target so target cleavage releases the quencher, or a fluorophore-conjugated nuclease could localize fluorescence upon target binding.

Some Cas9 nucleases (e.g. SpyCas9) are unable to recognize ssDNA or RNA unless a double-stranded PAM sequence is present next to the target. This could be incorporated into the target design by using a ssDNA target with a fixed sequence for the PAM and flanking sequence. Another ssDNA oligo could then be hybridized to the fixed sequence, providing a double-stranded PAM and flanking sequence with a single-stranded target.

The examples described herein can be used for wide-ranging applications, such as diagnosing medical conditions to inform the course of treatment, identifying SNPs associated with health outcomes or disease, identifying microbial contaminants in potable water, identifying viral or microbial contaminants in fermentations or cell cultures, identifying plant or insect variants, or identifying key microbial members in mixed communities (e.g. in the gut, soil, water).

Use of Non-Natural tracrRNAs for RNA Recording In Vivo

For this application, the non-natural tracrRNAs are employed to record the presence of one or multiple sensed RNAs in a cell in the form of edited DNA or the altered expression of a measurable reporter gene.

The tracrRNA-dependent nuclease and the non-natural tracrRNAs are encoded in linear DNA, a plasmid or a viral construct for delivery and cellular expression. The tracrRNAs can be expressed separately as individual expression constructs or in a single construct with intervening RNA cleavage sequences (e.g. tRNAs, ribozymes).

DNA representing the targets of generated ncrRNAs can be encoded in the same vector or a separate vector, where its composition will depend on how the nucleases are employed to record a detected RNA. See FIGS. 13 and 19 to 22 for representative examples. In one instance, the DNA editing (e.g. indel formation, base editing) serves as the readout, and only a DNA target for each non-natural tracrRNA needs to be encoded. In the case of homology-directed repair or homologous recombination, a recombineering template would also be present in the cell comprising the intended edit flanked by homology arms and in the form of an oligonucleotide, linear dsDNA, or circular DNA. Alternatively, the nuclease can drive expression of a reporter gene, such as a fluorescent RNA aptamer (e.g. RNA spinach), a fluorescent protein (e.g. GFP), or an enzyme that generates a visual output (e.g. LacZ coupled with X-gal). The nuclease then modulates the expression of the reporter (e.g. blocking transcription by targeting the promoter or coding region, recruiting RNA polymerase through a fused or recruited activation domain such as SoxS in bacteria or VP16 in eukaryotic cells).

The constructs can express the dsRNA-cleaving enzyme (e.g. the *E. coli* RNase III) for ncrRNA biogenesis. However, virtually all cells express a dsRNA-cleaving enzyme that can be employed instead. The dsRNA-cleaving enzyme can also be entirely dispensable.

To carry out detection and recording, the DNA constructs are introduced into cells through standard means (e.g. electroporation, chemical transformation, conjugation, transfection, viral delivery), and the DNA can be present only transiently (e.g. through transient transfection) or can be stably maintained (e.g. under selection or integrated into chromosomal DNA). The components are then expressed from the constructs to actively detect the presence of the sensed RNA. If the RNA is present, then it will be converted into an ncrRNA and direct the tracrRNA-dependent nuclease to the target DNA reporter. For reporters that rely on expression, standard techniques can be used to measure reporter activity (e.g. fluorescence by flow cytometry or a fluorescence microtiter plate reader). For reporters that rely on DNA editing, the target could be probed through standard approaches that directly or indirectly output DNA sequences (e.g. Sanger sequencing, next-generation sequencing).

As one example, non-natural tracrRNAs were combined with a base editor derived from the SpyCas9 (e.g. BE3) to sense the expression of a multidrug resistance gene (e.g. encoding NMD-1) or a stress-response gene (e.g. encoding the iron-starvation induced sRNA RyhB) in *E. coli*. The non-natural tracrRNA were designed to hybridize to a portion of the sensed RNA as indicated in FIG. 10. The accompanying guide sequence of the ncrRNA was used to design the target DNA and was selected to contain internal C's that can undergo editing by BE3. This target DNA was then encoded in a plasmid (e.g. pBAD18) along with expression constructs for BE3 and the non-native tracrRNA. The plasmid was then transformed into the *E. coli* strain and cultured with or without a separate plasmid encoding NMD-1 or in the presence of an iron chelator. The plasmid was then isolated and the target DNA amplified for Sanger sequencing analysis. The target site encoded the expected conversion of C's to T's in the strain with the sensed RNA expressed, even if the sensed RNA was no longer expressed by removing the NMD-1 encoding plasmid or adding additional iron to the growth medium. There also was no cross-talk between the two non-natural tracrRNAs and target sites, and detection was multiplexed by encoding by non-natural tracrRNAs and targets and exposing the cells to both the NMD-1 plasmid and the iron chelator. This example can be readily extended to other bacteria as well as eukaryotic cells, such as yeast, animal cells, human cells, or plant cells in which base editing has been shown to be functional.

Paralleling the above example, non-natural tracrRNAs could be combined with the CRISPR transposon based on Cas12k for transcription-dependent recording. Cas12k, the transposon components (TnsB, TnsC, TnsQ), an insertion template flanked by the transposon repeats (e.g. encoding a reporter gene or an antibiotic resistance marker), and the non-natural tracrRNAs could be encoded within expression plasmids along with plasmid DNA encoding the corresponding target sites. Using this setup, the presence of the sensed RNA would drive template insertion proximal to the target sequence. The insertion could then be detected through PCR or sequencing.

Use of Non-Natural tracrRNAs for Transcription-Dependent Targeting

Another application of non-natural tracrRNAs involves editing DNA targets in cells only when the gene is actively transcribed. As part of this application, the non-natural tracrRNA is designed to hybridize to a region of a sensed RNA encoding a PAM sequence recognized by the tracrRNA-dependent CRISPR nuclease. The PAM would be specifically located at the 5' end or 3' end of the hybridizing portion of the sensed RNA for Type II or V CRISPR nucleases, respectively. By encoding the PAM in this location, the resulting ncrRNA can direct the tracrRNA-dependent CRISPR nuclease to the DNA locus encoding the sensed RNA. Because the sensed RNA is an essential component in this process, the DNA locus would only undergo targeting when the sensed RNA is present, and thus when the DNA locus is transcribed. FIG. 14 illustrates this concept, while FIG. 15 provides a proof-of-principle demonstration using TXTL.

To achieve transcription-dependent targeting in cells, the tracrRNA-dependent nuclease and the non-natural tracrRNAs are encoded in a plasmid or viral construct for delivery and cellular expression. The tracrRNAs can be expressed separately as individual expression constructs or in a single construct with intervening RNA cleavage sequences (e.g. tRNAs, ribozymes). The nuclease can drive indel formation or homologous recombination in the presence of a DNA repair template, or the nuclease can generate other edits if modified to function as a base editor or as a prime editor. Alternatively, a catalytically-dead nuclease can modulate expression of the sensed gene, such as blocking transcription or by recruiting the KRAB to drive transcriptional repression.

The constructs can express the dsRNA-cleaving enzyme (e.g. the *E. coli* RNase III) for ncrRNA biogenesis. However, virtually all cells express a dsRNA-cleaving enzyme that can be employed instead.

For example, transcription-dependent editing could be implemented in the context of gene drives in mosquitos only when the target locus is actively transcribed. The non-natural tracrRNA is designed to generate an ncrRNA from the relevant target locus (e.g. the doublesex gene), and the hybridizing region in the sensed RNA encodes a PAM (e.g. NGG at the 5' end of this region when using the SpyCas9). The tracrRNA-dependent CRISPR nuclease, the non-natural tracrRNA, and any genetic cargo are encoded in an expression construct that is inserted into the target locus through standard gene-manipulation techniques for mosquitos. When the resulting mosquitos mate and produce off-spring, the gene drive would be expected to transfer only in cells in which the locus is actively transcribed. The end effect is limited to the tissue type in which the gene drive is transferred and introducing an extra layer of control depending on the expression profile of the locus.

Multiple non-natural tracrRNAs can be designed against the doublesex gene and can be encoded in the gene-drive locus to improve the frequency of transfer and reduce the frequency of drive failure due to the formation of disruptive indels at the target site.

The tracrRNA can be Reprogrammed to Direct Cas9 Activity by an RNA-of-Interest

The conversion of a cellular RNA into an ncrRNA was based on sequences bearing extensive complementarity to the tracrRNA anti-repeat, analogous to the natural biogenesis of crRNAs. If the tracrRNA anti-repeat sequence can be changed to hybridize to other RNAs while maintaining the appropriate structure for Cas9 recognition, then the resulting non-natural tracrRNA could drive the conversion of any expressed cellular RNA into an ncrRNA, which guides Cas9 to matching DNA targets (FIG. 17A).

Naturally, the CjeCas9 recognizes a perfect RNA duplex formed between the crRNA repeat and tracrRNA anti-repeat. Based on mutational analysis of the crRNA repeat, the inventors already observed that the crRNA repeat:tracrRNA anti-repeat duplex can accommodate several mutations. Therefore, the inventors evaluated GFP silencing in TXTL after mutating both sides of the duplex in the fliF sgRNA while preserving the secondary structure (s26-s31, FIG. 17 B). GFP silencing was maintained even when exchanging the sequence of the entire duplex (s31, FIG. 17 B). Next, the inventors reprogrammed the tracrRNA anti-repeat to form perfect 25-bp duplexes with three putative ncrRNAs (derived from fliF, CJ8421_04280, CJ8421_04970) exhibiting at most modest GFP silencing in TXTL. In all three cases, GFP repression was significantly enhanced with non-natural tracrRNAs than with WT tracrRNAs (p=1×10−6−0.0011), even if repression was not as strong as with the canonical crRNA:tracrRNA pair (FIG. 17 C). Finally, the inventors reprogrammed the tracrRNA anti-repeat to base pair with entirely new regions of an mRNA (FIG. 17 D). Starting with the mRNA encoding the CJ8421_04970 CDS, the inventors designed five different CjeCas9 non-natural tracrRNAs hybridizing to different locations (n1-n5) in the mRNA (FIG. 17 D). Of these non-natural tracrRNAs, four yielded significantly reduced GFP levels compared to non-targeting crRNA controls (p=6×10-7-0.002). Importantly, mutating the predicted seed region, scrambling the tracrRNA anti repeat, or replacing CjeCas9 with FnCas12a restored GFP expression (FIG. 17 D). Non-natural tracrRNAs therefore can be employed to direct DNA targeting by CjeCas9 with an RNA-of-interest.

Given the functionality of CjeCas9 non-natural tracrRNAs, the inventors asked whether tracrRNAs for other Cas9 homologs can be similarly reprogrammed. The inventors selected the well-characterized *Streptococcus pyogenes* Cas9 (SpyCas9) and the *Streptococcus thermophilus* CRISPRI Cas9 (SthlCas9) as examples. In both cases, the inventors devised design rules for non-natural tracrRNAs based on the known secondary structure of the crRNA:tracrRNA duplex and the preference of RNase III to cleave double stranded RNA with AT-rich sequences. All ten tested non-natural tracrRNAs significantly reduced GFP levels compared to the non-targeting crRNA control (p=1×10−7−1×10−4). As before, GFP expression was restored by disrupting the seed sequence in the ncrRNA guide, scrambling the tracrRNA anti-repeat, or swapping either of the Cas9's for FnCas12a. In many cases, the extent of GFP silencing approached that of the targeting crRNA control (FIG. 17 D). The inventors also evaluated targeted plasmid clearance with non-natural tracrRNAs in *E. coli* for all three Cas9 orthologs, finding that each one could elicit efficient plasmid clearance for at least one tested non-natural tracrRNAs (FIG. S8B). Overall, the tracrRNA for different Cas9 orthologs can be converted into non-natural tracrRNAs to elicit DNA targeting based on the presence of a selected cellular RNA.

Reprogrammed tracrRNAs Enable Sequence-Specific and Multiplexed RNA Detection by Cas9

By linking DNA targeting to an RNA-of-interest, non-natural tracrRNAs offer a unique opportunity for RNA detection and a different paradigm for CRISPR diagnostics. Current CRISPR diagnostics rely on Cas12a or Cas13 searching for double-stranded DNA or RNA targets in a sample, where target recognition elicits non-specific single-stranded DNA or RNA cleavage of a fluorescent reporter. The non-specific readout effectively limits one test to one target sequence. In contrast, non-natural tracrRNAs would convert sensed RNAs into ncrRNAs, and the ncrRNAs would direct Cas9 to bind or cleave matching DNA. Cas9 binding or cleavage of a DNA sequence would then indicate whether the associated RNA is present in the sample. Because the sequence of each DNA target is unique, large numbers of target sequences could be monitored in parallel in one test. The inventors designate the resulting diagnostic platform as LEOPARD, for Leveraging Engineering tracrRNAs and On-target DNAs for PArallel RNA Detection (FIG. 18 A).

Figure 4B:
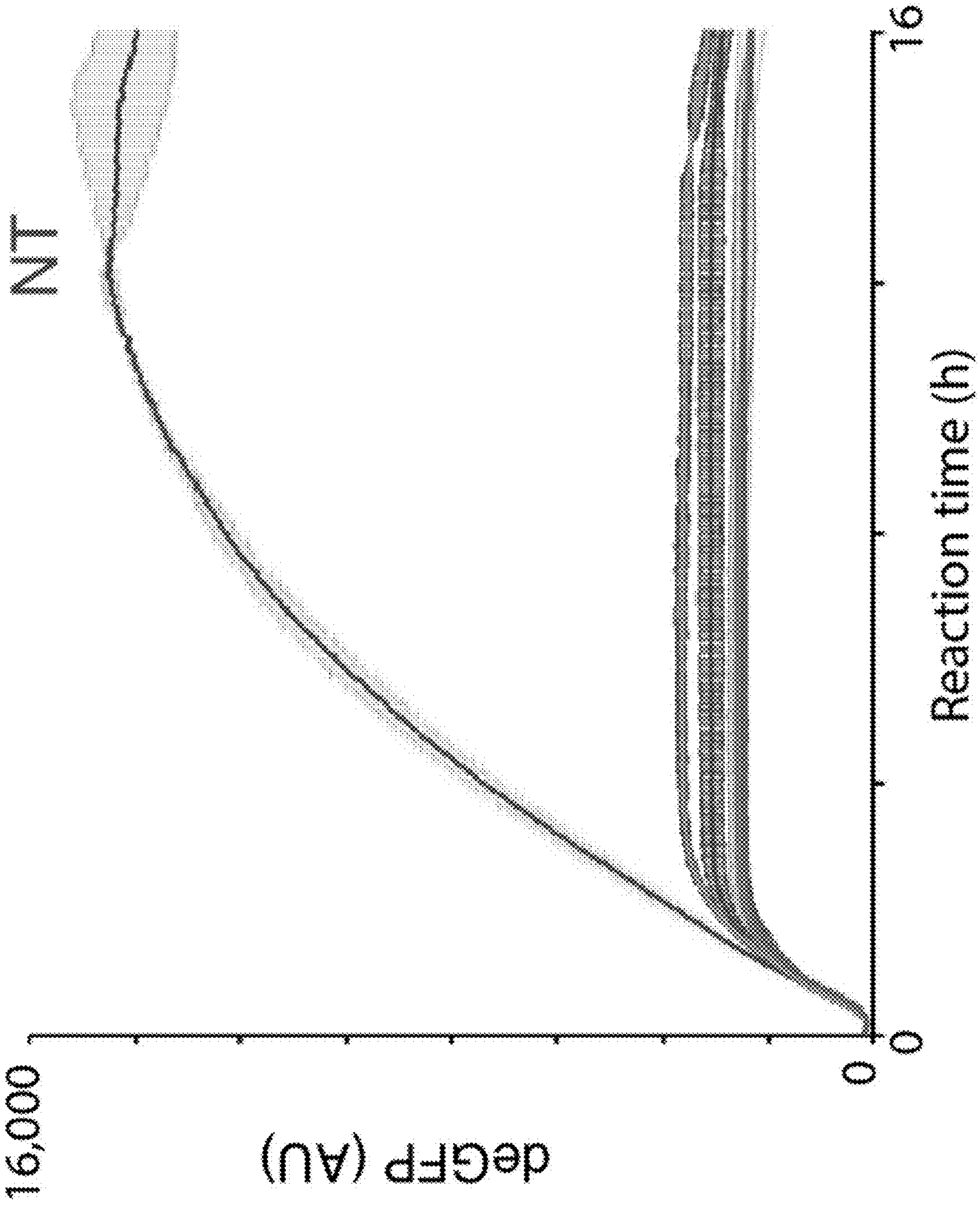

To begin assessing LEOPARD, the inventors performed a simplified in vitro reaction using T7-transcribed RNAs, commercially available Cas9 protein, and linear DNA targets. The inventors began with RNA corresponding to one of the synthetic ncrRNA loci within CJ8421_04970 (FIG. 17 D), and resolved cleaved and uncleaved DNA targets by size using gel electrophoresis. They found that introducing an annealing step to hybridize the non-natural tracrRNA to the T7-transcribed ncrRNA yielded DNA target cleavage, even when the ncrRNA sequence was extended on either end. They also determined that, with the annealing step, adding RNase III or RNase A was not necessary and even partially interfered with the apparent DNA cleavage. Efficient cleavage could also occur with a 100-fold excess of yeast total RNA, but only when the ncrRNA was present (FIG. 4B). LEOPARD therefore reports the presence of a specific RNA-of-interest based on cleavage of a DNA target.

Realizing the full multiplexing potential of LEOPARD requires monitoring many DNA targets at once. The inventors therefore devised a readout scheme based on resolving distinct cleavage products from pooled DNA targets by gel electrophoresis (FIG. 18 C). Each target is labeled with a fluorophore on one end, producing only two visualizable products-cleaved and uncleaved. They then applied this scheme to specifically detect nine ~150-nt RNA fragments associated with respiratory viruses, including two from SARS-CoV-2 coronavirus (the causative agent of COVID-19), six from other coronaviruses, and one from influenza H1N1 (FIGS. 18 B, D). The inventors found that each DNA target was cleaved by Cas9 only in the presence of the corresponding RNA. Furthermore, this scheme allowed us to specifically detect three or five RNA fragments in the same reaction, demonstrating the capacity of LEOPARD for multiplexed detection. Finally, as the viral RNA sequences were selected to minimize homology, we asked if LEOPARD could detect even a single-nucleotide difference.

The invention claimed is:

1. A method for detecting, in a cell, tissue, and/or sample, at least one sensed RNA that hybridizes to a tracrRNA that is not a crRNA, said method comprising:

a) contacting said cell, tissue and/or sample with at least one non-naturally occurring tracrRNA comprising an anti-repeat portion that specifically hybridizes with a first portion of said sensed RNA, wherein a second portion of said sensed RNA specifically hybridizes with at least one target nucleic acid; wherein said at least one non-naturally occurring tracrRNA is hybridized or is able to be hybridized with said sensed RNA in the presence of at least one tracrRNA-dependent CRISPR nuclease enzyme, optionally further comprising the presence of at least one RNA-cleaving enzyme;

b) detecting binding of said at least one tracrRNA-dependent CRISPR nuclease enzyme to said at least one target nucleic acid;

wherein binding detects said at least one sensed RNA in said cell, tissue and/or sample.

2. A method for recording transcription of at least one target DNA in a cell, tissue and/or sample, said method comprising:

a) contacting said sample, cell and/or tissue with at least one non-naturally occurring tracrRNA comprising an anti-repeat portion that specifically hybridizes with a first portion of a sensed RNA that is not a crRNA, wherein a second portion of said sensed RNA specifically hybridizes with said at least one target DNA; wherein said at least one non-naturally occurring tracrRNA is hybridized or is able to be hybridized with said sensed RNA in the presence of at least one tracrRNA-dependent CRISPR nuclease enzyme, optionally further comprising the presence of at least one RNA-cleaving enzyme; and b) nicking or cleaving of said at least one target nucleic acid in said sample by said nuclease, c) detectably editing said at least one target DNA comprising; and d) optionally, detecting said editing of said at least one target DNA;

e) wherein detecting said editing of said at least one target DNA records transcription of said at least one sensed RNA in said cell, tissue and/or sample.

3. The method according to claim 1, wherein said at least one sensed RNA is environment, species, strain, disease, cell- and/or tissue specific or related to a condition selected from infection with a pathogen, a metabolic disease, cancer, a neurodegenerative disease, ageing, a drug, and biotic or abiotic stress.

4. The method according to claim 1, wherein said at least one sensed RNA is added to said cell, tissue and/or sample prior to step a), and/or further comprising a step of transcribing DNA into sensed RNA prior to step a).

5. The method according to claim 1, further comprising detecting the amount of said at least one target nucleic acid and/or said at least one sensed mRNA in said sample, tissue and/or cell, and further comprising detecting a change in the amount of said at least one target nucleic acid and/or said at least one sensed mRNA in said sample, tissue and/or cell when compared to a control.

6. A method for detecting a medical condition in a mammal, wherein said condition is related to the presence of, expression of and/or mutation(s) in at least one sensed RNA, comprising performing the method according to claim 1, and detecting said medical condition based on the presence of, expression of and/or mutation(s) in said at least one sensed RNA as detected, wherein said at least one sensed RNA is environment, species, strain, disease, cell- and/or tissue specific or related to a condition selected from infection with a pathogen, a metabolic disease, cancer, neurodegenerative diseases, ageing, a drug, and biotic or abiotic stress, wherein optionally said at least one sensed RNA is added to said cell, tissue and/or sample prior to step a), and/or further comprising a step of transcribing DNA into sensed RNA prior to step a).

7. The method according to claim 1, wherein said editing of said at least one target DNA comprises non-homologous end joining (NHEJ) repair, microhomology-mediated end joining (MMEJ), homologous-directed repair (HDR), a detectable marker, a detectable modification, base editing, prime editing or RNA editing.

8. A method for detecting, in a cell, tissue, and/or sample, at least one sensed RNA that hybridizes to a tracrRNA that is not a crRNA, said method comprising:

a) contacting said cell, tissue, and/or sample with at least one non-naturally occurring tracrRNA comprising an anti-repeat portion that specifically hybridizes with a first portion of said sensed RNA, wherein a second portion of said sensed RNA specifically hybridizes with at least one target nucleic acid; wherein said at least one non-naturally occurring tracrRNA is hybridized or is able to be hybridized with said sensed RNA in the presence of at least one tracrRNA-dependent CRISPR nuclease enzyme, optionally further comprising the presence of at least one RNA-cleaving enzyme; and b) detecting cleavage of said at least one target nucleic acid in said sample by said nuclease enzyme;

wherein detecting said cleavage of at least one target nucleic acid detects said at least one sensed RNA in said cell, tissue and/or sample.

9. The method according to claim 8, wherein said at least one sensed RNA is environment, species, strain, disease, cell- and/or tissue specific or related to a condition selected from infection with a pathogen, a metabolic disease, cancer, a neurodegenerative disease, ageing, a drug, and biotic or abiotic stress.

10. The method according to claim 8, wherein said at least one sensed RNA is added to said cell, tissue and/or sample prior to step a), and/or further comprising a step of transcribing DNA into sensed RNA prior to step a).

11. The method according to claim 8, further comprising detecting the amount of said at least one target nucleic acid and/or said at least one sensed mRNA in said sample, tissue and/or cell, and further comprising detecting a change in the amount of said at least one target nucleic acid and/or said at least one sensed mRNA in said sample, tissue and/or cell when compared to a control.

12. A method for detecting a medical condition in a mammal, wherein said condition is related to the presence of, expression of and/or mutation(s) in at least one sensed RNA, comprising performing the method according to claim 8, and detecting said medical condition based on the presence of, expression of and/or mutation(s) in said at least one sensed RNA as detected, wherein said at least one sensed RNA is environment, species, strain, disease, cell- and/or tissue specific or related to a condition selected from infection with a pathogen, a metabolic disease, cancer, neurodegenerative diseases, ageing, a drug, and biotic or abiotic stress, wherein optionally said at least one sensed RNA is added to said cell, tissue and/or sample prior to step a), and/or further comprising a step of transcribing DNA into sensed RNA prior to step a).

13. The method according to claim 8, wherein said editing of said at least one target DNA comprises non-homologous end joining (NHEJ) repair, microhomology-mediated end joining (MMEJ), homologous-directed repair (HDR), a detectable marker, a detectable modification, base editing, prime editing or RNA editing.

14. A method for detecting, in a cell, tissue, and/or sample, at least one sensed RNA that hybridizes to a tracrRNA that is not a crRNA, said method comprising:

a) contacting said cell, tissue and/or sample with at least one non-naturally occurring tracrRNA comprising an anti-repeat portion that specifically hybridizes with a first portion of said sensed RNA, wherein a second portion of said sensed RNA specifically hybridizes with at least one target nucleic acid; wherein said least one non-naturally occurring tracrRNA is hybridized or is able to be hybridized with said sensed RNA in the presence of at least one tracrRNA-dependent CRISPR nuclease enzyme, optionally further comprising the presence of at least one RNA-cleaving enzyme;

b) nicking or cleaving of said at least one target nucleic acid in said sample by said nuclease, c) detectably editing said at least one target nucleic acid, and d) detecting said editing of said at least one target nucleic acid;

wherein detecting said editing of said at least one target nucleic acid detects said at least one sensed RNA in said cell, tissue and/or sample.

15. The method according to claim 14, wherein said at least one sensed RNA is environment, species, strain, disease, cell- and/or tissue specific or related to a condition selected from infection with a pathogen, a metabolic disease, cancer, a neurodegenerative disease, ageing, a drug, and biotic or abiotic stress.

16. The method according to claim 14, wherein said at least one sensed RNA is added to said cell, tissue and/or sample prior to step a), and/or further comprising a step of transcribing DNA into sensed RNA prior to step a).

17. The method according to claim 14, further comprising detecting the amount of said at least one target nucleic acid and/or said at least one sensed mRNA in said sample, tissue and/or cell, and further comprising detecting a change in the amount of said at least one target nucleic acid and/or said at least one sensed mRNA in said sample, tissue and/or cell when compared to a control.

18. A method for detecting a medical condition in a mammal, wherein said condition is related to the presence of, expression of and/or mutation(s) in at least one sensed RNA, comprising performing the method according to claim 14, and detecting said medical condition based on the presence of, expression of and/or mutation(s) in said at least one sensed RNA as detected, wherein said at least one sensed RNA is environment, species, strain, disease, cell- and/or tissue specific or related to a condition selected from infection with a pathogen, a metabolic disease, cancer, neurodegenerative diseases, ageing, a drug, and biotic or abiotic stress, wherein optionally said at least one sensed RNA is added to said cell, tissue and/or sample prior to step a), and/or further comprising a step of transcribing DNA into sensed RNA prior to step a).

19. The method according to claim 14, wherein said editing of said at least one target DNA comprises non-homologous end joining (NHEJ) repair, microhomology-mediated end joining (MMEJ), homologous-directed repair (HDR), a detectable marker, a detectable modification, base editing, prime editing or RNA editing.

* * * * *